(12) United States Patent
Solomon

(10) Patent No.: US 11,998,885 B2
(45) Date of Patent: Jun. 4, 2024

(54) FLUIDIC DEVICES WITH REACTION WELLS AND CONSTRICTION CHANNELS AND USES THEREOF

(71) Applicant: Unchained Labs, Pleasanton, CA (US)

(72) Inventor: Deepak Solomon, San Diego, CA (US)

(73) Assignee: Unchained Labs, Pleasanton, CA (US)

( * ) Notice: Subject to any disclaimer, the term of this patent is extended or adjusted under 35 U.S.C. 154(b) by 374 days.

(21) Appl. No.: 17/288,813

(22) PCT Filed: Oct. 25, 2019

(86) PCT No.: PCT/US2019/058202
§ 371 (c)(1),
(2) Date: Apr. 26, 2021

(87) PCT Pub. No.: WO2020/087032
PCT Pub. Date: Apr. 30, 2020

(65) Prior Publication Data
US 2022/0266212 A1 Aug. 25, 2022

Related U.S. Application Data

(60) Provisional application No. 62/751,266, filed on Oct. 26, 2018.

(51) Int. Cl.
*B01J 19/00* (2006.01)
*C07K 1/30* (2006.01)

(52) U.S. Cl.
CPC ............ *B01J 19/0046* (2013.01); *C07K 1/30* (2013.01); *B01J 2219/00306* (2013.01); *B01J 2219/00725* (2013.01); *B01J 2219/00734* (2013.01)

(58) Field of Classification Search
CPC . B01F 33/304; B01F 33/3045; B01J 19/0046; B01J 19/0093; B01J 2219/00015;
(Continued)

(56) References Cited

U.S. PATENT DOCUMENTS

| 723,826 A | 3/1903 | Buysse |
|---|---|---|
| 5,932,418 A | 8/1999 | Yager |

(Continued)

FOREIGN PATENT DOCUMENTS

| AU | 2013204820 B2 | 1/2014 |
|---|---|---|
| CA | 2521862 A1 | 10/2004 |

(Continued)

OTHER PUBLICATIONS

Clausell-Tormos, et al., "An Automated Two-phase Microfluidic System for Kinetic Analyses and the Screening of Compound Libraries," Lab on a Chip, 2010, Issue 10, pp. 1302-1307.

(Continued)

*Primary Examiner* — Jennifer Wecker
(74) *Attorney, Agent, or Firm* — COOLEY LLP

(57) ABSTRACT

The present disclosure provides fluidic devices and fluidic device assemblies, including microfluidic devices and cartridges comprising the same, that in illustrative embodiments, can be used to make particles or protein precipitates, or to monitor precipitate formation. The fluidic devices typically include channels that connect a reaction well to an inlet port and an outlet port, and a fluidic constriction channel that is configured to help retain fluids in the reaction well and/or promote mixing within the reaction well. In some aspect, fluidic devices are interconnected into fluidic assemblies that can be used in continuous process methods.

15 Claims, 41 Drawing Sheets

(58) Field of Classification Search
CPC .... B01J 2219/00306; B01J 2219/00725; B01J 2219/00734; B01J 2219/00792; B01J 2219/00813; B01J 2219/0086; B01J 2219/00864; B01J 2219/00867; B01J 2219/00869; B01J 2219/00891; B01J 2219/00905; B01L 2200/0668; B01L 2400/086; B01L 3/502746; B01L 3/502761; C07K 1/30

See application file for complete search history.

(56) References Cited

U.S. PATENT DOCUMENTS

| | | | |
|---|---|---|---|
| 6,048,734 | A | 4/2000 | Burns et al. |
| 6,293,012 | B1 | 9/2001 | Moles |
| 6,319,469 | B1 | 11/2001 | Mian et al. |
| 7,708,949 | B2 | 5/2010 | Stone et al. |
| 8,592,221 | B2 | 11/2013 | Fraden et al. |
| 8,765,485 | B2 | 7/2014 | Link et al. |
| 9,315,768 | B2 | 4/2016 | Vrouwe et al. |
| 10,875,017 | B2 | 12/2020 | Solomon et al. |
| 10,981,166 | B2 | 4/2021 | Solomon |
| 11,305,279 | B2 | 4/2022 | Solomon |
| 2002/0033193 | A1 | 3/2002 | McNeely et al. |
| 2002/0036018 | A1 | 3/2002 | McNeely et al. |
| 2002/0075363 | A1 | 6/2002 | McNeely et al. |
| 2002/0097633 | A1 | 7/2002 | O'Connor |
| 2003/0138829 | A1 | 7/2003 | Unger et al. |
| 2003/0159999 | A1 | 8/2003 | Oakey et al. |
| 2004/0072278 | A1 | 4/2004 | Chou et al. |
| 2004/0137607 | A1 | 7/2004 | Tanaami et al. |
| 2004/0206408 | A1 | 10/2004 | Peters et al. |
| 2006/0018790 | A1 | 1/2006 | Naka et al. |
| 2007/0037199 | A1 | 2/2007 | Takahashi et al. |
| 2007/0110631 | A1 | 5/2007 | Ajdari |
| 2007/0125942 | A1 | 6/2007 | Kido |
| 2007/0195127 | A1 | 8/2007 | Ahn et al. |
| 2008/0233607 | A1 | 9/2008 | Yu et al. |
| 2009/0136982 | A1 | 5/2009 | Tang et al. |
| 2009/0151792 | A1 | 6/2009 | Noda |
| 2010/0165784 | A1 | 7/2010 | Jovanovich et al. |
| 2010/0221831 | A1 | 9/2010 | Miyazaki et al. |
| 2010/0252118 | A1 | 10/2010 | Fraden et al. |
| 2011/0256574 | A1 | 10/2011 | Zhang et al. |
| 2011/0269226 | A1 | 11/2011 | Van Noort et al. |
| 2011/0301058 | A1 | 12/2011 | Cheng et al. |
| 2012/0219947 | A1 | 8/2012 | Yurkovetsky |
| 2012/0244043 | A1 | 9/2012 | Leblanc et al. |
| 2013/0136694 | A1 | 5/2013 | Russo Da Conceição Martinho et al. |
| 2013/0236376 | A1 | 9/2013 | Augstein et al. |
| 2013/0280131 | A1 | 10/2013 | Handique et al. |
| 2013/0337578 | A1 | 12/2013 | Delamarche et al. |
| 2013/0344496 | A1* | 12/2013 | Peytavi .............. B01L 3/502746 435/6.12 |
| 2014/0051062 | A1 | 2/2014 | Vanapalli et al. |
| 2014/0246098 | A1 | 9/2014 | Fraden et al. |
| 2014/0302160 | A1 | 10/2014 | Achrol et al. |
| 2014/0377850 | A1 | 12/2014 | Handique et al. |
| 2015/0044688 | A1 | 2/2015 | Richter et al. |
| 2015/0125947 | A1 | 5/2015 | Korczyk et al. |
| 2015/0184127 | A1 | 7/2015 | White et al. |
| 2016/0214104 | A1 | 7/2016 | Schwemmer et al. |
| 2016/0332163 | A1 | 11/2016 | Wang et al. |
| 2016/0361715 | A1 | 12/2016 | Shi et al. |
| 2016/0361716 | A1 | 12/2016 | Solomon |
| 2017/0232440 | A1 | 8/2017 | Ismagilov et al. |
| 2018/0071735 | A1 | 3/2018 | Linder et al. |
| 2019/0054467 | A1 | 2/2019 | Handique |
| 2020/0055051 | A1 | 2/2020 | Solomon et al. |
| 2020/0179930 | A1 | 6/2020 | Solomon |
| 2020/0261910 | A1 | 8/2020 | Solomon |
| 2021/0114022 | A1 | 4/2021 | Solomon et al. |

FOREIGN PATENT DOCUMENTS

| | | |
|---|---|---|
| EP | 2364774 A2 | 9/2011 |
| EP | 3615220 A1 | 3/2020 |
| FR | 2897282 A1 | 8/2007 |
| JP | 2000515630 A | 11/2000 |
| JP | 2004163104 A | 6/2004 |
| WO | WO-2006052223 A1 | 5/2006 |
| WO | WO-2006096571 A2 | 9/2006 |
| WO | WO-2008097559 A2 | 8/2008 |
| WO | WO-2008130623 A1 | 10/2008 |
| WO | WO-2010111231 A1 | 9/2010 |
| WO | WO-2012154688 A2 | 11/2012 |
| WO | WO-2016118949 A1 | 7/2016 |
| WO | WO-2016187561 A1 | 11/2016 |
| WO | WO-2016201163 A1 | 12/2016 |
| WO | WO-2016201430 A1 | 12/2016 |
| WO | WO-2017027838 A1 | 2/2017 |
| WO | WO-2017180949 A1 | 10/2017 |
| WO | WO-2018200896 A1 | 11/2018 |
| WO | WO-2019032690 A1 | 2/2019 |
| WO | WO-2019094775 A1 | 5/2019 |
| WO | WO-2020087032 A2 | 4/2020 |
| WO | WO-2021067353 A1 | 4/2021 |
| WO | WO-2022146770 A1 | 7/2022 |
| WO | WO-2023023492 A1 | 2/2023 |

OTHER PUBLICATIONS

Communication pursuant to Article 94(3) EPC for European Patent Application No. 16 740 896.2 dated May 9, 2019. 4 pages.
Communication pursuant to Article 94(3) EPC for European Patent Application No. 16 740 896.2 dated Sep. 21, 2020. 4 pages.
Communication pursuant to Article 94(3) EPC for European Patent Application No. 18206472.5 dated Jan. 7, 2020. 5 pages.
Communication pursuant to Article 94(3) EPC for European Patent Application No. 18206472.5 dated Sep. 16, 2020, 5 pages.
Extended European Search Report for European Patent Application No. 16 74 0896, dated Jun. 6, 2018. 8 pages.
Extended European Search Report for European Patent Application No. 16808519.9, dated Nov. 12, 2018. 9 pages.
Extended European Search Report for European Patent Application No. 18206472.5, dated Jan. 22, 2019. 9 pages.
Extended European Search Report dated Dec. 1, 2020, for EP Application No. 18791954.3, filed on Apr. 27, 2018, 7 pages.
Extended European Search Report dated Jul. 28, 2021, for EP Application No. 18 844 318.8, filed on Aug. 8, 2018, 12 pages.
Extended European Search Report dated Oct. 10, 2022, for EP Application No. 19876942.4, filed on Oct. 25, 2019, 9 pages.
Extended European Search Report dated Oct. 5, 2021 for EP Application No. 18876268.6, filed Nov. 9, 2018, 9 pages.
Final Rejection dated Dec. 12, 2019, from US Application No. U.S. Appl. No. 15/005,341, 34 pages.
Final Rejection dated Feb. 4, 2019, from US Application No. U.S. Appl. No. 15/005,341, 42 pages.
International Application No. PCT/US2018/060104, International Search Report dated Feb. 28, 2019, 14 pages.
International Search Report and Written Opinion for International Application No. PCT/US2022/074985 dated Jan. 6, 2023, 18 pages.
International Search Report dated Oct. 23, 2018, for PCT Application No. PCT/US2018/045793, filed on Aug. 8, 2018, 2 pages.
International Application No. PCT/US2018/029692, International Search Report dated Jul. 12, 2018, 4 pages.
International Search Report and Written Opinion dated Sep. 1, 2016 for PCT Application No. PCT/US2016/037225 filed Jun. 13, 2016. 5 pages.
International Search Report and Written Opinion dated Jan. 15, 2020, for PCT Application No. PCT/US2019/058202, 8 pages.
International Search Report and Written Opinion dated Jun. 15, 2022, for PCT Application No. PCT/US2021/064512, filed on Dec. 21, 2021, 19 pages.
International Search Report and Written Opinion of the International Searching Authority dated Jul. 12, 2018, for PCT Application No. PCT/US2018/029692, 22 pages.

(56) References Cited

OTHER PUBLICATIONS

International Search Report dated Jun. 2, 2016 for PCT/US16/14704. 18 pages.
Non-Final Rejection dated Jun. 3, 2019, from U.S. Appl. No. 15/005,341, 33 pages.
Non-Final Rejection dated Mar. 9, 2018, from U.S. Appl. No. 15/005,341, 15 pages.
Notice of Allowance dated Jan. 18, 2023, for U.S. Appl. No. 16/637,406, filed Feb. 7, 2020, 12 pages.
Notice of Allowance dated Nov. 9, 2022, for U.S. Appl. No. 16/637,406, filed Feb. 7, 2020, 12 pages.
Notice of Allowance dated Aug. 21, 2020, from U.S. Appl. No. 15/005,341, 36 pages.
Notice of Allowance dated Dec. 4, 2020, from U.S. Appl. No. 15/005,341, 7 pages.
Notice of Allowance dated Apr. 5, 2023, for U.S. Appl. No. 17/722,246, filed Apr. 15, 2022, 11 pages.
Partial Supplementary European Search Report dated Apr. 21, 2021, for EP Application No. 18 844 318.8, filed on Aug. 8, 2018, 12 pages.
Resto, Pedro J. et al., "High Speed Droplet-based Delivery System for Passive Pumping in Microfluidic Devices", Sep. 2, 2009, Journal of Visual Experiments, Issue 31, p. 1-5. (Year: 2009).
Written Opinion dated Jun. 2, 2016, for PCT Application No. PCT/US2016/014704, filed on Jan. 25, 2016, 8 pages.
Written Opinion of the International Searching Authority dated Oct. 23, 2018, for PCT Application No. PCT/US2018/045793, filed on Aug. 8, 2018, 10 pages.
Xiaowen Huang et al., "On-Site Formation of Emulsions by Controlled Air Plugs", Small, vol. 10, No. 4, Feb. 1, 2014 (Feb. 1, 2014), pp. 758-765.
Zhu and Wang, "Passive and active droplet generation with Microfluidics: a review" Lab Chip (2017) 17:34-75.

* cited by examiner

FLUIDIC DEVICES WITH REACTION WELLS AND CONSTRICTION CHANNELS AND USES THEREOF

RELATED APPLICATIONS

This application claims the benefit of U.S. Ser. No. 62/751,266 filed on Oct. 26, 2018, which is incorporated by reference in its entirety.

FIELD OF THE DISCLOSURE

This disclosure is generally related to the manipulation of fluids in a microfluidics environment.

BACKGROUND OF THE DISCLOSURE

Fluidic systems can be used to prepare particles, for example microparticles or nanoparticles, for use in a variety of applications such as, but not limited to, new pharmaceutical therapeutic formulations and medical diagnostic products. However, prior fluidic systems for the manufacture of particles, such as nanoparticles have many drawbacks such as inconsistent results, inability to control size, limited productivity, and costly scale-up. Furthermore, such systems require experienced specialists with long training periods and carry significant risk as personnel running the manufacturing process change. Thus, there is a need in the art for microfluidic devices that can be used to produce nanoparticles that are consistent in size and shape, and that have the ability to control size and are easy to use.

Protein production is important in many areas of biotechnology. These include the development and testing of reagents for diagnostics assays and for the production of protein biologics. Such methods can include a protein precipitation step. However, methods for precipitating proteins can be difficult to perform consistently in large scale, require incubation periods, and can damage precipitated proteins, especially at high concentrations of precipitates. Thus, there is a need in the art for fluidic devices that can be used to precipitate proteins quickly, consistently and that can be effectively scaled up.

SUMMARY OF THE DISCLOSURE

This disclosure provides fluidic devices that are useful in the production of particles, such as microparticles and nanoparticles, and protein precipitates. Furthermore, some devices provided herein are useful for the detection of precipitate reaction products.

In some aspects, this disclosure provides a fluidic device that comprises a first port; a first fluid transport channel in direct fluid communication with the first port, a reaction well; an overflow channel; a second fluid transport channel in direct fluid communication with the overflow channel; a fluidic constriction channel in direct fluid communication with the reaction well and the second fluid transport channel; and, a second port in direct fluid communication with the second fluid transport channel (e.g., as illustrated in FIGS. 1, 2, and 10-14A), or a fluidic device assembly comprising at least two of such microfluidic devices, or comprising other microfluidic devices provided herein, including in parallel or in serial. In illustrative embodiments, methods for using such fluidic devices to produce particles are provided.

In another aspect, as illustrated in a non-limiting exemplary manner in FIG. 15, provided herein is a device sometimes referred to herein as a device for detecting a reaction product, that comprises a first port 1; a first fluid transport channel 1A, optionally having a relatively straight or straight section 1A1 and an optionally rounded section 142; a reaction well 2; a fluidic constriction channel 4; a passive pressure sensing channel 3A; a second port 3; a second fluid transport channel 5A; a third fluid transport channel 5A, an interface channel segment 5C and, a third port 6. In one illustrative embodiment, as illustrated in a non-limiting exemplary manner in FIG. 15, the second fluid transport channel 5A is in direct fluidic communication with the first fluid transport channel 1A at an end of the first fluid transport channel opposite the first port; the fluidic constriction channel 4 is in direct fluidic communication with the reaction well 2 and an interface channel segment 5C directly connecting the second fluid transport channel 5A and the third fluid transport channel 5B, wherein the width of the interface channel segment is typically identical to the width of the fluid transport channel to which it is directly connected; the reaction well 2 is in direct fluidic connection with the passive pressure sensing channel 3A at an end of the passive pressure sensing channel opposite the second port 3; the passive pressure sensing channel 3A extends from the reaction well 2 opposite the fluidic constriction channel 4 and terminates at the passive pressure sensing channel port 3; and the first fluid transport channel 1A is not in direct fluidic communication with the reaction well 2.

In another aspect, provided herein, is a method for detecting a reaction product, which in illustrative embodiments uses a device for detection of a reaction product as provided herein, as a non-limiting example, the fluidic device discussed in the preceding paragraph.

This Summary section is not intended to limit the scope or breadth of the current disclosure. Further details regarding aspects and embodiments of the present disclosure are provided throughout this patent application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A. Step one: introduction of first fluid into fluidic device to fill reaction well 2 (solid coloring representing the first fluid (e.g., organic solvent solution comprising dissolved lipids or polymer solution); FIG. 2B. Step two: removal of first fluid (e.g., organic solvent solution comprising dissolved lipids or polymer solution); FIG. 2C: Step three: introduction of second fluid (e.g., aqueous buffer or water-soluble synthetic polymer solution) into fluidic device to mix with first solution thereby producing nanoparticles.

FIG. 16A shows initial introduction of a first fluid into the device through the first port 1. FIG. 16B shows further filling of the device, partially filling the reaction well 2 and third fluid transport channel 5B. FIG. 16C shows complete filling of the reaction well 2 with first fluid and partial filling of the third fluid transport channel 5B.

FIG. 17A: The first fluid fills most of the device as depicted in FIG. 16C. FIG. 17B: A negative pressure is applied to the first port 1, causing the first fluid to begin to recede from the device towards the first port 1. The geometry and dimensions of the reaction well 2, passive pressure sensing channel 3A, fluidic constriction channel (not numbered here but the part corresponding to 4 in FIG. 15) and fluid transport channels (5A, 5B, 5C, and 1A) prevents fluid in the reaction well 2 from leaving the device. FIG. 17C. Due to the design of the device, a small volume of first fluid has been captured in the reaction well 2. At this stage using this device embodiment, essentially no other parts of the device retain any fluid (i.e. the rest of the device is empty).

FIG. 18A: A second fluid (e.g. human sweat) enters the device with reaction well 2 filled with test solution from the third port 6 via positive applied pressure, and enters the third fluid transport channel 5B. Not illustrated as a separate figure, fluid from the second fluid reaches the reaction well 2, where it interacts with the captured first fluid. Top right panel FIG. 18B: Fluid from the second fluid continues to flow through the device towards the first port 1 where it exits the device. FIGS. 18A and 18D depict precipitate development in the device illustrated in FIG. 15. FIG. 18C: As second fluid (e.g., sweat) mixes with first fluid (e.g. anti-perspirant test compound) in the opening of the reaction well at or near the interface channel segment 5C, a precipitate begins to form. FIG. 18D: Precipitate PPT continues to grow the entire length of the second fluid transport channel 5A. as more second fluid flows into the device and interacts with first fluid. Precipitate grows until it eventually blocks the second fluid transport channel, inhibiting incoming flow.

FIG. 22A is a graph showing the effective diameter and polydispersity index (PDI) of four batches (Formulation Number 1-4) of liposomes formulated in the device and analyzed by DLS. FIG. 22B is a graph showing the effective diameter/size and polydispersity index (PDI) of liposomes generated with identical input first liquid and second liquid, but different flow rates.

FIG. 23A is a graph showing the effective diameter and polydispersity index (PDI) of three batches (Formulation Number 1-3) of liposomes that were made using the device and analyzed by DLS. FIG. 23B is a graph showing the effective diameter and PDI of liposomes generated holding all parameters constant, but inputting a first fluid and second fluid at different flow rates. FIG. 23C is a graph showing the effective diameter and PDI of liposomes generated with identical input first fluid and second fluid, but different flow rate ratios of an input stream of the first fluid to an input stream of the second fluid. FIG. 23D is a graph showing the effective diameter and PDI of liposomes collected at different points during the process of flowing 1 L of combined first fluid and second fluid through the fluidic device.

FIG. 24A is a graph showing the effective diameter and polydispersity index (PDI) of four batches (Formulation Number 1-4) of liposomes formulated in the device and analyzed by DLS. FIG. 24B is a graph showing the effective diameter and PDI of liposomes generated with identical input first fluid and second fluid, but different flow rates. FIG. 24C is a graph showing the effective diameter and PDI of liposomes generated with identical input first fluid and second fluid, but different flow rate ratios of an input stream of the first fluid to an input stream of the second fluid.

DETAILED DESCRIPTION OF THE INVENTION

Disclosed herein are fluidic devices that in illustrative embodiments, can be used to make nanoparticles or protein precipitates, or to monitor precipitate formation. The devices include highly efficient mixing that is partially responsible for providing the devices the ability to solve numerous problems in the art. The fluidic devices are easy to use and provide consistent results from batch to batch and within a batch. Furthermore, exemplary embodiments of fluidic devices provided herein can be used to produce particles, for example nanoparticles, with the ability to control particle size and can be used for straightforward scale-up from microliters to liters, with consistent results and an optional continuous flow process. In addition, exemplary embodiments of fluidic devices provided herein can be used to produce protein precipitates that allow for continuous precipitation of proteins without the need for an incubation period and that can be used to produce protein precipitates of lower concentrations than traditional batch incubation/agitation methods, thus reducing the chance for undesirable structural changes in precipitated proteins of interest.

A "fluidic device" of this disclosure is a device through which one or more fluids can be transported and/or moved through the same. The movement of the one or more fluids can be, for instance, through passages formed within and/or upon such a device. Illustrative fluidic devices of this disclosure are illustrated in FIGS. 1, 2, 10-14A, 15-19, 20, 21, and 26. In some embodiments, the fluidic device can be a millifluidic, microfluidic, nanofluidic, or picofluidic device in which the amount of fluids within, stored within or moving within said device can be in milliliter, microliter, nanoliter, and/or picoliter amounts. Thus, in some embodiments, the reaction well is configured to hold milliliters (ml) of a fluid. In other embodiments, the reaction well is configured to hold microliters (μl) of a fluid. In other embodiments, the reaction well is configured to hold nanoliters (nl) of a fluid. In other embodiments, the reaction well is configured to hold picoliters (pl) of a fluid. As such, a fluidic device presented herein can be a millifluidic, microfluidic, nanofluidic, or picofluidic device. In illustrative embodiments, the fluidic device is a microfluidic device.

Figure 1:
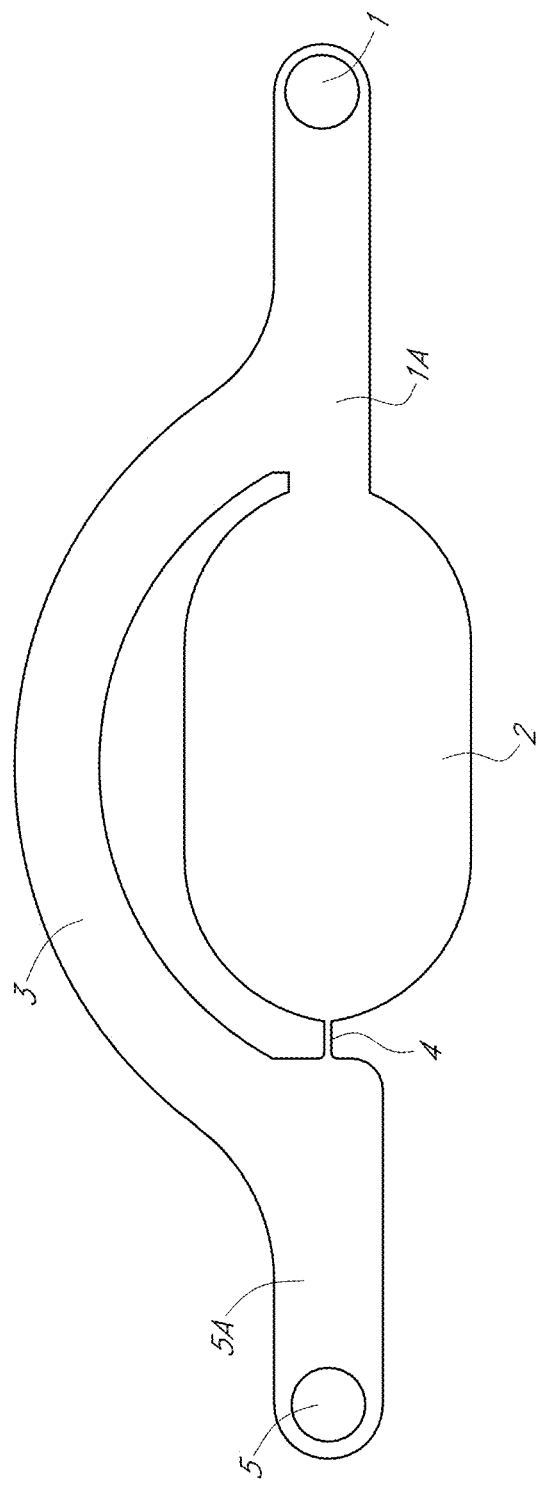
FIG. 1 illustrates an exemplary fluidic device that can be used to produce nanoparticles. This exemplary fluidic device is composed of a first port (part 1), first fluid transport channel (part 1A), reaction well (part 2), overflow channel (part 3), fluidic constriction channel (part 4), second fluid transport channel (part 5A), and second port (part 5).

The fluidic devices described herein typically comprise multiple parts or regions therein through which fluids can move and/or in which fluids can be stored and/or manipulated. Channels and other parts (e.g. reaction wells) that are in fluidic communication, can be called a fluidic circuit herein. Parts and/or regions within fluidic devices and fluidic circuits herein, can include, for example, one or more ports, one or more air valves (e.g., associated with or connected to a port), one or more channels that can form a fluidic connection, one or more high resistance air valve constriction channels, one or more reaction wells, one or more overflow channels, one or more pressure sensing channels, and one or more fluid transport channels. Where a high resistance air valve constriction channel is present in the fluidic device, it is typically positioned upstream (relative to movement of air or fluid through the fluidic device) of the fluidic connection. In some embodiments, the fluidic device also includes one or more inlets and/or outlets (e.g., ports) that may perform as an inlet, an outlet, or both. The different parts and/or regions typically communicate with one another either directly or indirectly with respect to fluids moving through the same (e.g., the parts or regions are in "fluid connection," "fluid communication" or "fluidic communication" with one another (e.g., the parts or regions "fluidly communicate" with one another)). Direct communication between parts and/or regions means that a fluid moves directly from one part or region to another without passing through an intermediary part or region, which can be referred to herein as "direct fluidic communication". For instance, as shown in FIG. 1, fluidic constriction channel 4 is in direct fluidic communication with reaction well 2, and fluid transport channel 5A. Indirect communication, in contrast, means that fluid moves from one part or region to another through an intermediary part or region, referred to herein as "indirect fluidic communication," "indirect fluid communication," or "indirect fluid connection." For example, referring to FIG. 1, reaction well 2 is in indirect fluidic communication with fluid transport channel 5A as the two parts or regions are each directly connected to fluidic constriction channel 4 but not to one another. Similarly, the parts of the fluidic device illustrated in FIG. 15 may also be arranged to be in fluidic communication with one or more other parts of such a fluidic device.

Figure 12A:
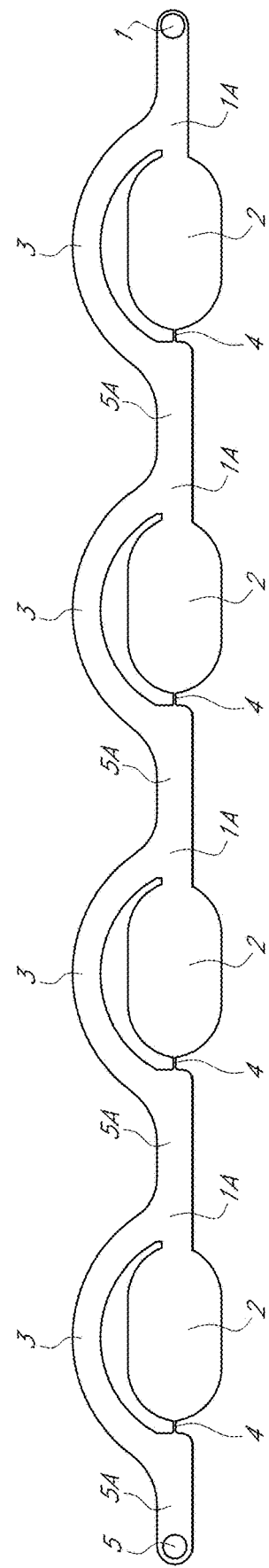
FIG. 12A illustrates an exemplary fluidic device in which multiple fluidic device subunits are connected in series, wherein the first fluid transport channel 1A of one device in the series is continuous with the second fluid transport channel 5A of the next device in the series.
Figure 12B:
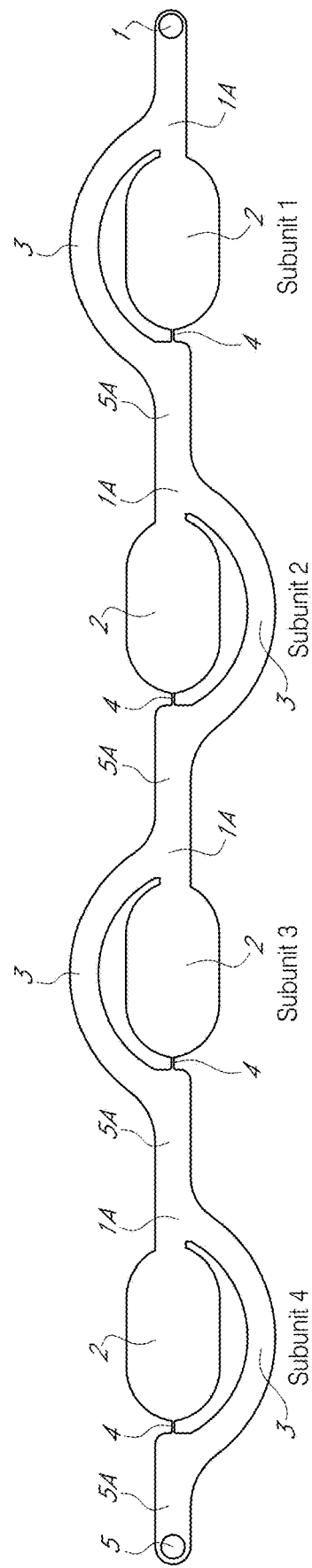
FIG. 12B illustrates an exemplary fluidic device in which multiple fluidic device subunits are connected in series, wherein the first fluid transport channel 1A of one device in the series is continuous with the second fluid transport channel 5A of the next device in the series, but wherein the overflow channels 3 of each subunit are on the opposite side of at least two, but optionally each, successive fluidic device subunit.

Individual fluidic devices can also be connected to one another in a series, which sometimes can be referred to herein as a "fluidic system," a "fluidic assembly," or a series of microfluidic device subunits. Examples of multiple fluidic devices or device subunits connected to one another in series are shown in FIGS. 12A, 12B, 14A, 20, 21A, and 26. In such embodiments, each fluidic device can be attached to one another though a fluid transport channel. For instance, FIG. 12A shows a first fluidic device connected to a second fluidic device through fluid transport channels 5A and 1A, which collectively can be referred to as "intradevice fluid transport channel". In such embodiments, the second fluid transport channel of the first fluidic device (e.g., 5A in FIG. 12A) can be considered "continuous with" the first fluid transport channel of the second fluidic device (e.g., 1A of FIG. 12A). In such embodiments, the fluid transport channels are typically in direct fluidic communication with one another. In some embodiments, a fluidic device can include multiple fluidic devices, also referred to in such configurations as fluidic device subunits, connected in series, wherein the first fluid transport channel of a device in a series is continuous with the second fluid transport channel of the next device in the series (e.g., 1A and 5A as illustrated in FIGS. 12A and 12B). In some embodiments, the reaction well of some of the or each fluid transport channel(s) can be in fluid communication with an air control valve.

The fluidic devices described herein typically include a "fluidic constriction channel" (part 4 in figures that illustrate a microfluidic device) in direct fluidic communication with reaction well and a fluid transport channel. As illustrated herein, and discussed in more detail, a fluidic constriction channel 4 typically has a smaller diameter or width than a diameter or width of the reaction well and an overflow channel in the same fluidic device, or fluidic device subunit in embodiments that include a fluidic device comprising more than one fluidic device subunit. As a result, a "fluidic constriction channel" has a size and shape relative to a reaction well and overflow channel of the same fluidic device, or the same fluidic device subunit for fluidic devices comprising more than one fluidic device subunits, that makes the fluidic device capable of, operable to, effective for, and adapted to retain fluid for a longer time period in the reaction well as fluid is introduced into the fluidic device, for example when the volume of fluid introduced into the fluidic device exceeds the combined capacity of its channels and wells. In certain embodiments, the fluidic constriction channel has a size and shape relative to a reaction well and overflow channel of the same fluidic device, or the same fluidic device subunit for fluidic devices comprising more than one fluidic device subunits, to retain fluid in the reaction well when liquid is removed from the fluidic device. For example, because of the relatively small width or diameter of the fluidic constriction channel relative to other components, as provided in this paragraph and elsewhere herein, the fluidic device can retain fluid in a reaction well and the fluidic constriction channel when a negative pressure is applied through a first port 1 of a microfluidic device or microfluidic device subunit that is full of fluid. In certain microfluidic devices herein, such as those of FIG. 1 and FIG. 20, the fluidic constriction channel is directly connected to reaction well 2 opposite a first fluid transport channel 1A, and has a smaller diameter or width, typically less than one-fifth and in some embodiments less than one-sixth, one-seventh, one-eighth, one-ninth, or one-tenth the diameter or width of each of the following components: the first fluid transport channel 1A, the reaction well 2, a second fluid transport channel 5A, directly connected to the fluidic constriction channel 4 opposite the reaction well 2, and an overflow channel 3 that connects the first fluid transport channel 1A to the second fluid transport channel 5A as provided herein.

Figure 20:
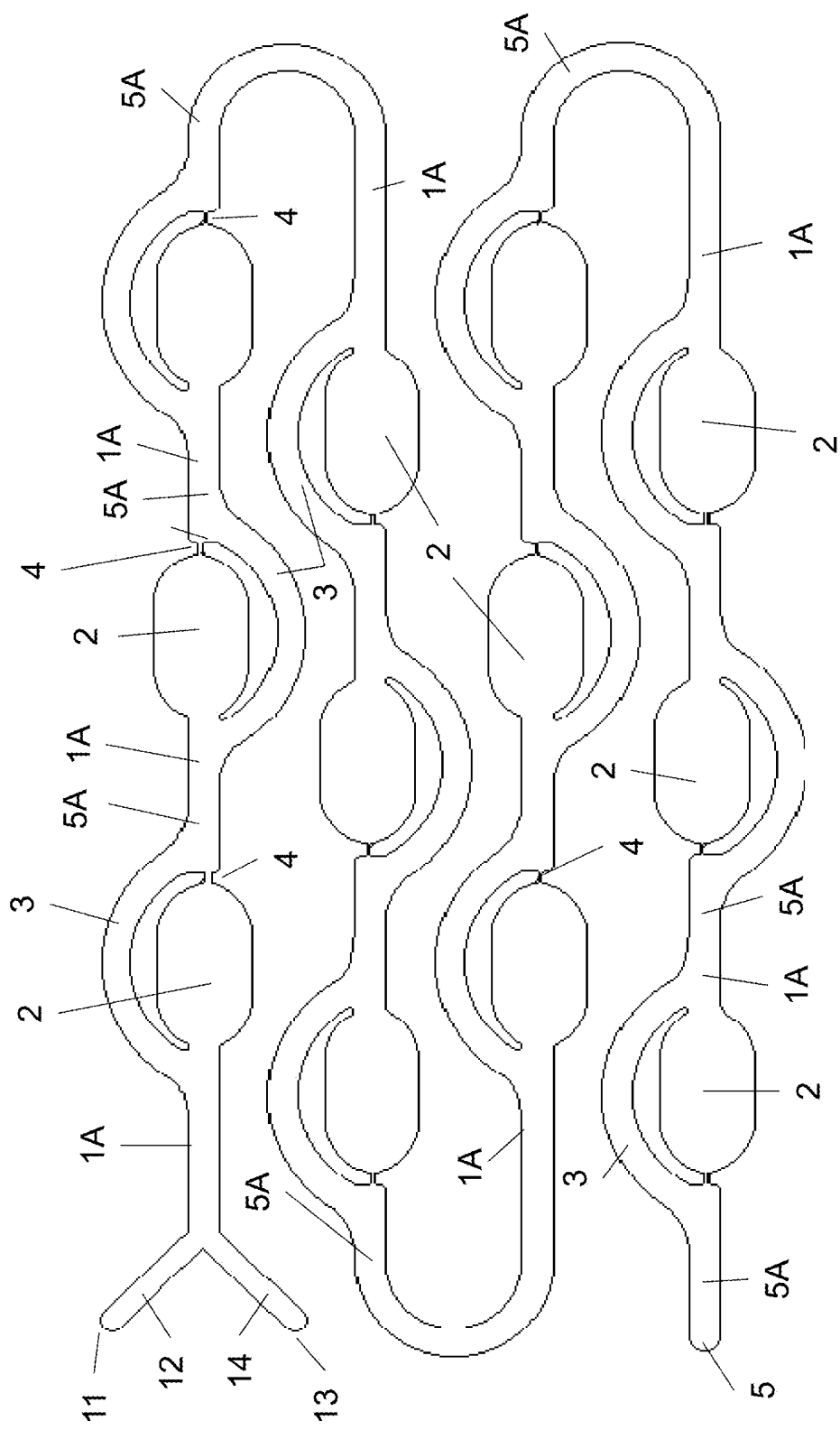
FIG. 20 illustrates a further exemplary embodiment of a fluidic device comprising multiple fluidic device subunits in series, with two inlet channels (12, 14) having associated separate inlet ports (11 and 13, respectively) that form a Y junction in fluid communication with the first fluid transport channel 201A of the first fluidic device in the series of fluidic devices. The microfluidic device shown in FIG. 20, as a non-limiting example, include 12 microfluidic device subunits as 4 rows of 3 microfluidic device subunits each, with each microfluidic device subunit connected in a series. As demonstrated in the Examples herein, the design in FIG. 20 was used to prepare a device with small dimensions relative to a device with larger dimensions (Table 1). The device with small dimensions (Table 1) functions the same as the design with large dimensions but is capable of forming smaller nanoparticles due to its reduced dimensions as provided in the Examples herein.
Figure 21A:
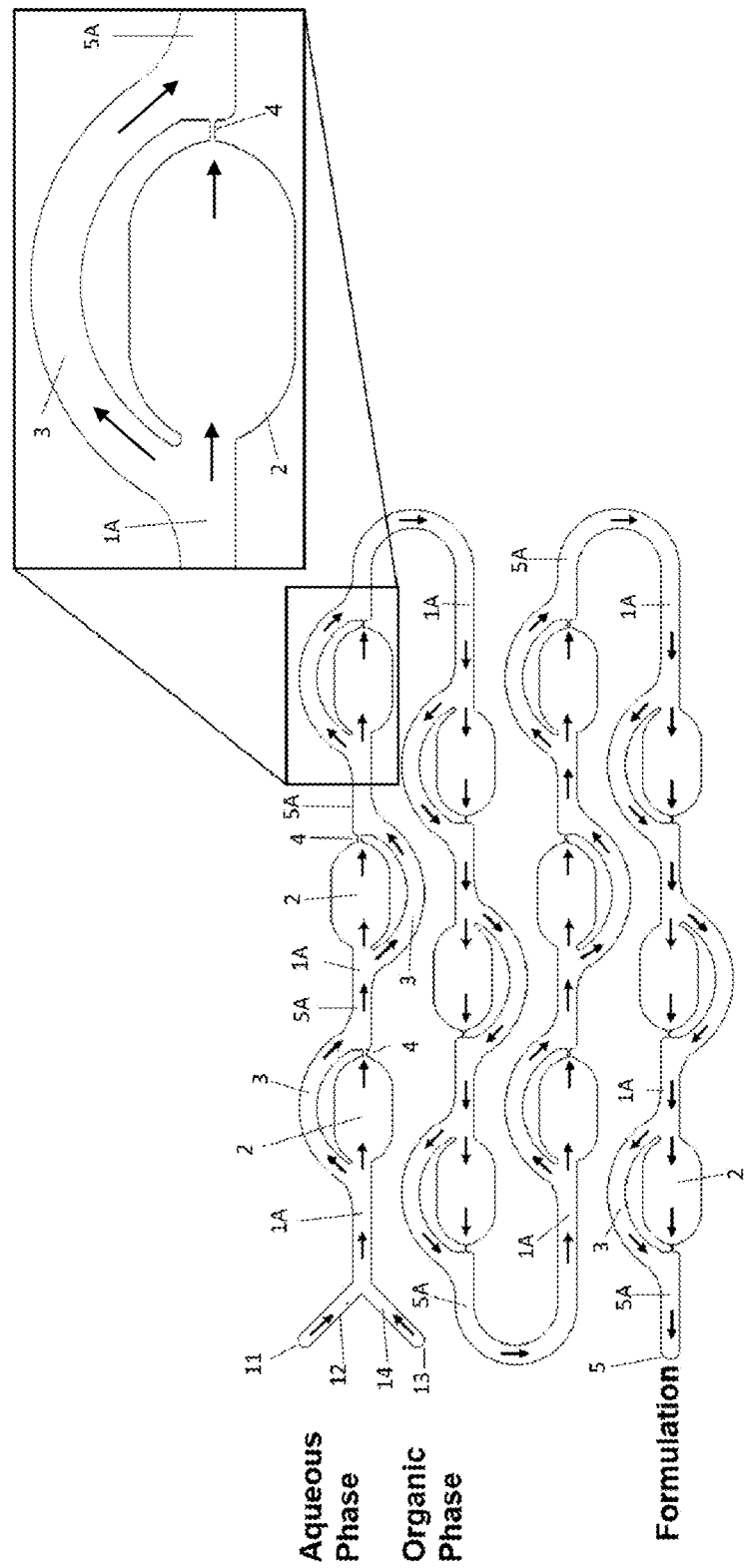
FIGS. 21A and 21B illustrate microfluidic flow (FIG. 21A) and mixing (FIG. 21B) within an exemplary microfluidic device similar in design to the microfluidic device of FIG. 20. An increased magnification view of one of the microfluidic devices is shown in the inset of FIG. 21A. A representative image of microparticles produced using such a device is shown in the inset of FIG. 21B, with the bar representing 1,000 nm.
Figure 21B:
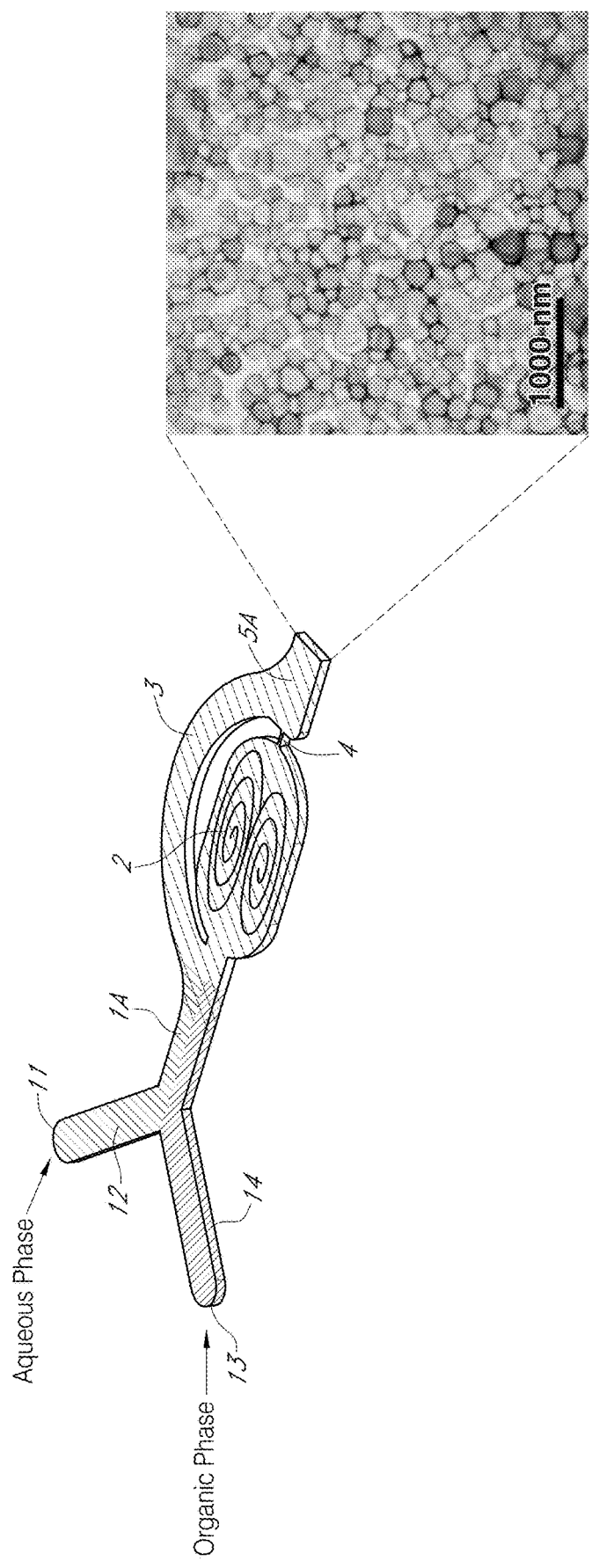

This relatively smaller width or diameter of the fluidic constriction channel 4 compared to these other components listed in the preceding sentence, in embodiments such as those of FIG. 20 and FIGS. 21A and 21B, where 2 (as illustrated), 3, 4, or more input fluids are introduced into the microfluidic device each through different ports such as 11 and 13 (and optionally additional ports) (such fluidic devices having at least a first and second inlet port (also called an input port herein), such as first and second port channel ports, sometimes called coflowing fluidic devices herein), a relative configuration of the fluidic constriction channel 4 compared to these other components keeps fluids that enter a reaction well 2, within the reaction well 2 for a longer period of time to effectively mix the input fluids, as illustrated in FIG. 21B. Thus, in such embodiments the size and configuration of the fluidic constriction channel relative to the first fluid transport channel 1A, the reaction well 2, the second fluid transport channel 5A, and the overflow channel 3 within the same fluidic device, are such that the device is capable of, operable to, or adapted to effectively, or more effectively mix a first fluid and a second fluid entering the device through different ports connected to the same reaction well through a channel. Not to be limited by theory, the difference in widths (which is directly a difference in hydrodynamic resistances) between different parts of fluidic devices herein, for example between the fluidic constriction channel 4 and the other parts listed above, causes a differential pressure drop at any two regions where smaller and larger channels meet, for example where the reaction well 2 and the fluidic constriction channel 4 meet. This causes recirculating vortices to form, which in turn transforms a streamlined laminar flow into an unstable flow, thus providing effective mixing. This unstable flow in illustrative embodiments, is not "turbulent", and thus makes fluidic devices herein that have such structure, designed to, operable to, capable of, and adapted to transform, or effective for transforming, an input laminar flow fluid stream into an unstable flow, but in illustrative embodiments not a turbulent flow. Furthermore, these properties thus makes fluidic devices herein that have such structure and are used to make particles (e.g. microfluidic devices that are used to make microparticles or nanoparticles), effective for controlling particle size and adapted to control particle size, gives them the ability to control particle size, and makes them operable to control particle size. Such effective or more effective mixing results in relatively uniform, or more uniform particle sizes. A skilled artisan will recognize that turbulent flow is dictated by a dimensionless number: Reynolds Number (ratio of inertial to viscous forces). Flows below Re of 2100 are usually accepted as laminar and above it is turbulent. Illustrative embodiments of fluidic devices herein are effective for, adapted to, capable of, and operable to achieve a Re of less than 2000, less than 1500, less than 1000, or in further illustrative embodiments, less than 500. It is noteworthy that "fluidic constriction channel" 4 can be referred to herein as "fluid constriction channel", "fluid connection channel", fluid connection channel (bridge)", fluidic connection channel", fluidic connection channel (bridge)", or "fluidic connection bridge".

The "reaction well" is typically a compartment or region (e.g., a depression) of the fluidic device into which in illustrative embodiments a first fluid (i.e. liquid) (e.g. an initial reagent (e.g., lipids in an organic solvent or a protein)) can be mixed with a second, third, fourth, or more fluid, or in which two or more fluids that are simultaneously input into a device herein are retained for longer periods than those traveling through an overflow channel, such that they can mix, or in which a first fluid can be stored until a second fluid is flowed into the device for example to mix in the reaction well or to interact with a fluid in the reaction well and fluidic constriction channel. In some embodiments, the shape of the reaction well is configured for production of a particular particle size, or precipitate detection reaction. A reaction well can have many different shapes and configurations, for example any of the following shapes: angular, square, rectangular, trapezoidal, circular, triangular, and/or the like such as cylindrical. Exemplary reaction wells, and shapes thereof include part 2 in figures herein that illustrate a fluidic device. In some embodiments, a device herein comprises a reaction well configured to hold, contain, or retain, operable to hold, contain, or retain, capable of retaining, adapting, or holding, or adapted to hold, contain, or retain a volume between 100 pl and 10 ml, between 1 nl and 10 ml, between 1 µl and 10 ml, between 1 nl and 10 ml, between 1 µl and 450 µl, between 5 nl and 15 nl, between 15 nl and 35 nl, between 100 nl and 1 ml, between 100 nl and 100 µl, between 1 µl and 1 ml, between 5 µl to 30 µl, between 10 µl and 1 ml, between 1 µl and 500 µl, between 10 µl and 500 µl, between 10 µl and 250 µl, between 10 µl and 200 µl, between 10 µl and 100 µl or between 10 µl and 50 µl, or about 10 µl.

An "overflow channel" of any of the fluidic devices described herein provides a path through which fluid flows around a reaction well. The overflow channel(s) is typically connected to, and in illustrative embodiments in direct fluidic communication with a fluid transport channel and/or reaction well as shown for example in FIG. 1 (e.g., overflow channel 3) or FIG. 10 (overflow channel 3). An overflow channel typically follows a rounded shape around at least a portion of a reaction well, and thus provides a rounded path for fluid that does not enter the reaction well, for example if fluid is input into a device in excess of the volume of the reaction well, to flow around the reaction well.

A fluid transport channel such as for example, parts 1A and 5A of any of the figures herein that illustrate a fluidic device is a channel through which fluids move in a fluidic device herein, typically between a port, an overflow channel, a reaction well, and/or a fluidic constriction channel. Accordingly, such fluid transport channels can be in direct fluidic communication with, for instance, a reaction well and/or an overflow channel. Such fluid transport channels can alternatively be in direct fluidic communication with, for instance, an overflow channel and a fluidic restriction channel. Such fluid transport channels can also be connected to one or more ports through which fluid can enter or exit the fluid transport channel. An "intradevice transport channel" can be a fluid transport channel formed between devices or device subunits that are connected to one another (e.g., in fluidic communication with one another) for example in series.

Fluidic devices provided herein in certain illustrative embodiments comprise an "air control valve" which is a valve through which air can enter or leave the fluidic device.

In some embodiments, such a valve can allow air to move into, or alternatively out of, the fluidic device when open to the surrounding atmosphere. In illustrative embodiments, an air control valve can be used to control which reaction well(s) are filled with a fluid that is introduced into a fluidic device, in a series of microfluidic device subunits that include such reaction wells. This control is accomplished by independently opening or closing an air control valve connected to a reaction well as described in the International Patent Application publication WO 2018/200896 A1). In some embodiments, such as those illustrated in FIG. 15, the pressure sensing channel can function similarly to the passive air control valve.

Devices herein can be used to move and manipulate fluids, as non-limiting examples for the production of particles, for the production of protein precipitates, or to detect precipitate formation. Thus, fluids input into fluidic devices herein have various compositions and can include, but are not limited to a fluid for the production of particles, a sample, such as a protein sample or a test deodorant sample, a protein precipitant, one or more buffers, water, and/or one or more wash solutions. In some embodiments, the fluid may be air but the term fluid is typically used herein to indicate a liquid. Air is therefore typically referred to as such. Those of ordinary skill in the art will understand that many different types of fluids can be suitable for use with the fluidic devices described herein. For example, for the manufacture of particles, such as microparticles or nanoparticles, suitable fluids can be those known for such manufacture, for example an organic solvent, typically including one or more lipids, a polymer solution, water, or one or more aqueous buffers. In some embodiments, a pocket of air can be introduced between a fluid or fluids, producing an "air plug". In some embodiments, the fluid between air plugs can be referred to as a "fluidic slug". The same or different fluids can also be introduced into the same or different ports during operation of the fluidic device, as discussed further herein.

In some embodiments, this disclosure provides a fluidic device that includes a first port; a first fluid transport channel in direct fluid communication with the first port, a reaction well; an overflow channel; a second fluid transport channel in direct fluid communication with the overflow channel; a fluidic constriction channel in direct fluid communication with the reaction well and the second fluid transport channel; and, a second port in direct fluid communication with the second fluid transport channel. Illustrative embodiments of such fluidic devices are shown, for example, in FIGS. 1, 2A-2C, and 10-11 as single fluidic devices, and FIGS. 12-14A, 20, 21, and 26 as multiple similar or identical interconnected fluidic devices (i.e. fluidic device subunits) and include a first port (part 1), first fluid transport channel 1A, reaction well 2, overflow channel 3, fluidic constriction channel 4, second fluid transport channel 5A, and second port 5, and optional pillars 7 in FIG. 10. Exemplary size ranges for each part of such a fluidic device (subunits of a fluidic device comprising multiple fluidic devices) is provided in Table 1, as well as sizes of non-limiting exemplary devices of FIGS. 1 and 20. It is noteworthy with respect to Table 1 and the dimensions provided for FIG. 20 that the provided measurements for the first fluid transport channel refers to the fluidic channel 201A between the inlet channels 12 and 14 and the first reaction well, the third fluid transport channel refers to the channels linking two wells in a series (labeled as parts 5A and 1A), which can also be referred to as intradevice transport channels, and the second fluid transport channel refers to channel 205A which is the channel of the final microfluidic device subunit in the series that is in direct fluidic communication with the outlet (i.e. second port 5). The heights (or diameters) of the various parts are the same, but in some embodiments the heights may differ (in some embodiments, e.g., the height of the fluidic constriction channel can be from 50-500 µm while the height of the other parts can range from 100-2,000 µm). The dimensions shown in Table 1 can be applied to such fluidic devices but can also be modified within the non-limiting exemplary indicated ranges to fit the user's needs. As will be understood by those of ordinary skill in the art, a variety of combinations of heights, depths, widths (or diameters in the case of a circular channel), and lengths may be used for each part in the device to achieve desired functionality. In illustrative embodiments, the fluidic devices are used to make particles, such as microparticles or nanoparticles, to make protein precipitates. In further embodiments of these illustrative embodiments, as well as other embodiments, fluidic devices provided herein can include an air control valve, but in certain embodiments do not include an air control valve.

TABLE 1

| Design Feature | Measurements Exemplary device of FIG. 1/FIG. 20 (large)/FIG. 20 (small) | Measurements Non-limiting exemplary ranges |
| --- | --- | --- |
| Design height | 500 µm/300 µm/300 µm | 100-2000 µm, 100-500 µm, 200-400 µm, or 300-500 µm for all parts except fluidic constriction channel: 50-500 µm |
| First fluid transport channel | Length: 5900 µm/5900 µm/2360 µm Width: 1200 µm/1300 µm/520 µm | Length: 1000-10000 µm, 2000-7500 µm, or 2000-10000 µm Width: 300-2300 µm, 400-2000 µm, 300-1500 µm, or 1000-2000 µm |
| Overflow channel | Length: 10900 µm/10900 µm/4360 µm Width: 1200 µm/1200 µm/480 µm | Length: 3000-15000 µm, 4000-12500 µm, or 8000-15000 µm Width: 300-2300 µm, 400-2000 µm, 300-1500 µm, or 1200-2000 µm |
| Second fluid transport channel | Length: 5460 µm/4500 µm/1800 µm Width: 1500 µm/1300 µm/520 µm | Length: 500-10000 µm, 500-5000 µm, or 2000-10000 µm Width: 300-2300 µm, 400-2000 µm, 300-1500 µm, or 1000-2000 µm |
| Reaction well | Length: 7460 µm/7000 µm/2800 µm Width: 4000 µm/4000 µm/1600 µm | Length: 1000-13000 µm, 1000-10000 µm, 2500-10000 µm, or 5000-12000 µm Width: 1000-7000 µm, 1500-5000 µm, or 3000-6000 µm |
| Fluidic constriction channel | Length: 500 µm/500 µm/200 µm Width: 100 µm/100 µm/80 µm | Length: 100-1000 µm or 200-1000 µm Width: 10-500 µm, 25-250 µm, or 50-200 µm |
| Third/Intradevice fluid transport channel | Length: N/A/3000 µm/1200 µm Width: N/A/1300 µm/520 µm | Length: 5000-10000 µm or 1000-7500 µm Width: 300-2300 µm, 400-2000 µm, 300-1500 µm, or 1000-2000 µm |

In some embodiments, the fluidic device for producing a reaction product such as particles or a protein precipitant can be adapted to, configured to, and operable to regulate the mixing process of a first fluid trapped in the reaction well and a second fluid that washes through the device, for example after the second fluid is delivered into the device via a syringe pump. For example, any number of pillars can be used and positioned as desired in the reaction well 2. In illustrative embodiments, one or more pillars may be positioned in the reaction well 2 proximal to (i.e., nearer to) the junction between the reaction well 2 and the fluid connection 4, or proximal to (i.e., nearer to) the junction between the reaction well 2 and the first fluid transport channel 1A. Thus, in some embodiments, the reaction well 2 comprises: a) a first opening leading to fluidic constriction channel 4 and a second opening leading to the first fluid transport channel 1A, and wherein the at least one pillar is positioned: i) distally to the first opening and proximally to the second opening; ii) distally to the second opening and proximally to the first opening; or iii) central to the first and second openings; b) at least two, three, four, five, six, seven, eight, nine, 10, 11, 12, 13, 14, 15 or 16 pillars; and/or, c) three pillars positioned distally to the first opening and proximally to the second opening; three pillars positioned distally to the second opening and proximally to the first opening; or, an even number of pillars positioned in pairs distributed between the first and second openings. For instance, in one illustrative embodiment, six pairs of 100 µm-diameter pillars (made of the same material as at least most of the other parts of the fluidic device) were essentially evenly distributed within the reaction well 2 (FIG. 10, pair closest to the fluidic constriction channel 4 being labeled part 7). In another illustrative embodiment, the shape of the reaction well was changed slightly (FIG. 11) by reducing the curvature of the well on one side to alter flow patterns inside the well. Other variations on the basic design and these modifications may also be suitable as can be determined by those of ordinary skill in the art.

In some embodiments, the fluidic device for producing a reaction product such as particles and/or a protein precipitant can comprise a first port; a first fluid transport channel in direct fluid communication with the first port, a reaction well; and, an overflow channel; a second fluid transport channel in direct fluid communication with the overflow channel; a fluidic constriction channel in direct fluid communication with the reaction well and the second fluid transport channel; and, a second port in direct fluid communication with the second fluid transport channel; wherein: the overflow channel 3 has a length of between 8,000 and 15,000 µm, in illustrative embodiments about 10,900 µm; the fluidic constriction channel 4 has a width or diameter of 50-500 µm, in illustrative embodiments 50-250 µm, or about 100 µm; optionally the reaction well 2 comprises one or more of one or more lipids, an organic solvent, an alcohol, acetonitrile, one or more polymers, an aqueous buffer, a mixture thereof, and/or nanoparticles in solution; and/or, optionally the reaction well 2 comprises at least one pillar, optionally having a diameter of 50-250 µm, 50-150 µm or about 100 µm, wherein each pillar is the same or different from any other pillar and optionally has a circular, triangular, or rectangular shape; the ratio of resistance between the reaction well and overflow channel is 0.067-1, 0.2 to 0.5, 0.2 to 0.3, or 0.25; the ratio of resistance between the overflow channel and fluidic constriction channel is 0.2-12.5, for example about 1.5 to 5, or for example 1.82; and/or, each channel is essentially circular, oval, rectangular or trapezoidal in shape, or a mixture of the same. In some embodiments, a fluidic device for producing particles, for example nanoparticles, can comprise a first port, a first fluid transport channel 1A in fluid connection with a first port 1, a reaction well 2, an overflow channel 3, a fluidic constriction channel 4; and, a second fluid transport channel 5A in fluid connection with a second port 5; wherein: the first fluid transport channel 1A is in direct fluidic communication with the overflow channel 3 and the reaction well 2; the overflow channel 3 is further in direct fluidic communication with the second fluid transport channel 5A and the fluidic constriction channel 4; and, the fluidic constriction channel 4 is in direct fluid communication with the reaction well 2 and the overflow channel 3; wherein: the overflow channel 3 has a length of between 8,000 and 15,000 µm, optionally about 10,900 µm; the fluidic constriction channel 4 has a width or diameter of 50-1000 µm, optionally about 100 µm; optionally the reaction well 2 comprises one or more of one or more lipids, an organic solvent, an alcohol, acetonitrile, a polymer, an aqueous buffer, a mixture thereof, and/or nanoparticles in solution; optionally the reaction well 2 comprises at least one pillar, optionally having a width or diameter of about 100 µm, wherein each pillar is the same or different from any other pillar and optionally has a circular, triangular, or rectangular shape; the ratio of resistance between the reaction well and overflow channel is 0.067-1, optionally about 0.2 to 0.5; the ratio of resistance between the overflow channel and fluidic constriction channel is 0.2-12.5, optionally about 1.5 to 5; and/or, each channel is essentially circular, oval, rectangular or trapezoidal in shape, or a mixture of the same. In some embodiments, a fluidic device useful for producing nanoparticles (e.g., a fluidic device illustrated in FIGS. 1, 10-14A, and 21B) can have a height of about 300 µm to about 500 µm, in an illustrative embodiment about 500 µm; a first fluid transport channel 1A has a length of from about 2000 µm to about 10,000 µm, in the illustrative embodiment about 5900 µm, and/or a width or diameter of about 1000 µm to about 2000 µm, in the illustrative embodiment about 1200 µm; an overflow channel 3 has a length of from about 8000 µm to about 15,000 µm, in the illustrative embodiment about 10,900 µm, and/or a width or diameter of about 1200 µm to about 2000 µm, in the illustrative embodiment about 1200 µm; a second fluid transport channel 5A has a length of from about 2000 µm to about 10,000 µm, in the illustrative embodiment about 1500 µm, and/or a width or diameter of about 1000 µm to about 2000 µm, in the illustrative embodiment about 1500 µm; a reaction well 2 has a length of from about 5000 µm to about 12,000 µm, in the illustrative embodiment about 7460 µm, and/or a width or diameter of about 3000 µm to about 6000 µm, in the illustrative embodiment about 4000 µm, and/or optionally comprises an oval shape; a fluidic constriction channel 4 has a length of from about 200 µm to about 1,000 µm, in the illustrative embodiment about 500 µm, and/or a width or diameter of about 50 µm to about 500 µm, optionally about 50 µm to about 200 µm, or in the illustrative embodiment about 100 µm; a width or diameter of the overflow channel 3 and/or the second fluid transport channel 5A is about 10 to about 40 times greater than the diameter of the fluidic constriction channel 4; the width or diameter of the reaction well 2 is approximately 40 to approximately 120 to times the diameter of the fluidic constriction channel 4; the ratio of capillary pressures within the fluidic constriction channel 4 and the overflow channel 3 is at least 1.5:1 for example between 1.5:1 and 5:1 or between 2.0:1 and 4.0:1 (calculated using water in a plastic cartridge microfluidic device), between 10:1 and 1.5:1, or optionally about four to one; the fluidic constriction channel 4 and/or and the reaction well are completely filled with fluid; the fluidic constriction channel does not comprise air; a fluid air interface is present at an end of the fluidic constriction channel 4 distal to the reaction well 2; the fluidic constriction channel 4 is comprised of a hydrophobic material; and/or, a reaction well in fluid communication with an air control valve. In some embodiments, the fluidic device may comprise within at least the reaction well 2 a nanoparticle or a population of nanoparticles, optionally wherein said nanoparticle(s) is a lipid-based nanoparticle(s) or polymeric nanoparticle(s). Height and width dimensions provided herein are typically for rectangular channels and diameter dimensions are for circular channels. A skilled artisan will recognize that channels can take on different shapes, and that if other channel shapes are implemented dimensions provided herein for rectangular or circular channels can be adapted to provide similar results with other channel shapes. The different parts and sections of the microfluidic channel(s) are typically the same shape but can differ, and in one illustrative embodiment, have a rectangular shape. As used herein, "diameter" means "effective diameter", or "hydraulic diameter", for embodiments having channels or sections therein, that have a shape other than circular. The diameter of a circular channel typically does not exceed the height of a fluidic device comprising the channel.

Figure 13:
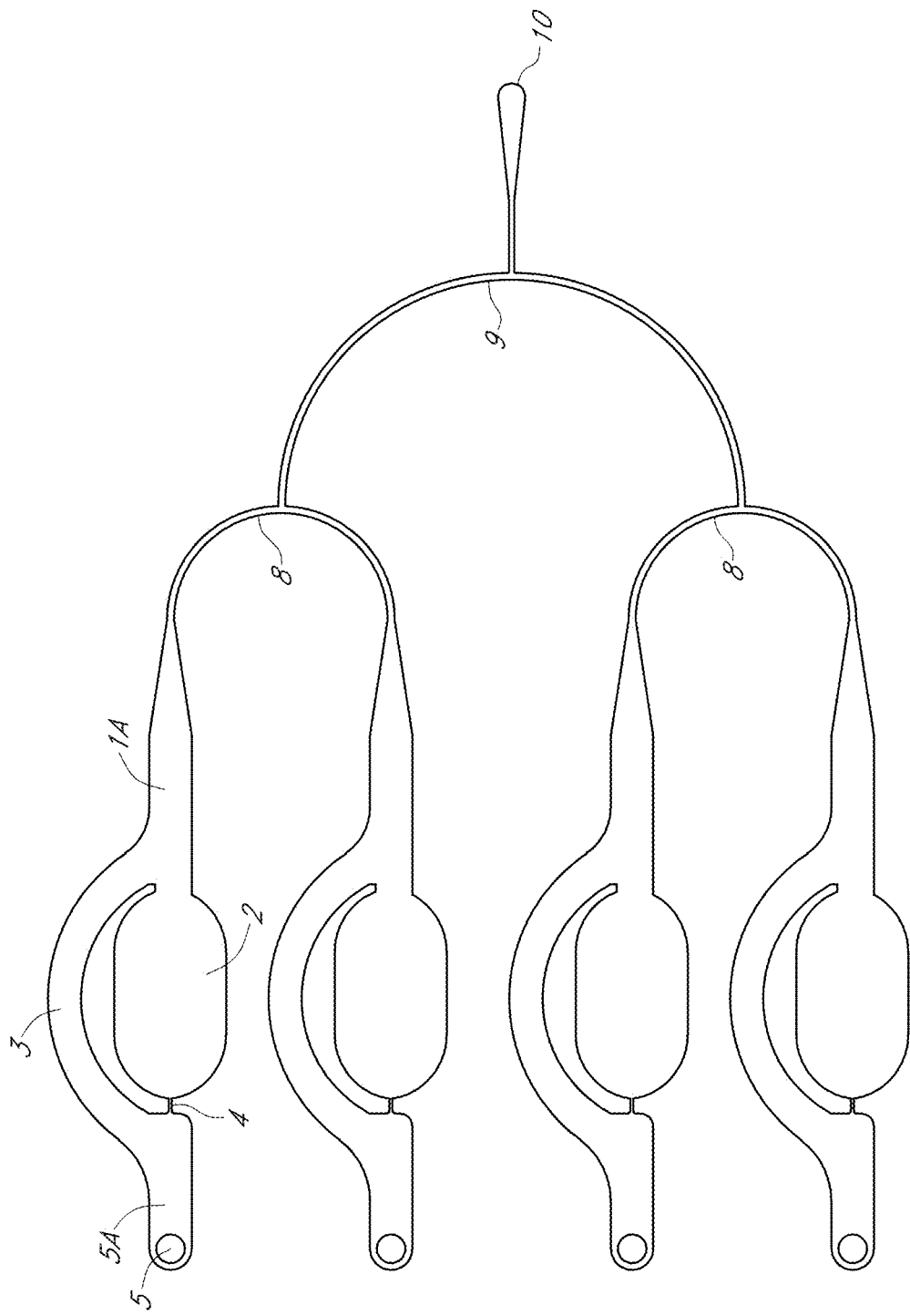
FIG. 13 illustrates an exemplary fluidic device comprising multiple fluidic device subunits connected to one another by a common fluid transport channel 9 which is connected to a common port 10.

In some embodiments, multiples of such fluidic devices (i.e., fluidic device subunits) can be connected in series and/or in parallel as shown in the illustrative embodiments of FIGS. 12A-12B, 13, 14A, 20, and 21A. For instance, as shown in FIG. 12A and FIG. 12B (and FIG. 14A with additional modifications), multiple fluidic devices connected in series, wherein the second fluid transport channel 5A of a device in the series is continuous with the first fluid transport channel 1A of the next device in the series. In some embodiments, the overflow channels 3 of each subunit are on the opposite side of at least two, but optionally each, successive fluidic device subunit (See e.g. FIG. 12B, FIG. 20, and FIG. 21A). Such configuration reduces the footprint of such device. In certain illustrative embodiments, such configuration is used in fluidic devices that are cassettes or cartridges, for example plastic disposable cassettes or cartridges. Furthermore, such configuration having overflow channels on opposite sides, provides better mixing of two fluids in the device, as the flow path is more disruptive because fluid cannot go only through the overflow channels. Rather, flow is altered between the well and the overflow channel for each subunit. In some embodiments (e.g., FIG. 13), each of said multiple device subunits are connected in parallel and can comprise a first fluid transport channel 1A but not a first port 1 (except for the first device in the series 10), wherein: at least two of said multiple devices are connected to one another by a first common fluid transport channel 8 connected to the first fluid transport channel 1A of each of said multiple devices to form a device subunit; and, where multiple device subunits are present in the device, at least two of said device subunits are connected to one another by a second common fluid transport channel 9 which is connected to a common port 10. While FIG. 13 shows four fluidic devices linked in series to one another, in some embodiments, additional fluidic devices (e.g., five or more, such as but not limited to eight, 12, 32 fluidic devices) may be linked to one another (e.g., as may be desired by the user), and can include a single common port between all of the devices, or subsets of such fluidic device subunits can be in fluid communication with a number of common ports. In addition, any number of common fluid transport channels could be included as may be required for distribution of fluid to the various subunits.

In some embodiments (e.g., as illustrated in FIG. 21B, as a singular device, and FIGS. 14A, 20, 21A, and 26 in devices with multiple fluidic device subunits in series), a fluidic device can include a first fluid transport channel 1A (part 201A in FIG. 20) in fluid communication with at least first and second port channels (12, 14) that terminate in a first and second port channel ports, respectively (11, 13). Such port channel ports (11, 13) are configured to, adapted to, and operable to, permit liquids to be introduced, inserted, flowed, injected, or pushed into, or pulled or withdrawn from the fluidic device, similar to port 1 in other configurations of fluidic devices herein. Thus, In some embodiments (e.g., as illustrated in FIGS. 14A, 20, 21A, and 26), a fluidic device can include multiple fluidic devices (i.e., fluidic device subunits) fluidly connected in series to one another, each of said multiple fluidic devices in the series comprises a first fluid transport channel 1A in fluid communication with at least first and second port channels (12, 14) that terminate in a first and second port channel ports, respectively (11, 13); the first fluidic device (first device subunit) in the series comprises a second fluid transport channel 5A in fluid communication with the first fluid transport channel 1A of a second fluidic device in the series; the second fluidic device in the series, and subsequent devices in the series if present (e.g. subunits 2, 3 and 4 in FIG. 14A), comprise a second fluid transport channel 5A in fluid communication with the first fluid transport channel 1A of the next fluidic device in the series; and, the second fluid transport channel 5A of the last fluidic device in the series (last subunit) terminates in an outlet port 5. It is contemplated that 2, 4, 6, 8, 10, 12, 20, 30, 40, 50, 75, 100, or more fluidic device subunits can be placed in series. The total fluid volume that is input into the devices when they are used in a method is determined by the desired volume of reaction product (e.g. nanoparticle formulation or protein precipitate) but can be, e.g., approximately one to 10,000 ml, one to 5,000 ml, one to 2,000 ml, one to 1,000 ml, one to 200 ml, such as one ml, 10 ml, 100 ml, 1,000 ml, 2,000 ml, 2,500 ml, 5,00 ml, 10,000 ml, or other amount up to but not limited to approximately 10,000 mL. Mixing of the first and second fluids (e.g., a lipid-based or polymer-based first fluid and a second fluid being an aqueous solution or buffer, or an aqueous solution and/or buffer and/or water-soluble polymer solution, respectively) will primarily take place within the reaction well 2 of each fluidic device subunit, but can also occur in the overflow channel 3. Tubing can be connected at the outlet port 5 that can lead into a collection container.

In some embodiments, fluidic devices herein that comprise fluidic device subunits can be referred to as fluidic device assemblies, some of which are coflowing fluidic device assemblies if they are also coflowing fluidic devices as discussed herein. In some embodiments of such fluidic device assemblies comprising multiple fluidic devices (i.e., fluidic device subunits), one or more passive air valves can be included in order to separately drive fluid into or out of a particular or a particular group of reaction wells or fluidic devices. The operation and configuration of passive air valves is disclosed in WO 2018/200896, incorporated herein by reference in its entirety. Fluidic devices herein can be formed in cassettes or cartridges, such as disposable cassettes of cartridges, for example disposable plastic cassettes or cartridges. Thus, in some embodiments, microfluidic device assemblies with microfluidic device subunits are formed in a disposable microfluidic cartridge. Such cassettes or cartridges can have different sizes and shapes, such as, but not limited to, rectangular, square, or circular, and in some illustrative embodiments are rectangular in shape with widths between 10 mm and 250 mm or between 20 mm and 150 mm, or 50 mm and 150 mm, length between 10 mm and 250 mm, 50 mm and 250 mm, 100 mm and 250 mm, or 50 mm and 150 mm, and a thickness/depth of between 1 mm and 10 mm, 2 mm and 5 mm, or 1 mm and 2 mm. As non-limiting examples, the cartridge or cassette can be 75.5 mm×50 mm×3 mm, 75.5×25×3 mm, or 90 mm×50 mm×7.5 mm. Some aspect provided herein are commercial products comprising two or more disposable cassettes or cartridges each comprising a fluidic device provided herein. Methods for making such cartridges and plastic components for such cartridges or cassettes are known in the art.

Figure 2A:
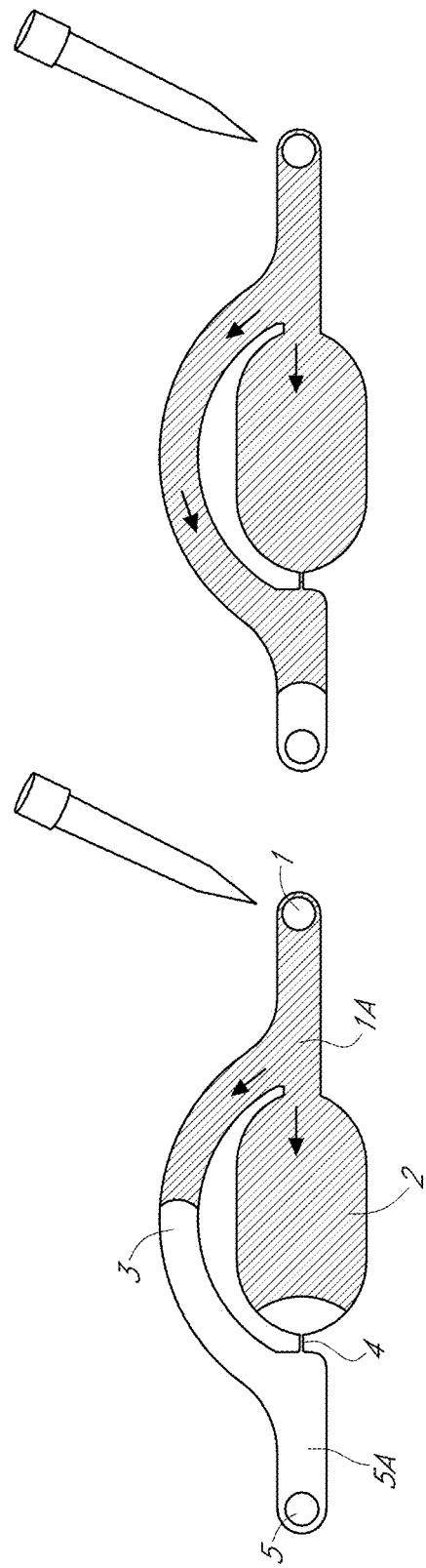
FIGS. 2A-2C illustrates the introduction and removal of fluids from an exemplary fluidic device that can be used to produce nanoparticles.
Figure 2B:
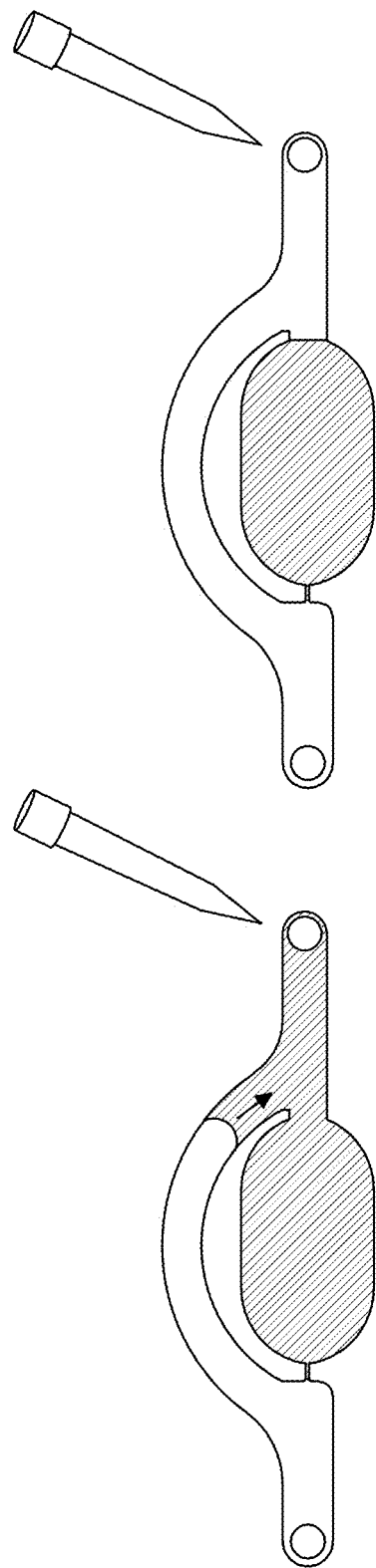
Figure 2C:
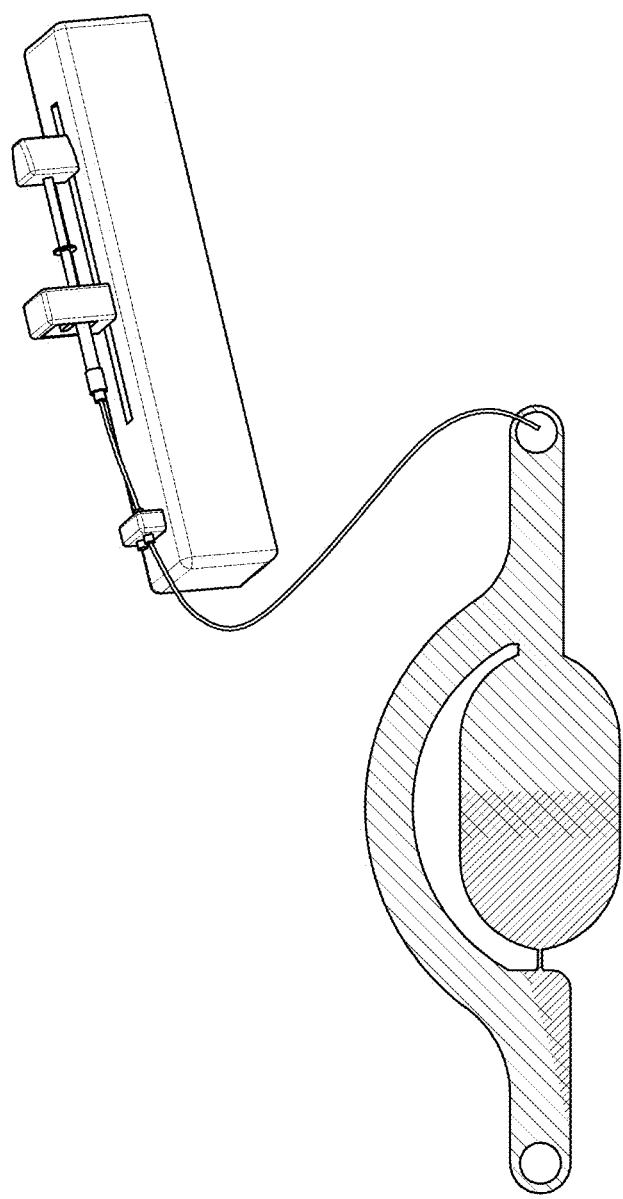

In one aspect, a fluidic device provided herein that includes a single first inlet port 1 or 10 (e.g., as illustrated in FIGS. 1, 2A-2C, and 10-13) can be used in methods to produce a reaction product, such as nanoparticles (e.g., liposomes, lipid micelles, or polymer-comprising nanoparticles wherein lipids or polymers are found in the envelope) or a protein precipitate by inputting a first fluid and a second fluid into the fluidic device. The fluidic device, as shown in FIGS. 1, 2A-2C, and 10-13, include a first port 1, first fluid transport channel 1A, reaction well 2, overflow channel (part 3), fluidic constriction channel 4, second fluid transport channel 5A and second port (part 5). To produce nanoparticles using such fluidic device, for example those shown in FIGS. 1, 2A-2C, and 10-13, a method that comprises three-steps can be used, as illustrated in FIGS. 2A-2C and further described herein. It will be understood for devices that include multiple fluid device subunits and a single input port, for example the devices of FIGS. 12 and 13, that description in the following paragraphs that refer to a single channel or reaction well, relate to each identical part of the subunits therein. In step one, the first fluid (e.g., an organic solvent solution for lipid-based nanoparticles or a polymer solution for polymer-based nanoparticles; indicated as a solid fill within the fluidic device) is introduced into the fluidic device to fill the device with the first fluid. In this step the first fluid is introduced into the fluidic device through the first port 1 or 10 (FIG. 13) where it enters a first fluid transport channel 1A, and then enters the reaction well 2 and the overflow channel 3 concurrently. Due to the difference in the resistance ratio associated with entering the reaction well 2 or the overflow channel 3, the reaction well 2 and fluidic constriction channel 4 will be filled completely with the first fluid as excess fluid continues to travel through the overflow channel 3. The fluid in the fluidic constriction channel 4 and the overflow channel 3 then meets at the junction between the overflow channel 3 and a second fluid transport channel 5A, and a combined stream flows through the second fluid transport channel 5A and exits the fluidic device through the second port 5. Upon completion of this first step, all parts of the fluidic device are filled with the first fluid.

In the second step of this exemplary method, the first fluid is trapped in the reaction well 2 and fluidic constriction channel 4. To accomplish this excess first fluid is removed from the other parts of the fluidic device (i.e., overflow channel 3, second fluid transport channel 5A), by applying negative pressure at a port (e.g., first port 1), so that the fluid retracts back through the second fluid transport channel 5A and continues retracting back through overflow channel 3 toward first port 1. When the first fluid reaches the junction between the fluidic constriction channel 4 and the overflow channel 3, the first fluid will travel through the overflow channel 3 only due to the stronger capillary effects in the fluidic constriction channel 4 compared to the overflow channel 3. After traveling through the overflow channel 3, the first fluid moves through the first fluid transport channel 1A, thereby creating a fluid-air interface at the opening of the reaction well 2, and is withdrawn from the device through the first port 1 (remaining in the reaction well 2 and fluidic constriction channel 4.

In the third step of this method, a second fluid, different than the first fluid, for example as discussed herein for the production of nanoparticles or a protein precipitate, is introduced into the fluidic device (e.g., at a flow rate of from 1 to 30 ml/minute, optionally from 5 to 20 ml/minute or 10 to 20 ml/minute) and mixed with the first fluid to produce nanoparticles. In some embodiments, for this third step about 100 to 1000 optionally 100 to 200 µl, second fluid is introduced through the first port in this step; or, wherein fluidic multiple devices are fluidly connected to one another in series or parallel, greater than 1000 µl aqueous buffer or water can be introduced through the first port 1 in this third step. It is noted that as more second fluid (e.g., aqueous buffer) is washed through the device, fewer nanoparticles will remain in the well, and eventually all the contents will be replaced with just the second fluid. In some embodiments in which a lower volume of the second fluid (e.g., 100 µl where 100 µl to 200 µl is typical) is introduced into the fluidic device, then the contents of the reaction well 2 will be replaced with the mixture of nanoparticles (e.g., in ethanol and aqueous buffer), but most of the mixture will exit through the second port(s) 5. This third step can employ a syringe pump prepared by connecting tubing from a syringe pump filled with the second fluid to a port (e.g., first port 1). Tubing can also be connected to the second port 5 that feeds into a collection container. The syringe pump can be set to a flow rate between 1 and 30 mL/min, as non-limiting examples, and the second fluid pumped into the fluidic device through first fluid transport channel 1A and into reaction well 2, replacing the first fluid that was trapped in the reaction well 2 and fluidic constriction channel 4. Thus, in some embodiments, the method for making nanoparticles can include: a) filling the fluidic device by introducing an organic solvent solution comprising dissolved lipids or a polymer solution thru the first port 1 into the fluidic device; b) trapping the organic solvent comprising dissolved lipids or the polymer solution in a reaction well 2 and a fluidic constriction channel 4 connected therewith by applying negative pressure at the first port 1 to remove some of the organic solvent solution or polymer solution from the fluidic device; and, c) introducing an aqueous buffer into the reaction well 2 through the first port 1 to mix with and replace the organic solvent comprising dissolved lipids or the polymer solution, wherein mixing of the organic solvent comprising dissolved lipids or the polymer solution and the aqueous buffer forms nanoparticles. Illustrative methods for producing nanoparticles using the illustrative device of FIG. 1 are disclosed for example in Example 1 and Example 2 herein.

Provided herein in another aspect, is a method for producing a reaction product using a fluidic device that includes a first fluid transport channel 1A in fluid communication with at least first and second port channels (12, 14) that terminate in first and second port channel ports, respectively (11, 13), wherein:
  a first fluid is introduced into a first fluid transport channel 1A of the fluidic device thru the first port channel port 11; and
  a second fluid that is different from the first fluid is introduced into the first fluid transport channel 1A thru the second port channel port 13, wherein a reaction well 2 of the device is in direct fluidic communication with the first fluid transport channel 1A, wherein a fluidic constriction channel 4 is in direct fluidic communication with the reaction well 2, and wherein some of the second fluid flows into the reaction well 2 and some (usually the remainder) of the second fluid flows around the reaction well 2 into an overflow channel 3 of the device, and wherein the first fluid mixes with some of the second fluid in the reaction well 2, thereby producing the reaction product.

Such devices used for this aspect are typically coflowing fluidic devices and such aspect can be referred to herein as a method for producing a reaction product using a coflowing fluidic device. Such coflowing fluidic devices typically have a Y junction that connects the first and second port channels (12, 14) at the first fluid transport channel of the fluidic device. In some embodiments of the method aspect provided immediately above, the method further includes collecting the reaction product through the second port 5. Such embodiments can be accomplished by inputting more total fluid (i.e. first fluid and second fluid) into the device than the total volumetric capacity of the device. In such a method it is believed that fluid moves through the device as shown in FIG. 21A. As fluid is input into the input ports, it moves in 2 paths, one flowing through the reaction well 2 and fluidic constriction channel 4 and the other path around the reaction well 2 through the overflow channel 3. The two fluid streams meet at the junction between the overflow channel 3 and a second fluid transport channel 5A, and a combined stream flows through the second fluid transport channel 5A and exits the fluidic device through the second port 5. Over time the combined stream includes reaction product that is formed in the reaction well 2 and the fluidic constriction channel 4. Such methods were used to prepare nanoparticles (Example 3) and protein precipitates (Example 4) as disclosed therein. Thus, typically the device that performs this method is configured to and operable to guide (and capable of and adapted for guiding) fluid entering the device through the first fluid transport channel 1A, into the reaction well 2 and the overflow channel 3. Without being limited by theory, such properties of the device are believed to be due to the difference in the resistance ratios of the reaction well 2, the overflow channel 3, the reaction well 2 and the fluidic constriction channel 4, which along with the reaction well 3, in illustrative embodiments is also filled with the first fluid and provides mixing with the second fluid as it is mixing within the reaction well 2. Exemplary devices for performing such a method are provided in FIGS. 14A, 20, 21A, 21B, and 26.

In certain embodiments, one fluid (e.g. first fluid) is an organic solvent solution comprising dissolved lipids, a polymer solution comprising at least one polymer dissolved in a solvent, or a protein solution. In certain embodiments, the other (or another) fluid (e.g. second fluid) input into the device is an aqueous buffer where the first fluid is an organic solvent solution comprising dissolved lipids and the method is a method for making particles, or a water-soluble synthetic polymer solution where the first fluid comprises at least one polymer dissolved in a solvent and the method is a method for making particles, or a protein precipitant where the first fluid comprises a protein and the method is a method for precipitating proteins. Such fluids are typically introduced into the device through first and second port channel ports (11 and 13) into first and second port channels (12, 14) where they then enter the first fluid transport channel 1A as shown for example in FIG. 21A.

In certain illustrative embodiments of this aspect provided immediately above, the fluidic device comprises a series of fluidic device subunits each having attributes provided hereinabove for the device in this method, and in illustrative embodiments substantially identical or identical, for example with respect to reaction well 2, overflow channel 3, and fluidic constriction channel 4, as disclosed hereinabove. In such embodiments, as fluid, which is typically a fluid stream created by input of the first fluid and the second fluid into the device, flows through an upstream fluidic device subunit into a second fluidic transport channel 5A of the upstream fluidic device subunit it enters a first fluidic transport channel 1A of a downstream fluidic device subunit as shown in FIG. 21A herein. Some fluid flows into the reaction well 2 of the downstream fluidic device subunit and some fluid flows around the reaction well 2 through the overflow channel 3. Such methods in illustrative embodiments, are continuous flow methods, and fluidic devices that include fluidic device subunits can be considered continuous flow systems. Such continuous flow methods and systems can include, for example fluid reservoirs for holding a first fluid and a second fluid respectively, as well as a pumping system that is adapted to and operable to input fluid into the fluidic device through the first port channel port 11 and the second channel port 13, such as through tubing that connects the fluid reservoirs to the port channel ports. Such continuous flow systems and methods providing the ability to scale up methods provided herein such that methods can be used to produce between 10 ul and 10 L, between 100 ul and 10 L, between 250 ul and 10 L, between 1 ml and 5 L, or between 1 ml and 2 L, or between 1 ml and 1 L, for example, of a reaction product solution or suspension. Example 3 herein demonstrates such a method that successfully produced 1 L of reaction product (nanoparticles).

Figure 27:
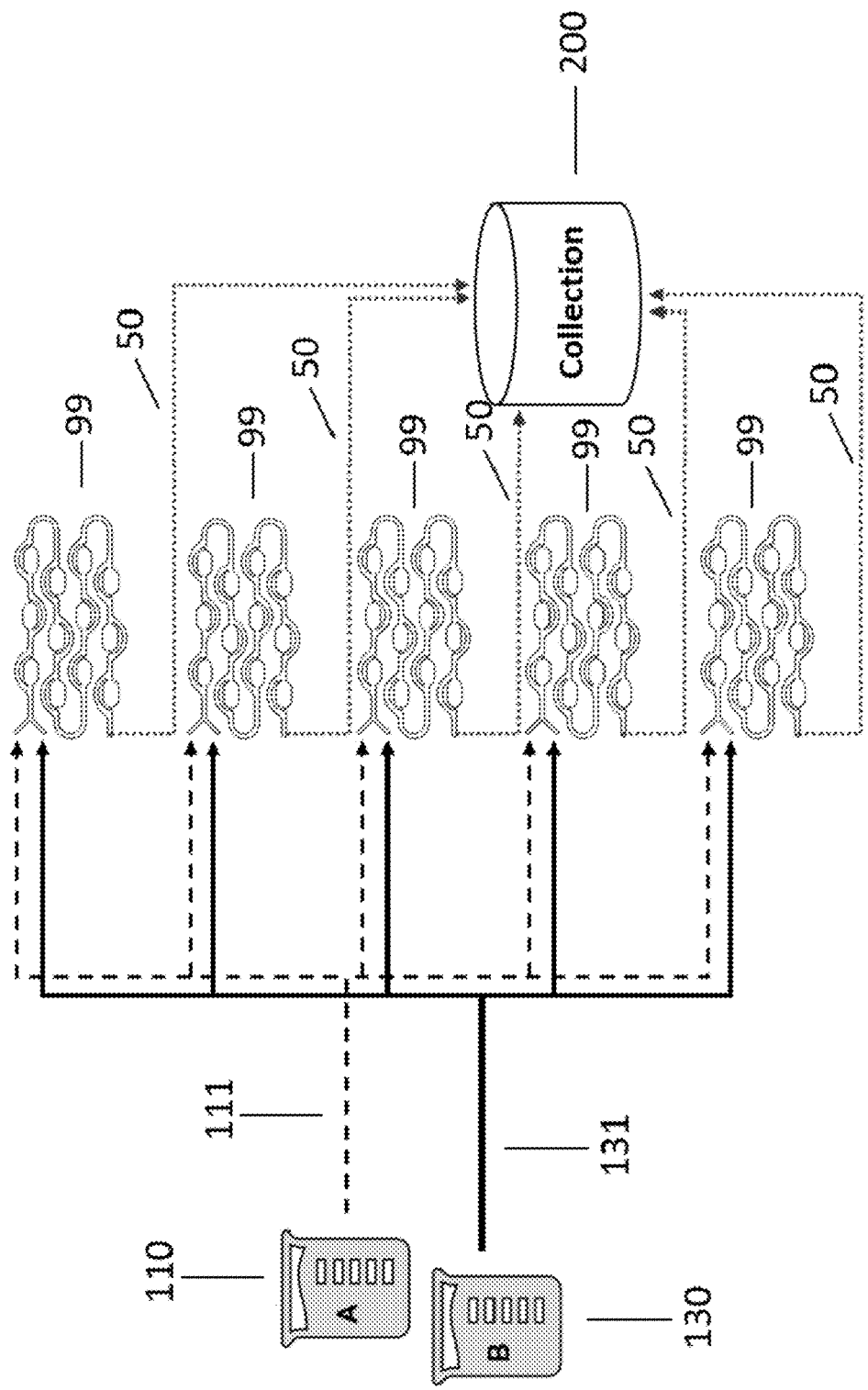
FIG. 27 illustrates a scale-up fluidic system that includes 5 fluidic device assemblies 99 in parallel.

Furthermore, by linking multiple fluidic devices, each comprising fluidic device subunits as described immediately above, the method and system can be used to scale up based on the number of linked fluidic devices to almost unlimited scale-up potential. For example, in some embodiments as shown in FIG. 27, two or more fluidic devices herein, which each can be referred to as a fluidic device assembly 99 as they each include more than 1 fluidic device subunit, in this case in series, can be connected in parallel. In this non-limiting embodiment, a vessel comprising a first fluid, for example a first fluid reservoir 110, and a vessel comprising a second fluid, for example a second fluid reservoir 130 are connected and in fluidic communication with fluidic device assemblies 99 of a fluidic system through a first port channel port and a second channel port of each fluidic device assembly, such as through tubing 111, 131 that connects the fluid reservoirs 110, 130 to the port channel ports. An outlet port of each assembly 99 can be connected and in fluid communication, for example with tubing 50, to a collection vessel 200. Such devices can permit scale-up from an individual microfluidic device assembly comprising microfluidic device subunits in series. Two, three, four, five, ten, twenty or more microfluidic device assemblies can be connected in parallel in such a configuration to form a large-scale fluidic system that produces reaction products with similar characteristics to those produced by each fluidic device assembly.

As illustrated in Example 3 herein, methods, coflowing fluidic devices (coflowing fluidic assemblies), and coflowing systems of this aspect are capable of producing particles, for example microparticles and nanoparticles, of different sizes in a controlled and repeatable manner. User-controllable parameters such as the relative flow rate of a first fluid stream comprising the first fluid and a second fluid stream comprising the second fluid, the total flow rate of the combined stream of the first fluid stream and the second fluid stream, the dimensions of the device and the subunits of the device, the relative dimensions of the parts in the device, for example the relative width of the fluidic constriction channel compared to the reaction well and the overflow channel, can be set or optimized for a given first fluid and second fluid to consistently produce particles of a similar desired size. In some embodiments, the desired size/diameter is of a range that is set by a desired size/diameter of less than about 1 um, 750 nm, 600 nm, 500 nm, or 200 nm, and greater than 50 nm, 75 nm, 100 nm, 150 nm, or 200 nm. Accordingly, in some embodiments the first fluid and the second fluid, or the combined first fluid and the second fluid can be input into the fluidic device at a flow rate between 0.1 ml/minute and 50 ml/minute, or between 0.5 ml/minute and 25 ml/minute, or between 0.5 ml/minute and 20 ml/minute, or between 1.0 ml/minute and 20 ml/minute, or between 0.5 ml/minute and 10 ml/minute, or between 0.5 ml/minute and 5 ml/minute, or between 0.5 ml/minute and 1.0 ml/minute, or exactly or about 0.5, 0.75, 0.8, 0.9, 1.0, 5, 10, 15, or 20 ml/minute. Furthermore, in some embodiments, a flow rate ratio can be used of between 1:20, 1:10, 1:5, 1:2, or 1:1 between the flow rates of the first fluid stream and the second fluid stream.

FIG. 20 provides an exemplary coflowing fluidic devices of small and relative large dimensions as provided in Table 1, that include fluidic device subunits in series that can be used to produce a reaction product (e.g. nanoparticles) according to the method aspect provided immediately above. In the large coflowing device of FIG. 20, the first well 202A in the series each has a connected fluidic constriction channel 204A with a length of 500 um and a width of 300 um. The second well 202B in the series has a fluidic constriction channel 204B with a length of 500 um and a width of 200 um. Every other well in the series has a fluidic constriction channel with a length of 500 um and a width of 100 um (as stated in Table 1). The wider fluidic constriction channel in the first two wells helps limit air-bubble formation when initially filling the device with fluid. In the small coflowing device (e.g. small dimension version of the device of FIG. 20) all fluidic constriction channels have a length of 200 um and a width of 80 um. It is noteworthy that such fluidic device was the fluidic device of large dimension used in Example 3. Accordingly, in certain embodiments of a microfluidic device that includes fluidic device subunits in series, a first fluidic constriction channel and a second constriction channel of a first subunit and second subunit respectively, are configured to, adapted to, or operable to, reduce air-bubble formation for example by having a larger width than other fluidic constriction channels in the fluidic device. For example, the first fluidic constriction channel can have a width that is 1.5 to 5 times, 2 to 4 times, and in illustrative embodiments, 3 times larger than the other fluidic constriction channels in the fluidic device, and the second fluidic constriction channel can have a width that is 25% to 50%, 30% to 40%, and in illustrative embodiments 33% smaller than the first fluidic constriction channel, and 1.25 to 3 times, 1.5 to 2.5 times, and in illustrative embodiments, 2 times larger than the other fluidic constriction channels in the fluidic device.

As disclosed herein, the mixing of a first fluid and a second fluid can result in the formation of nanoparticles, for example when the first fluid is an organic solvent comprising dissolved lipids and the second fluid is an aqueous buffer. In some embodiments, such as when using any of the fluidic devices and fluidic device assemblies disclosed herein that include a first fluid transport channel 1A in fluid communication with at least first and second port channels (12, 14) that terminate in a first and second port channel ports, respectively (11, 13) (coflowing fluidic devices), as illustrated for example in FIGS. 21A and 21B, mixing of the first and second fluids can occur in the reaction well 2 as well as the overflow channel 3 as illustrated in FIG. 21B with different line patterns representing the first fluid, the second fluid, and a mixture of the first fluid and second fluid, and mixing shown by line swirls in the reaction well 2. Such mixing typically occurs when the first fluid and the second fluid are introduced into the microfluidic device, each through a different port of the first and second port channel ports (11, 13). In fact, based on the teachings herein, such as the dimensions provided in Table 1, fluidic devices provided herein accomplish, are effective for providing, are capable of providing, are operable to provide, and/or are adapted to provide rapid mixing of a first fluid and a second fluid such as an organic fluid and an aqueous fluid, leading to the production of uniform reaction products (e.g. particles, such as nanoparticles or microparticles, or protein precipitates). Furthermore, in some embodiments of any of the fluidic device assemblies herein, especially device assemblies that include multiple fluidic devices in series, the device assembly can further comprise third, fourth, fifth, etc. fluid transport channels in fluid communication with corresponding third, fourth, fifth, etc. input ports, respectively, and in fluid communication typically through one or more additional channels to one or more reaction wells. Thus, additional input fluids (third, fourth, fifth, etc. fluids) can be input into devices herein to produce more complex mixtures and reaction products, such as more complex particles.

In embodiments of this aspect where a first fluid is a protein solution and a second fluid is a protein precipitant, efficient mixing as a result of the design of fluidic devices of this aspect, as described for example in FIG. 21B, allows in illustrative embodiments, for continuous precipitation of protein as some fluids from the input fluid stream create by the input of the first fluid and the second fluid flow through the device via the reaction well 2 as illustrated in FIG. 21A without the need for an incubation period. The applied flow rate ratios provided herein can result in precipitant concentrations of 2%, 1.33%, 0.67%, and 0.36%, which are lower than the typical range used in standard methods. This is beneficial, as precipitants can cause undesirable structural changes in the proteins of interest. Further, the device design described for this aspect could be incorporated into a continuous purification workflow, for example allowing for the extraction of a high yield expression product.

In methods provided herein for making particles, the type of particles formed, for example microparticles or nanoparticles, is dependent on the type of first and second fluids utilized. For instance, in some embodiments, the first fluid is an organic solvent solution comprising at least one organic solvent and at least one lipid and the second fluid is an aqueous buffer (optionally including additional components). In some embodiments, the first solution can comprise at least one lipid selected from the group consisting of dipalmitoylphosphatidylcholine (DPPC); cholesterol; 1,2-Dilauroyl-sn-glycero-3-phosphocholine (DLPC); 1,2-Dimyristoyl-sn-glycero-3-phosphocholine (DMPC); 1,2-Distearoyl-sn-glycero-3-phosphocholine (DSPC); 1,2-Dioleoyl-sn-glycero-3-phosphocholine (DOPC); 1,2-Dimyristoyl-sn-glycero-3-phosphoethanolamine (DMPE); 1,2-Dipalmitoyl-sn-glycero-3-phosphoethanolamine (DPPE); 1,2-Dioleoyl-sn-glycero-3-phosphoethanolamine (DOPE); 1,2-Dimyristoyl-sn-glycero-3-phosphate, sodium salt (DMPA); 1,2-Dipalmitoyl-sn-glycero-3-phosphate, sodium salt (DPPA); 1,2-dioleoyl-sn-glycero-3-phosphate, sodium salt (DOPA); 1,2-Dimyristoyl-sn-glycero-3-phosphoglycerol, sodium salt (DMPG); 1,2-Dipalmitoyl-sn-glycero-3-phosphoglycerol, sodium salt (DPPG); 1,2-dimyristoyl-sn-glycero-3-phospho-L-serine, sodium salt; 1,2-Dipalmitoyl-sn-glycero-3-phosphoserine, sodium salt (DPPS); 1,2-dioleoyl-sn-glycero-3-phospho-L-serine (DOPS), sodium salt; 1,2-Dioleoyl-sn-glycero-3-phosphoethanolamine (DOPE)-Glutaryl, sodium salt; tetramyristoyl cardiolipin sodium salt; 1,2-Distearoyl-sn-glycero-3-phosphoethanolamine (DSPE)-mPEG-2000, sodium salt; 1,2-Distearoyl-sn-glycero-3-phosphoethanolamine (DSPE)-mPEG-5000, sodium salt; and 1,2-Distearoyl-sn-glycero-3-phosphoethanolamine (DSPE)-Maleimide PEG-2000, sodium salt; a mixture thereof; and other suitable lipids and/or mixtures (a preferable mixture being DPPC, cholesterol and DOTAP). In some embodiments of producing lipid-based nanoparticles, the organic solvent can be selected from the group consisting of ethanol, methanol and chloroform, ethyl acetate, isopropanol, and hexane (preferably ethanol). In some embodiments, the dissolved lipids can comprise DPPC, cholesterol and DOTAP, and the organic solvent solution can comprise ethanol. In such embodiments, the second fluid is typically an aqueous buffer (e.g., any buffer having an effective buffering capacity at the pH range needed for nanoparticle synthesis (e.g., physiological buffer) with or without a salt), and/or can be selected from the group consisting of or based upon bicine (2-(Bis(2-hydroxyethyl)amino)acetic acid), carbonate, cacodylate (Dimethylarsenic acid), Hepes (4-(2-hydroxyethyl)-1-piperazineethanesulfonic acid), isotonic sucrose, MES (2-(N-morpholino)ethanesulfonic acid), MOPS (3-(N-morpholino)propanesulfonic acid), phosphate-buffered saline (PBS), PIPES (Piperazine-N,N'-bis(2-ethanesulfonic acid), potassium phosphate, saline solution, TAPS ([Tris(hydroxymethyl)methylamino]propanesulfonic acid), TES (2-[[1,3-dihydroxy-2-(hydroxymethyl)propan-2-yl]amino] ethanesulfonic acid), Tricine (3-[N-Tris(hydroxymethyl) methylamino]-2-hydroxypropanesulfonic acid), and/or Tris (e.g., Tris(hydroxymethyl)aminomethane or, 2-Amino-2-(hydroxymethyl)propane-1,3-diol; e.g., TAE (Tris-acetate EDTA), TBE (Tris-borate-EDTA); TAPSO (3-[N-Tris(hydroxymethyl)methylamino]-2-hydroxypropanesulfonic acid); and in some embodiments is preferably PBS. The mixture of these first and second fluids as described herein produces nanoparticles comprising a lipid membrane surrounding the aqueous buffer (and any additional components).

In some embodiments, polymer-based nanoparticles can be produced using these methods wherein the first fluid can be a polymer solution comprising at least one polymer and at least one solvent (e.g., acetonitrile) and the second fluid is a water-soluble polymer solution comprising at least one water-soluble polymer and any additional components). In some embodiments, the polymer can be selected from the group consisting of polylactic acid (PLA), poly-1-lysine (PLL), polyglutamic acid (PGluA), polyglycolic acid (PGA), polyethylene glycol (PEG), polycaprolactone (PCL), polyaspartate (PAA), poly(d,l-lactide-co-glycolic) acid (PLGA), cyclodextrins (CD), and N-(2-hydroxypropyl)-methacrylamide copolymer (HPMA), a natural polymer, chitosan, heparin, albumin, dextran, gelatin, alginate, collagen, a mixture thereof, and/or other suitable polymers, and/or mixtures thereof. The solvent can be selected from the group consisting of dichloromethane and ethyl acetate, benzyl alcohol, cyclohexane, acetonitrile, and acetone, or other suitable solvent. In some such embodiments where the first fluid is a polymer solution, the second fluid may be an aqeuous solution (e.g., water or an aqueous buffer such as PBS) or water-soluble synthetic polymer solution comprising, for instance, poly(vinyl alcohol) or didecyldimethylammonium bromide. The mixture of these first and second fluids produces nanoparticles comprising a polymer-based membrane surrounding the water-soluble polymer solution (and any additional components).

The nanoparticles produced by these methods can also be characterized by any suitable technique to determine, for instance, size, polydispersity index (PDI), or zeta potential, optionally as measured using a technique such as dynamic light scattering (DLS) or transmission electron microscopy (TEM). In preferred embodiments, the nanoparticles have a diameter of between 5 nm and 500 nm, or less than 600 nm. As explained in Example 1, in some embodiments such as where a nanoparticle having a diameter of less than about 600 nm are desired, a microfluidic device having a single inlet port 1 can be used in a method for producing particles where a second fluid is input into the fluidic device after a reaction well 2 of the device is filled with a first fluid, and the fluidic constriction channel of the fluidic device has a width or diameter of less than 400 µm and the flow rate used to input the second fluid into the device is greater than 5 ml/minute, for example between 5 ml/minute and 20 ml/minute or between 10 ml/minute and 20 ml/minute or between 5 ml/minute and 10 ml/minute. In some embodiments, the nanoparticle is lipid-based and in some embodiments the nanoparticles are polymer-based. In some embodiments, the particles are comprised of a metal. Such metal can include, but is not limited to, silver, gold and copper. In illustrative embodiments the particles are metallic nanoparticles. However, other types of nanoparticles may also be produced using these fluidic devices and methods.

The second fluid in such embodiments may comprise additional components such as, but not limited to, one or more detectable agents, therapeutic agents, nucleic acid-base compounds (e.g., DNA, RNA, and derivatives thereof), proteins (including but not limited to therapeutic proteins), immunomodulatory nucleic acids, proteins, and/or other compounds (e.g., vaccines), and/or other suitable additional components as may be understood by those of ordinary skill in the art. Nanoparticles, especially liposomes, may also be further processed by, for instance, treating the same with polyethylene glycol (e.g., PEGylation) and/or mannosylating the same. Liposomes may also be anionic, neutral, or cationic depending at least in part on the type of lipid utilized. Those of ordinary skill in the art would understand that these and other additional components and/or post-production modifications may be made using standard reagents and techniques.

In some embodiments, one of the fluids input into the device is a protein solution. It is contemplated that any protein can be included in such protein solution. In some embodiments, such protein is an industrial protein, a control protein for a diagnostic assay or a therapeutic protein. Concentrations of proteins in a fluid input into the device can be any concertation used for such protein for protein precipitation using conventional batch stir/incubate methods. For example, the concentration can be between 0.1 and 100 mg/ml, for example between 1 and 50 mg/ml, for example between 1 and 25 mg/ml, for example between 1 and 10 mg/ml. In such embodiments, the other fluid in illustrative embodiments is a protein precipitant. Any known protein precipitant can be used in methods using the fluidic devices herein for protein precipitation. For example, the protein precipitant can be a neutral salt such as ammonium sulfate, a mineral acid, such as hydrochloric acid or sulfuric acid, a miscible solvent such as ethanol or methanol, a non-ionic hydrophilic polymer, such as a dextran or a polyethylene glycol, a polyelectrolyte such as Alginate, carboxymethylcellulose, polyacrylic acid, tannic acid or polyphosphates, trichloroacetic acid, phenol, ammonium acetate/methanol, methanol chloroform. Concentrations of protein precipitants used can be the same as those used for traditional mix/incubate reactions. For example, TCA can be used at a concentration range of 4-20%. In illustrative embodiments the protein precipitant does not alter protein structure. For example, the protein precipitant can be a polyethylene glycol, such as PEG 6000.

Other embodiments of such methods are also contemplated as being suitable for use with the fluidic devices provided herein, as will be understood by those of ordinary skill in the art.

The fluidic devices provided herein, including fluidic device(s) within a cartridge, and fluidic circuits therein, can be fabricated using, for example, but not limited by, various soft lithographic micro-embossing techniques. A variety of fabrication micro-forming methods that utilize, for example, but are not limited to, micro-milling, micro-stamping, and micro-molding, can be matched to substrate material properties. In some embodiments, the fluidic devices and cartridges can be injection molded using a suitable plastic. In various embodiments of a device according to the present teachings, a substrate can be an optically transmissive polymer, providing good optical transmission from, for example at least about 85% to 90% optical transmission over a wavelength range of about 400 nm to about 800 nm. Examples of polymeric materials having good optical transmission properties for the fabrication of various embodiments of a fluidic device or circuit include organosilicon polymers. In some embodiments, a fluidic device presented herein is composed of hydrophobic materials. In some embodiments, the fluidic device is composed of hydrophobic materials such as polystyrene, polycarbonate, poly(methyl methacrylate) (PMMA), and/or polydimethylsiloxane (PDMS), polypropylene, cyclic-olefin polymers (COP), cyclic-olefin copolymers (COC), polystyrene polymers, polycarbonate polymers, acrylate polymers, and the like. Other hydrophobic materials may also be used as would be understood by those of ordinary skill in the art.

Further dimensions are provided herein, for exemplary fluidic devices. Dimensions of non-limiting exemplary fluidic devices are found in Table 1. In some further embodiments, the fluidic device has a height of between about any of 100, 125, 150, 175, 200, 225, or 300 pm on the low end of the range and about any of 200, 225, 250, 275, 300, 400 and 500 µm on the high end of the range. In illustrative embodiments, the fluidic device has a height of about any of 100-500 µm (e.g., about any of 100, 150, 200, 250 300, 350, 400 450, 500, or 300-500 µm). In some embodiments, for example those related to nanoparticle manufacturing, the fluidic device can have a height of between about any of 100, 200, 300, 325, 350, 375, 400, and 425 µm on the low end of the range and about any of 400, 425, 450, 475, and 500 µm on the high end of the range. In some embodiments, the first fluid transport channel and the second fluid transport channel are each about 400 microns in length, or about 2,000 to 10,000 pm, or about 5,900 µm (as in the fluidic devices of FIGS. 1 and 10-14A). In other embodiments, the overflow channel has a length between about any of 400, 425, 450, 475, 500, and 525 µm on the low end of the range and about any of 500, 525, 550, 575, 600, and 625 µm on the high end of the range, or about 8,000 to 15,000 µm, or about 10,900 µm (as in the fluidic devices of FIGS. 1 and 10-14A). In illustrative embodiments, the overflow channel has a length between about any of 400 and 625 µm. Other sizes may also be suitable as may be derived from this specification or the examples, and/or otherwise determined by those of ordinary skill in the art.

In some embodiments, on-device liquid handling for performing methods using fluidic devices herein, can be externally actuated in manual or automated mode using standard laboratory liquid handling equipment. According to various embodiments of components, devices and methods of this disclosure, a pressure applied at or between ports can be used as a motive force for moving liquids, for example, from part of a fluidic device to another part of that or another fluidic device. For example, a motive force for on-device liquid handling can be externally actuated by applying a decreased or negative pressure at a port or between ports or by applying an increased or a positive pressure at a port or between ports. Given that a full vacuum by definition is the absence of pressure, for example, 0 torr, and given that 1 standard atmosphere of pressure is, for example 760 torr, then a negative pressure is a decreased pressure less than 760 torr, for example, and a positive pressure is an increased pressure greater than 760 torr, for example. In that regard, on-device liquid handling for various embodiments of components, devices and methods of this disclosure can be externally actuated using any manual or automated standard laboratory liquid handling equipment, such as by manual or automated pipetting systems utilizing solid or liquid displacement, that can provide a pressure from between about 720 torr to about 800 torr, which is about +/−40 torr from 1 standard atmosphere of pressure.

Figure 26:
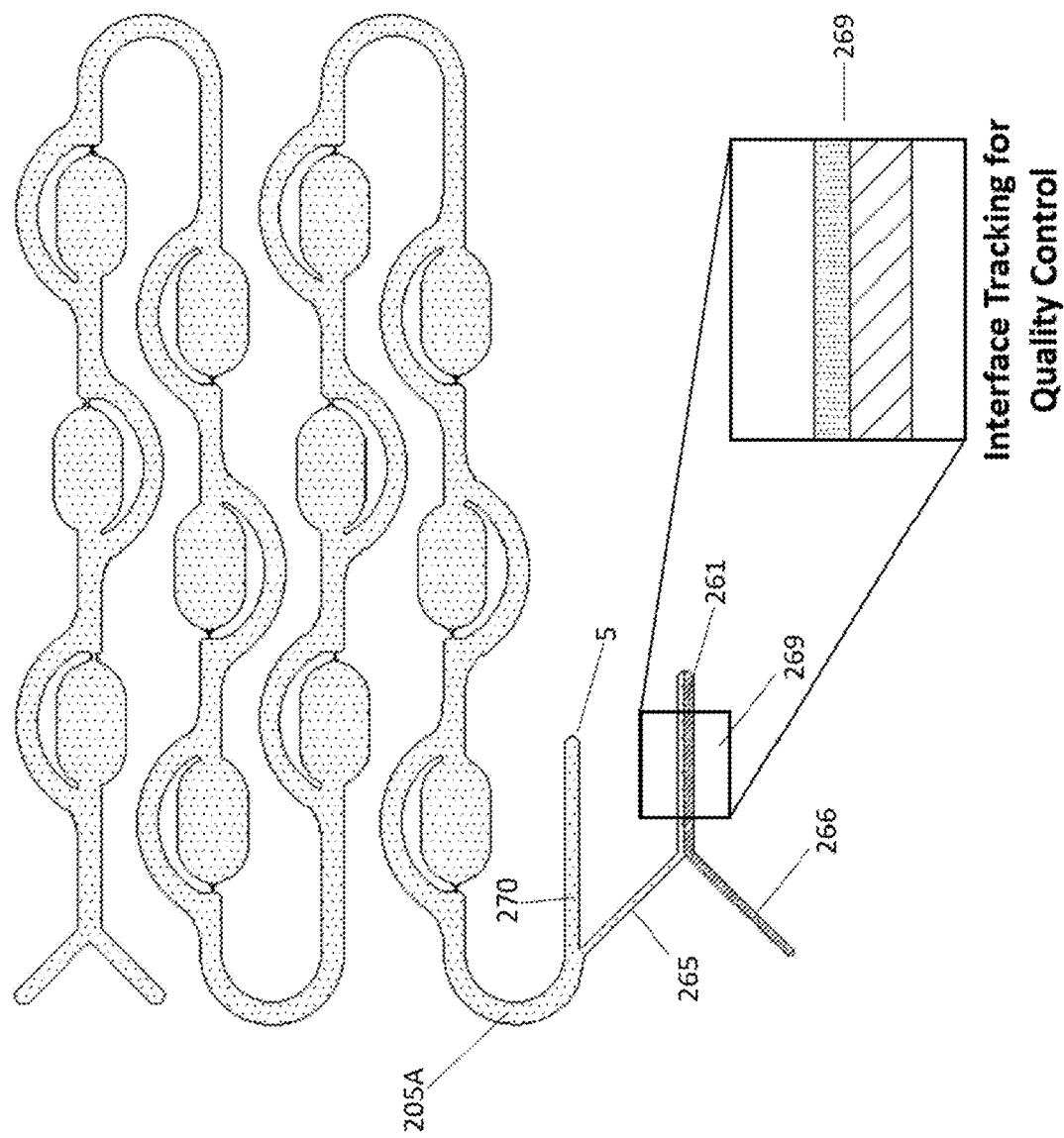
FIG. 26 illustrates a further exemplary embodiment of a fluidic device similar in design to the device shown in FIG. 20 and FIG. 21A that further includes an interface tracking channel for quality control.

In some embodiments, coflowing devices provided herein, include a QC subassembly as illustrated in FIG. 26. Such subassembly typically includes a quality control channel 261. Such quality control channel 261 is typically in indirect fluidic connection with a second fluid transport channel 205A of the final microfluidic device subunit in the series. In some embodiments of methods provided herein for producing a reaction product, especially a particle such as a microparticle or nanoparticle, using a coflowing fluidic device for example with an input aqueous phase first fluid and an input organic phase second fluid, the method further comprises analyzing the reaction product using a QC subassembly. In such embodiments, while most of the reaction product formulation is output for collection through a final transport channel 270 in direct fluidic communication with the second fluid transport channel 205A of the final microfluidic device subunit in the series, a fraction of the reaction product formulation is guided into the quality control channel 261 through a reaction product QC channel 265 also in direct fluidic communication with the second transport channel 205A of the final microfluidic device subunit in the series. In the QC subassembly, the reaction product formulation output from the fluidic device and a reference fluid with known rheological properties are added as inputs into a Y-junction formed by the reaction product QC channel 265 and a reference QC fluid channel 266. Typically, the width/diameter of the reaction product QC channel 265 is less than ½, ⅓, or ¼ the width/diameter of a the final transport channel 270.

As shown in the Inset of FIG. 26, which focuses on an observation channel section 269 formed in a portion of the quality control channel 261, an interface between a fluid stream from the fraction of the reaction product guided to the quality control channel and a fluid stream from a reference fluid are observed, monitored, and/or tracked for quality control of the reaction product. The observation channel section 269 is typically as an at least partially transparent section, and observation is performed using, for example a microscope or other imaging system. The widths of each fluid stream provided by the reaction product passing through the quality control channel 261 can be observed, measured, and tracked, in illustrative embodiments over time, to observe the quality of the reaction product, for example by quantifying formulation consistency over time. If the size or volume fraction of the reaction product (e.g. nanoparticles) changes throughout formulation, the pressure drop across the channel will change, and the widths of each fluid stream will change. This QC application can be utilized in as in-line quality control, for example in large-volume production (e.g. production of volumes greater than 100 ml, 250 ml, 500 ml, or 1 L, for example 1 L to 10 L), to ensure that particle size is staying relatively constant over time. For example, in some embodiments, a 5% or greater change in width of a fluid stream is indicative of particle inconsistency and can be used as a an acceptance cutoff for example. It is noteworthy that the QC subassembly of FIG. 26 is itself a separate aspect of the invention that can be in direct fluidic communication with virtually any fluidic device, especially microfluidic device, and can be used to monitor intra-lot quality control of a reaction product made using the fluidic device, such as a particle (e.g. microparticle or nanoparticle) reaction product. Such a QC subassembly provided herein is operable for, effective for and/or adapted for determining the quality and consistency of a reaction product over time.

In certain embodiments, for performing in-line quality control when using fluidic devices herein to produce reaction products, or for detecting the formation of a precipitate, a detection system, such as an optical detection system, for example a microscope or other imaging system, can be in optical communication with the fluidic device for example at the observation channel section 269. For such embodiments, the observation channel section 269 is ideally transparent, for example transparent glass or transparent plastic. A detection system can include an image recording and processing system. The image recording and processing system can comprise at least a light source, a recording device (e.g., a camera), and an image processor communicably coupled to the imaging device that determines a width of the fluid stream and/or other properties of the fluid based on for example two or more images using one or more algorithms. The light source and recording device (e.g., camera) are typically positioned to capture two or more images of the fluid stream through the observation channel section 269. Suitable, exemplary image processors (e.g., imaging processing systems) can include, for instance, a general purpose computer comprising Matlab (Mathworks, Boston, MA), Image J (an open source image analysis system), or other system as may be available to those of ordinary skill in the art. In some embodiments, the image processor is integrated into or wirelessly connected to the recording device (e.g., digital camera). Thus, in some embodiments, a fluidic system herein can include a smartphone, a tablet, a personal digital device, a computer pad, a netbook, and/or a computer having imaging processor and/or digital camera integrated therein, or a camera per se. In some embodiments, the camera may be one of a Charge-Coupled Device (CCD) or Complimentary Metal-oxide Semiconductor (CMOS) camera. Suitable light sources can include, in some embodiments, at least one Light Emitting Diode (LED) or LED panel. The at least one LED may be a colored LED. An excitation filter may filter the at least one LED. At least one such light source (e.g., LED or LED panel) may be symmetrically positioned off-axis from the camera with reference to the array. The system can also include an emission filter for filtering light entering the camera.

Figure 15:
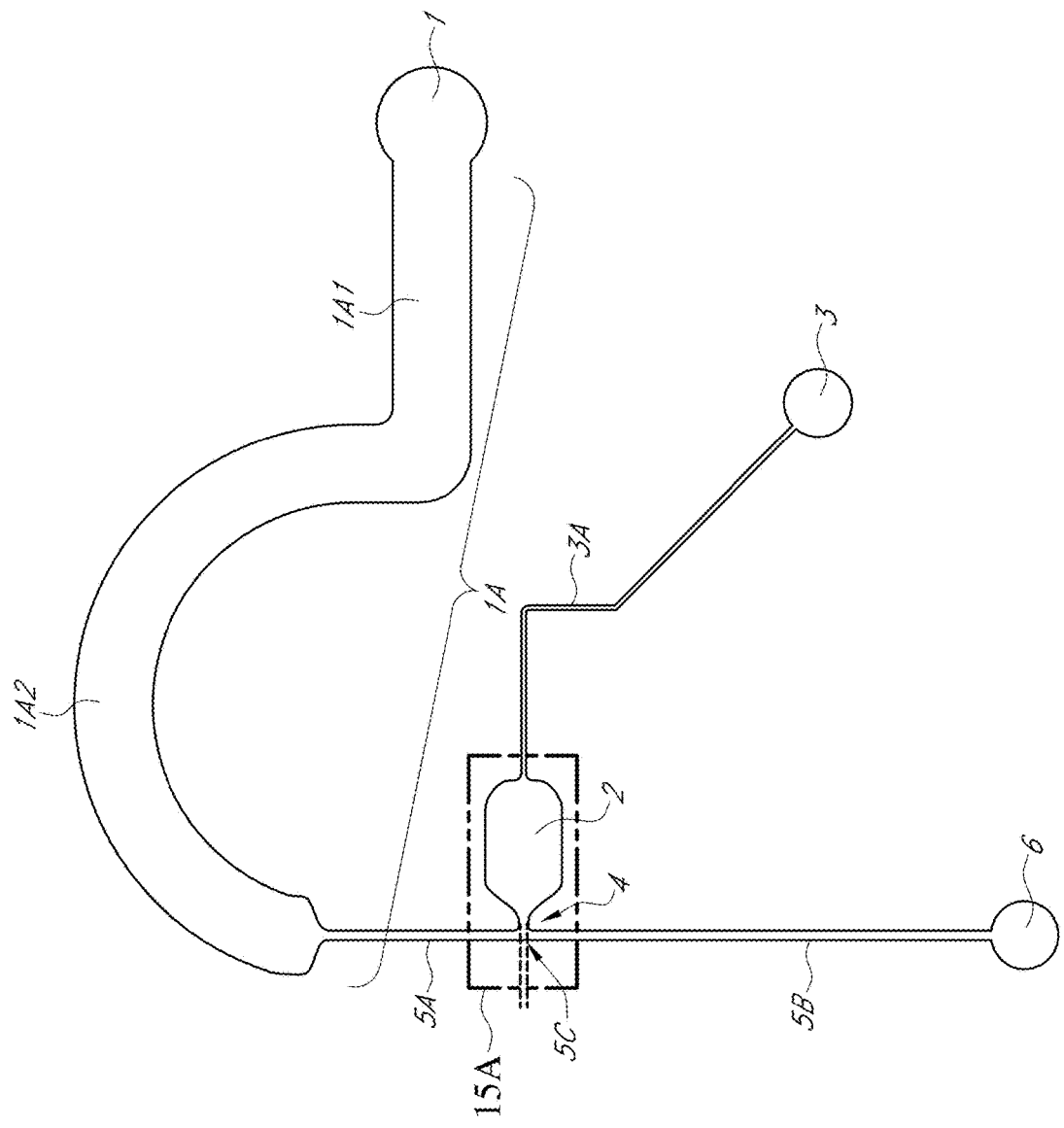
FIGS. 15 and 15A illustrate an exemplary fluidic device in which 1 is a first port; 1A is a first fluid transport channel; 1A1 is a straight section of the first fluid transport channel 1A; 1A2 is a rounded section of the first fluid transport channel 1A; 2 is a reaction well; 4 is a fluidic constriction channel; 3A is passive pressure sensing channel; 3 is a second port; 5A is a second fluid transport channel; 5B is a third fluid transport channel; 5C is an interface channel segment; and 6 is a third port.

Provided herein in one aspect, is a device, in illustrative embodiments a microfluidic device for detecting a reaction product. Such a device is effective for determining and/or detecting and operable to determine and/or detect a reaction product or whether a first fluid and a second fluid react by forming a reaction product. A related aspect provided herein is a method for using such a device to form, detect, measure, and/or analyze a reaction product (e.g. a precipitate) of one or more components of a first solution and one or more components of a second solution (and possibly additional components of additional solutions). Such a device for detecting a reaction product, is illustrated in FIG. 15 herein. A device for detecting a reaction product can be intended for use, for example, in chemical formulation and/or precipitation studies, with specific focus on the detection and study of fluidic compound interactions that may involve, for non-limiting example, precipitation development.

A device for detecting a reaction product provided herein in illustrative embodiments, includes three fluidic transport channels and an interface channel segment in fluidic communication with each other (i.e., first, second, and third fluid transport channels and interface channel segment), a reaction well, a fluidic constriction channel, and a passive pressure sensing channel. The reaction well is in fluidic communication with the second and third transport channels at the interface channel segment via the fluidic constriction channel.

The exemplary device also contains three input/output ports for entry and exit of fluid. The device is designed to provide passive, on-chip capture of a specific volume of a first fluid (i.e., first fluid droplet) and to allow input of a second fluid into the system following capture, typically passive capture, of the first fluid droplet. Interaction and reaction between first and second fluids occur within the device and can be monitored for a range of time periods.

A device for detecting a reaction product provided herein, can be useful, for example, in the field of chemical formulation development. The device allows detailed analysis and measurements that provide more accurate, repeatable, and high throughput studies of the interaction of components of two or more fluids, which can be members of a library of compounds. A particular embodiment of this aspect of a device for analyzing a reaction product finds use in the development and study of anti-perspirant compounds by testing the interaction of potential anti-perspirant compounds or formulations with compositions representing sweat compounds under physiologically-relevant conditions. This exemplary device is optimized to closely match the dimensions of an eccrine sweat pore, allowing for close mimicking of in vivo sweat conditions. As described herein and as may be understood by those of ordinary skill in the art, dimensions of various parts of the device can also be altered within the specified ranges to meet alternative application needs. These other applications in some embodiments, are within the general field of chemical formulation development and the potential interaction of two or more compounds is of interest.

The various structures/components of a fluidic device for detecting a reaction product are illustrated with respect to FIG. 15. A skilled artisan will recognize that variations of the geometries and sizes of structures/components can be made while retaining the effectiveness of such a device for detecting, measuring, and/or analyzing a reaction product. Such a device in illustrative embodiments includes a first port 1; a first fluid transport channel 1A, optionally having a relatively straight or straight section 1A1 and an optionally rounded section 1A2; a reaction well 2; a fluidic constriction channel 4; a passive pressure sensing channel 3A; a second port 3; a second fluid transport channel 5A; a third fluid transport channel 5B, an interface channel segment 5C and, a third port 6. In this illustrative embodiment, the second fluid transport channel 5A is in direct fluidic communication with the first fluid transport channel 1A at an end of the first fluid transport channel opposite the first port; the fluidic constriction channel 4 is in direct fluidic communication with the reaction well 2 and an interface channel segment 5C directly connecting the second fluid transport channel 5A and the third fluid transport channel 5B, wherein the width of the interface channel segment is identical to the width of the fluid transport channel to which it is directly connected; the reaction well 2 is in direct fluidic connection with the passive pressure sensing channel 3A at an end of the passive pressure sensing channel opposite the second port 3; the passive pressure sensing channel 3A extends from the reaction well 2 opposite the fluidic constriction channel 4 and terminates at the passive pressure sensing channel port 3; and the first fluid transport channel 1A is not in direct fluidic communication with the reaction well 2.

The width, length, and depth ranges of each part of the illustrative device according to FIG. 15 are provided in Table 2 below. These dimensions have the potential to be modified within the non-limiting exemplary indicated ranges to fit additional uses in additional fields of study, given the potential for various uses in that field. A variety of combinations of depths, widths, and lengths may be used for each part in the device to achieve desired functionality.

Table 2 provides the ranges of the various dimensions of parts in a device such as that illustrated in FIG. 15.

TABLE 2

| Device Parts | Dimension | Range |
| --- | --- | --- |
| First fluid transport channel 1A | Length | 3000-10,000 μm |
| | Width | 15-1000 μm |
| | Depth | 15-350 μm |
| Reaction well 2 | Length | 400-1500 μm |
| | Width (at widest point of well) | 200-1000 μm |
| | Depth | 15-300 μm |
| Fluidic constriction channel 4 | Length | 10-500 μm |
| | Width | 15-500 μm |
| | Depth | 15-300 μm |
| Passive pressure sensing channel 3A | Length | 1500-4500 μm |
| | Width | 5-100 μm |
| | Depth | 5-100 μm |
| Second fluid transport channel 5A | Length | 400-2000 μm |
| | Width | 15-100 μm |
| | Depth | 15-100 μm |
| Interface channel segment 5C | Length | 15-500 μm |
| | Width | 15-100 μm |
| | Depth | 15-100 μm |
| Third fluid transport channel 5B | Length | 1500-4000 μm |
| | Width | 15-100 μm |
| | Depth | 15-100 μm |

Various dimensions of parts of a fluidic device for detecting a reaction product, such as that illustrated in FIG. 15, can have relative tolerances, as disclosed in the following paragraphs. In some embodiments, the width of the second and third fluid transport channels (5A and 5B) are different or in illustrative embodiments the same. The width of the second and third fluid transport channels (5A and 5B) can be between 3/200 and the same width of the first fluid transport channel 1A, for example at a section in direct fluidic communication with (directly connected to) the second fluid transport channel. In illustrative embodiments, the width of the second fluid transport channel 5A is between 3/200 and 1/1.5, or between 1/100 and 1/2, or between 1/10 and 1/2, or between 1/10 and 1, or between 1/8 and 1/2, or between 1/5 and 1/2, or between 1/4 and 1/2 the width of the first fluid transport channel 1A, for example at a segment thereof in direct fluidic communication with (directly connect to) the second fluid transport channel. Such a segment for example, can be the first fluid transport channel.

In some embodiments, the depth of the second and third fluid transport channels (5A and 5B) are different or in illustrative embodiments the same. The depth of the second and third fluid transport channels (5A and 5B) can be between 3/70 and the same depth of the first fluid transport channel 1A, for example at a section in direct fluidic communication with (directly connected to) the second fluid transport channel. In illustrative embodiments, the width of the second fluid transport channel 5A is between 3/70 and ½ or between ⅛ and ½ the width of the first fluid transport channel 1A, for example at a segment thereof in direct fluidic communication with (directly connect to) the second fluid transport channel.

In some embodiments, the width and depth of an end of the interface channel segment 5C directly connected to the second fluid transport channel 5A is the same as the width and depth of the second fluid transport channel 5A and the width and depth of an opposite end of the interface channel segment 5C directly connected to the third fluid transport channel 5B is identical to the width and depth of the third fluid transport channel 5B. As such, the interface channel segment 5C can have a narrowing or widening width and/or depth. In illustrative embodiments, the width and depth of the interface channel segment, the second fluid transport channel, and the third fluid transport channel are the same.

The length of the interface channel segment 5C is typically equal to the width of the fluidic constriction channel 4. In some embodiments, the length of the fluidic constriction channel 4 is between 0.0025 to 1.25, and in illustrative embodiments between 0.0025 and 0.025 the length of the second and/or third fluid transport channels 5A and 5B. In some embodiments, the width of the fluidic constriction channel 4 is between 0.1 to 33 times, and in illustrative embodiments 0.25 to 4 times the width of the second and/or third fluid transport channels 5A and 5B. In some illustrative embodiments, the width and/or depth of the fluidic constriction channel 4 are the same as those of the second and/or third fluid transport channels 5A and 5B.

Tolerances can also be considered in view of hydraulic diameter, especially for illustrative embodiments of devices herein where channels are rectangular or hexagonal in shape. It will be understood that channels of devices herein can be circular. Hydraulic diameter can be calculated as $DH=4A/P$, where A is the cross-sectional area of the flow, and P is the wetted perimeter of the cross-section. In some embodiments, the hydraulic diameter of the second and third fluid transport channels 5A and 5B are the same or different and between 3/105 to 1/1 the hydraulic diameter of the first fluid transport channel 1A. In certain illustrative embodiments, the hydraulic diameter of the second and third fluid transport channels are the same. In some embodiments, the hydraulic diameter of the second fluid transport channel 5A is between 1/6 and 1/1 the hydraulic diameter of the third fluid transport channel 5B. In illustrative embodiments, the hydraulic diameter of the second and third fluid transport channels 5A and 5B are the same.

In some embodiments of a device for analyzing a reaction product, one of the aspects provided herein, such as the device depicted in FIG. 15, the device can have a direct fluidic connection between the first fluid transport channel and the reaction well (not shown in FIG. 15). Thus, a device according to these embodiments, can include a direct connection between the first fluid transport channel and the reaction well (i.e. these structures can be in direct fluidic communication) as disclosed herein, for example in relation to other aspects, such as, but not limited to those shown for a device for making nanoparticles as depicted in FIG. 1. In illustrative embodiments of a device for analyzing a reaction product, there is no direct connection between the first fluid transport channel and the reaction well. Accordingly, in illustrative embodiments, the first fluid transport channel is not in direct fluidic communication with the reaction well (as depicted for example, in FIG. 15). In some embodiments of a device for analyzing a reaction product, there is no first fluidic transport channel, but rather the second fluidic transport channel is in direct fluidic communication with the first port at the opposite end from the end of the second fluidic transport channel that is in direct contact (direct fluidic communication) with the interface channel segment.

A microfluidic device for detecting a reaction product typically includes a passive pressure sensing channel as illustrated as part 3A of FIG. 15. The passive pressure sensing channel 3A can be adapted for, designed to, and/or effective for measuring the amount or flow-inhibiting strength of a reaction product (e.g. precipitate) in one of the other channels of the device, especially the second fluid transport channel 5A, the interface channel 5C, and/or the fluidic constriction channel 4. For the passive pressure sensing channel to function, typically the reaction well 2 contains the first fluid. When a first fluid is trapped in the reaction well 2 of the device, a fluid-air interface forms in the passive pressure sensing channel 3A that exhibits an inherent capillary pressure. This capillary pressure relies directly on the surface tension of the first fluid, the contact angle of the first fluid with the device material, and the dimensions of the passive pressure sensing channel 3A.

The passive pressure sensing channel can be in fluid contact with the reaction well 2 at various regions of the reaction well 2. In illustrative embodiments, the passive pressure sensing channel is in fluid contact with the reaction well 2 at a side of the reaction well 2 opposite a side of the reaction well in fluid communication with the fluidic constriction channel 4. In illustrative embodiments, as illustrated in FIG. 15, the passive pressure sensing channel 3A extends from the reaction well 2 opposite the fluidic constriction channel 4 and terminates at the passive pressure sensing channel port 3. In illustrative embodiments, the passive pressure sensing channel 3A has a smaller width (e.g. 1/20 to 1/1.5 or 1/10 to 1/1.5 or ⅕ to ½) compared to the width of the interface channel, the second fluid transport channel and the third fluid transport channel, such that the hydrodynamic resistance of the passive pressure sensing channel 3A is at least 1.01 times the hydrodynamic resistance of each of the interface channel segment, the second fluid transport channel and the third fluid transport channel. In illustrative embodiments, the hydrodynamic resistance of the passive pressure sensing channel 3A is between 1.01 and $5\times10^7$, 1.5 and $4.8\times10^7$, 2 and $1\times10^5$, 10 and $1\times10^3$, or 10 and 100 times the hydrodynamic resistance of each of the interface channel segment, the second fluid transport channel and the third fluid transport channel.

In illustrative embodiments, the passive pressure sensing channel 3A terminates at the second port 3. A skilled artisan will understand that a passive pressure sensing channel can have various geometries, segments, and angles between segments provided that it can perform the function provided herein. For example, a passive pressure sensing channel can be a straight channel, or can include at least one, or have between 1 and 10, 1 and 5, or 1 and 2, or 1 bend, rounded orientation, and/or curve. In some embodiments, a passive pressure sensing channel includes at least two segments, wherein at least a first segment extends horizontally or at an angle from the reaction well 2, and at least one second segment extends from the first segment at other than a straight line. In illustrative embodiments, at least one second segment extends from the first segment at an angle of between 1 and 180 degrees, 30 and 160 degrees, 40 and 130 degrees, 40 and 120 degrees, or 45 and 130 degrees with respect to the first pressure sensing channel segment. In other embodiments, a passive pressure sensing channel comprises at least three segments, wherein at least a first segment extends horizontally or at an angle from the reaction well 2, at least one second segment extends from the first segment at other than a straight line and optionally at an angle of between 1 and 180 degrees, 30 and 160 degrees, 40 and 130 degrees, 40 and 120 degrees, or 45 and 130 degrees with respect to the first segment, and at least one third segment extends from the second segment at other than a straight line and optionally at an angle of between 1 and 180 degrees, 30 and 160 degrees, 40 and 130 degrees, 40 and 120 degrees, or 45 and 130 degrees with respect to the second segment.

In some embodiments the second fluid transport channel 5A extends from the third fluid transport channel 5B at an angle of between 1 and 180 degrees. In illustrative embodiments, the second fluid transport channel 5A, the interface channel segment 5C and the third fluid transport channel 5B together form a straight or other than straight fluidic path.

Typically, the fluidic constriction channel 4 is at an angle relative to the second and/or third fluid transport channels (5A, 5B). For example, the angle can be between 25 and 155 degrees, 30 and 145 degrees, 45 and 135 degrees, 60 and 120 degrees. In certain illustrative embodiments, the angle is between 70 and 110 degrees, 80 and 100 degrees, 85 and 95 degrees, 88 and 92 degrees, about 90 degrees, or 90 degrees.

The hydrodynamic resistance ratios of channels within a microfluidic device for detecting a reaction product, such as that illustrated in FIG. 15, are typically effective for, operable for, adapted for, and/or provide that when the first fluid transport channel, the second fluid transport channel, the interface channel segment, the fluidic constriction channel, the reaction well, and optionally a portion of the third fluid transport channel, are filled with a fluid, and a negative pressure is applied at the first port for a period of time or a positive pressure is applied at the third port for a period of time, the fluid is trapped in the reaction well and optionally the fluidic constriction channel, but removed from the rest of the device.

In some embodiments, the hydrodynamic resistance ratios of channels within a microfluidic device for detecting a reaction product, such as that illustrated in FIG. 15, are as follows: the passive pressure sensing channel has 1.01 to $5 \times 10^2$, 1.01 to $4.8 \times 10^2$, 10 to $1 \times 10^6$, 100 to $1 \times 10^4$, or 100 to $1 \times 10^3$, times the resistance of the second or third fluid transport channels; the fluidic constriction channel has $4.0 \times 10^{-6}$ to 2.5, $1 \times 10^{-4}$ to 1, $1 \times 10^{-3}$ to 0.1, or $1 \times 10^{-3}$ to $1 \times 10^{-2}$ times the resistance of the second or third fluid transport channels; the fluidic constriction channel has $2 \times 10^{-4}$ to 700, $2 \times 10^{-3}$ to 100, $2 \times 10^{-2}$ to 10, or $2 \times 10^{-1}$ to 1 times, the resistance of the reaction well; the reaction well has $7 \times 10^{-3}$ to 0.99, $7 \times 10^{-5}$ to 0.1, $7 \times 10^{-3}$ to 0.01 times the resistance of the second or third fluid transport channel; and/or the first fluid transport channel has $2.5 \times 10^{-6}$ to 25, $1 \times 10^{-5}$ to 1, $1 \times 10^{-4}$ to 0.1, or $1 \times 10^{-4}$ to $1 \times 10^{-2}$ times the resistance of the second or third fluid transport channel.

The fluidic constriction channel 4 in embodiments of a device for detection a reaction product, such as that illustrated in FIG. 15, can have dimensions and a physical makeup similar to fluidic constriction channels of other devices disclosed herein. For example, the fluidic constriction channel can be composed of a neutral or slightly hydrophilic material. In illustrative embodiments, the fluidic constriction channel 4 is comprised of a hydrophobic material.

In some embodiments of a microfluidic device for detecting a reaction product, such as that illustrated in FIG. 15, the microfluidic device has a precipitate therein. For example the second fluid transport channel, the third fluid transport channel, the interface channel segment, the channel, and/or the second fluid transport channel, can include a precipitate therein. In illustrative embodiments, at least the second fluid transport channel comprises a precipitate therein.

In some embodiments, the reaction well 2 and optionally the fluidic constriction channel 4 of a microfluidic device for detecting a reaction product, such as that illustrated in FIG. 15, are filled with fluid, but the rest of the device is empty. The volume of the reaction well has a volume of between 1 nl and 450 nl, 5 nl and 250 nl, 5 nl and 100 nl, 10 nl 50 nl or between 15 and 35 nl.

In some embodiments, this disclosure provides microfluidic assemblies comprising at least two of the fluidic devices illustrated in FIGS. 15-19 (e.g., fluidic device subunits). In some embodiments, the microfluidic assembly comprises an array of between 2 and 256 of such fluidic devices, optionally between 4 and 64 of the devices. In some embodiments, the fluidic device subunits of the array are not fluidly connected, and in some embodiments these are fluidly connected. In some embodiments, less than all of the fluidic device subunits may be fluidly connected to one another. In some embodiments, multiple microfluidic assemblies are fluidly connected to one another. In some embodiments, the fluidic device subunits (or microfluidic assemblies) of the array are grouped into two or more groups, wherein devices of the same group are fluidly connected. In some embodiments, fluidic devices that are fluidly connected can comprise a first port and/or a third port that functions as the third port or first port respectively of the next device in fluid communication in the group; or wherein the first port may serve as a universal first port for all of the devices in the group or each device will have an independent first port, and the third port may serve as the universal third port for all devices in the group or each device will have an independent third port. In some embodiments, the microfluidic assembly is a disposable cartridge. Other embodiments of microfluidic assemblies are also possible as would be understood by those of ordinary skill in the art.

Certain aspects provided herein, are methods for detecting, measuring, forming, or analyzing a reaction product, in illustrative embodiments, a precipitate, or methods for detecting whether a first fluid and a second fluid react, or methods for detecting whether components of a first fluid react with components of a second fluid, or methods for detecting an interaction of a first fluid and a second fluid, using a device referred to herein as a microfluidic device for detecting a reaction product, for example as illustrated in FIG. 15. Such methods in the following paragraphs, for ease of reference will be referred to as methods for detecting a reaction product. Part numbers referenced in the following paragraphs related to methods for detecting a reaction product are shown in FIG. 15. A skilled artisan will identify these parts in FIGS. 16 to 19 as well, regardless of whether they are explicitly identified in those figures. Such methods can involve the following steps: a. introducing a first fluid into the device typically through the first port; b. trapping a volume of the first fluid in the reaction well 2, in illustrative embodiments by capturing a droplet of a volume, optionally a pre-defined volume, of the first fluid in the reaction well 2; c. introducing a second fluid (i.e. a second solution) into the device so that it can interact with the trapped volume of the first fluid. typically into third fluid transport channel 5B and the interface channel segment 5C, typically through the third port 6 such the first and second fluids mix in at least part of the interface channel segment 5C and/or the fluidic constriction channel 4 to form a reaction product of one or more components of the first fluid and one or more components the second fluid; and optionally, but typically d. detecting the reaction product.

The step of introducing a first fluid into the device, or filling the fluidic device with the first fluid, is an optional step, since it is envisioned that a device could be supplied to a user wherein the reaction well is pre-filled, for example. In some embodiments, filling the fluidic device with the first fluid is accomplished by using a positive pressure to inject the first fluid through the first port. In this step typically a volume of a first solution including one or more test compound(s) or compound(s) of interest (e.g., members of a library of candidate compounds, or a potential anti-perspirant solution) is loaded into the device, for example through the first port. In some embodiments, between 0.1 µl and 1 ml, 1 µl and 500 µl, 1 µl and 200 µl and 100 µl and 25 µl and 1 µl 10 µl about 5 µl or 5 µl of the first fluid is introduced into the device in this step.

The step of introducing a second fluid (i.e. a second solution) into the device so that it can interact with the trapped volume of the first fluid typically involves delivering the second fluid into the third fluid transport channel 5B and the interface channel segment 5C, typically thru the third port 6. The second fluid can be introduced into the third fluid transport channel at a flow rate of between 0.01 nl/min and 1 ml/min, 0.05 nl/min and 100 µl/min, 0.05 nl/min and 50 µl/min, 1 nl/min and 25 µl/min, 100 nl/min and 1 µl/min, 1 µl/min and 100 µl/min, or 1 µl/min and 10 µl/min, for example.

The composition of the second fluid is not intended to be limited, and can include, as a non-limiting example, members of a candidate compound library, nucleic acids, proteins, carbohydrates or lipids. Furthermore, the composition of the first fluid and the second fluid can be switched. In other embodiments, mammalian sweat, an artificial sweat, or other sweat-based compound can be the second compound. A sweat-based compound can be any fluid designed to mimic sweat containing critical sweat compounds, including but not limited to artificial sweat and/or simulated body fluid including a variety of dissolved salts in distilled water along with a small amount of BSA as a model protein (e.g., between 0.01 and 1% BSA). As a result, of introducing the second fluid into the device, the first and second fluids mix in at least part of the interface channel segment 5C and/or the fluidic constriction channel 4 to form a reaction product of one or more components of the first fluid and one or more components the second fluid.

In some illustrative embodiments, formation of the reaction product results in an increase in pressure in at least one channel within the device, and the increased pressure is detected. In some embodiments, the reaction product forms a plug, such as a precipitate plug, that blocks flow through one or more channels of the devices and in illustrative embodiments, this blockage of flow is detected and/or measured using the passive pressure sensing channel 3A. For example, in the case of sufficient pressure building up in the device such that fluid flows into and optionally exits the passive pressure sensing channel 3A, this fluid can be detected and optionally measured, thus detecting the formation of the plug and optionally providing the ability to measure the strength of the blockage caused by the plug.

In certain embodiments, prior to the introduction of the second fluid into the third fluid transport channel 5B, the passive pressure sensing channel 3A is filled with air and does not comprise fluid, such that a fluid-air interface is present at the point at which the reaction well 2 and the passive pressure sensing channel 3A connect. Thus, the passive pressure sensing channel forms a sensitive sensor that is capable of, adapted for, and/or designed to measure the strength of pressure build-up in the device upon formation of a reaction product that inhibits flow in the device, for example inhibiting flow in the second transport channel, the interface channel segment, the fluidic constriction channel, the first transport channel, and/or the third transport channel. Such reaction product can be a thickened fluid, a gel, a polymer, a hardened product, an aggregated product, and in illustrative embodiments, a precipitate. In some embodiments, a camera is used to visualize and record the formation of a thickened fluid, a gel, a polymer, a hardened product, an aggregated product, and in illustrative embodiments, a precipitate. In some embodiments, a physical reaction product may not result from the mixing of the fluids, but the interaction between the two fluids is still important to monitor (e.g., visually or by analyzing the flow of fluids). Video images can then be analyzed using known methods for analysis and measurement of such structures for example using detection systems similar to those discussed herein for microfluidic devices for producing a reaction product such as particles. In further illustrative embodiments, the reaction product forms a plug that stops flow through at least one of the channels of the device, for example the second fluid transport channel, the interface channel segment, or the fluidic constriction channel. In other embodiments, the reaction product that forms is a fluorescent product, a colored product, or exhibits a change of color, any of which can be detected.

Various instruments for detecting the reaction product can be employed. For example, a camera, in illustrative embodiments, a video camera, can be optically connected to any channel in the device, and in illustrative embodiments is optically connected to the interface channel segment, the fluidic constriction channel, the second fluid transport channel, and/or the passive pressure sensing channel. An exemplary of the above methods is provided below.

Figure 16A:
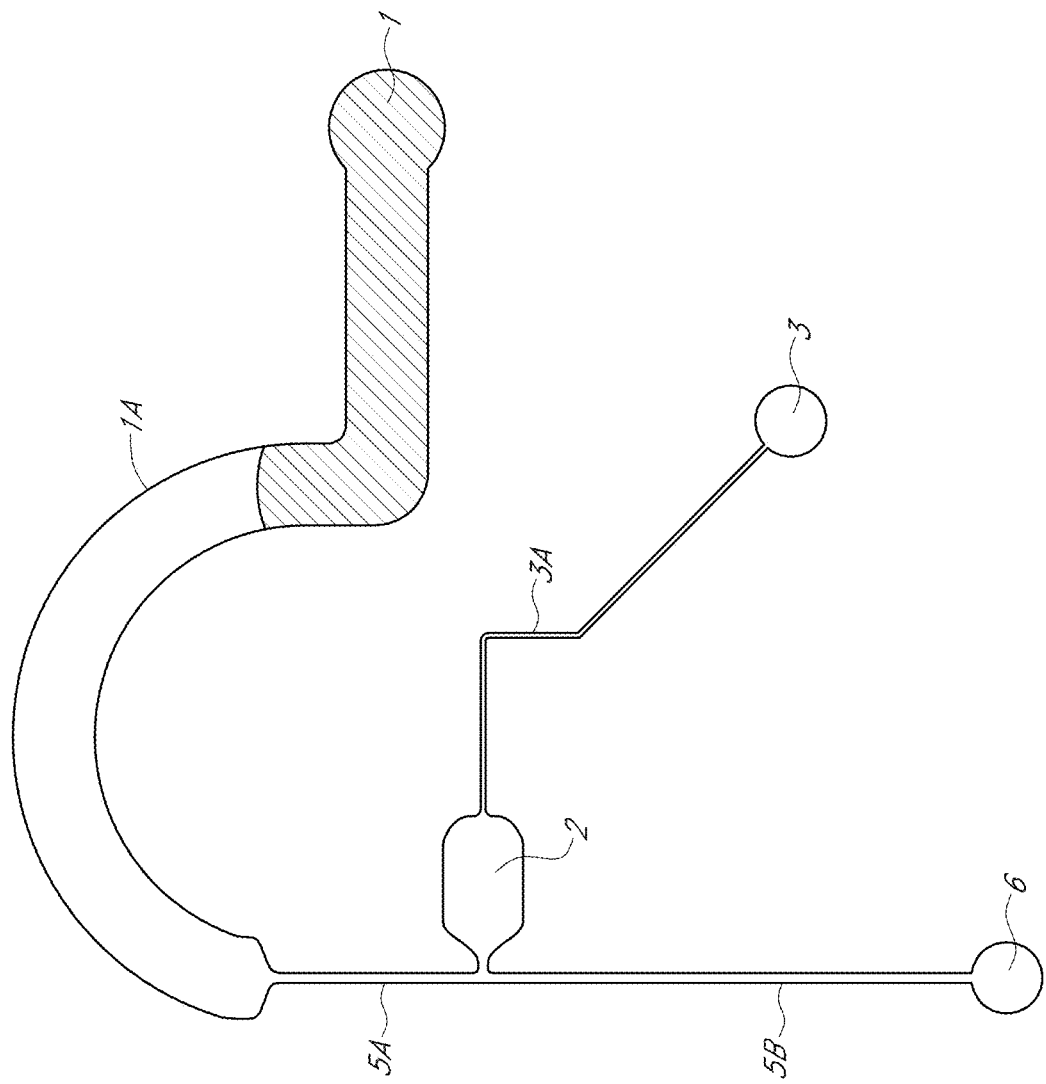
FIGS. 16A-16C provide diagrams illustrating fluid flow while filling a device according to FIG. 15.
Figure 16B:
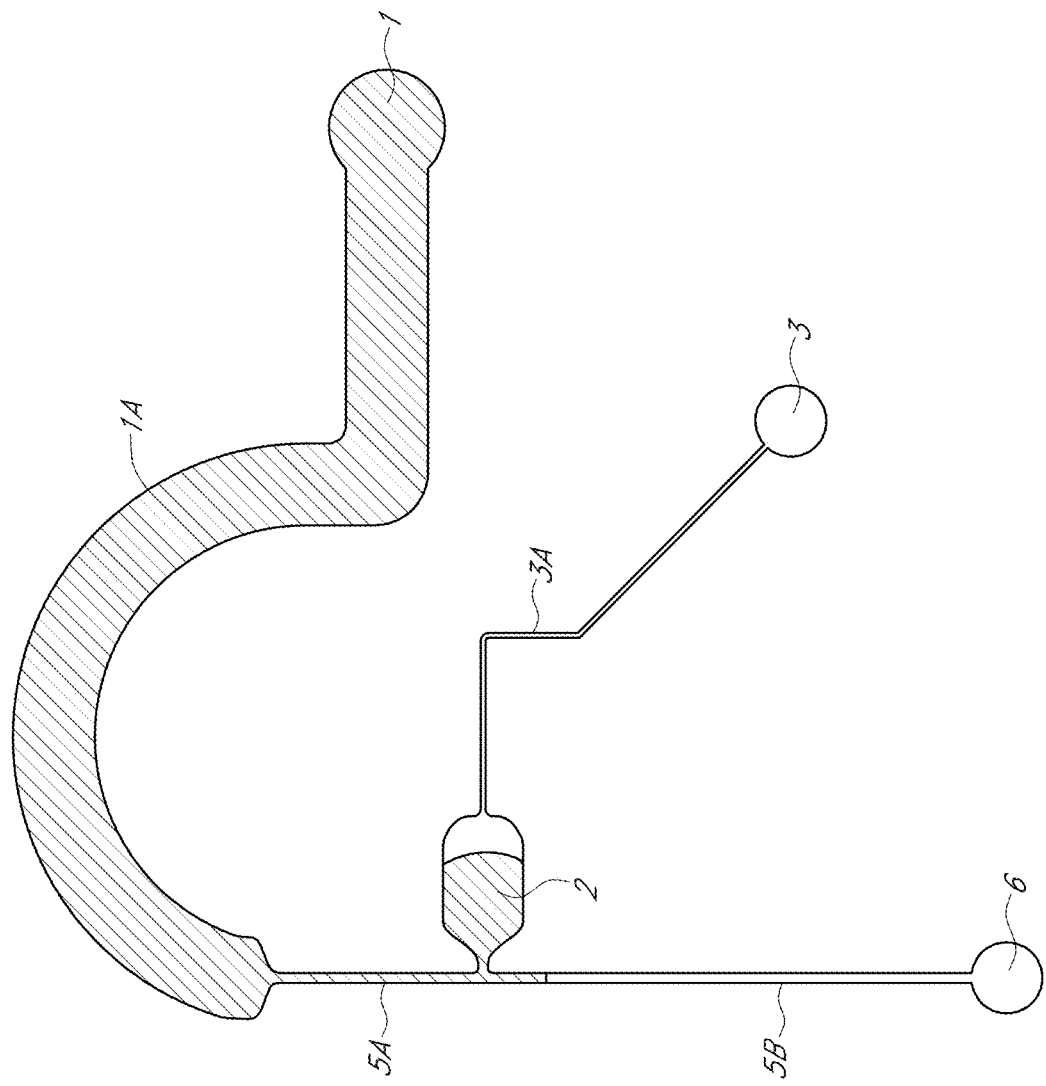
Figure 16C:
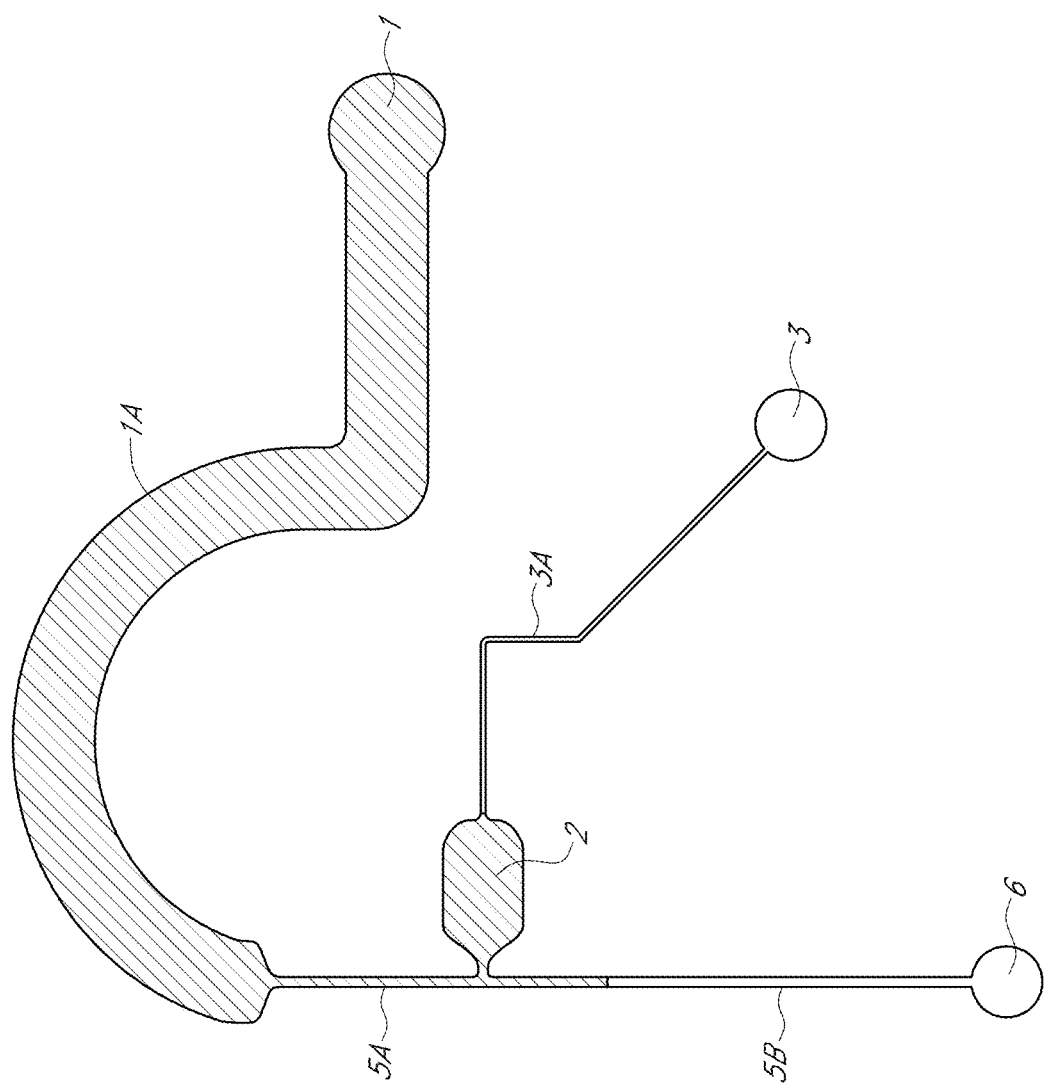

Introduction of a First Fluid (see FIGS. 16 (steps A-C) and 17 (step A))

An exemplary method for detecting a reaction product is explained with reference to parts as labeled in FIG. 15. Initially, the first fluid (i.e. the fluid to be captured in the device (i.e. trapped in the reaction well)) is introduced into the device. Fluid entry for this initial loading, in this illustrative example, occurs at the first port 1. A first fluid is passed through this port via positive applied pressure and into the first fluid transport channel (1A, e.g., section 1A1) (FIG. 16 step A). is noteworthy that in illustrative embodiments of this device aspect shown in FIG. 15, that the first fluid transport channel is not in direct fluidic communication with the reaction well. Fluid continues moving through the first fluid transport channel (e.g., from 1A1 into 1A2) into the second fluid transport channel 5A, where it then reaches the interface channel segment 5C followed by the third fluid transport channel 5B. At this point, fluid begins to fill the fluidic constriction channel 4, reaction well 2 and the third fluid transport channel 5B, based in large part by the ratio of hydrodynamic resistances between these parts (FIG. 16 step B). In the illustrative embodiment shown in FIG. 15, the continuous channel formed by the third fluidic transport channel 5B, the interface channel segment 5C, and the second fluid transport channel 5A forms a T junction. Upon completion of filling of the reaction well 2, fluid reaches the entrance to the passive pressure sensing channel 3A and rests at its opening, forming a fluid-air interface. Not to be limited by theory, this fluid-stopping phenomenon (i.e., formation of a fluid-air interface) during initial fluid loading is due to the higher hydrodynamic resistance of the passive pressure sensing channel 3A and higher capillary pressure induced by the passive pressure sensing channel 3A in comparison to the second and third fluid transport channels (5A and 5B). At this stage for this illustrative method, the first fluid transport channel 1A, second fluid transport channel 5A, fluidic constriction channel 4, and reaction well 2, are full of fluid, and the passive pressure sensing channel 3A and optionally the third fluid transport channel 5B are partially full (FIG. 16 step A and 17 step A).

Figure 17A:
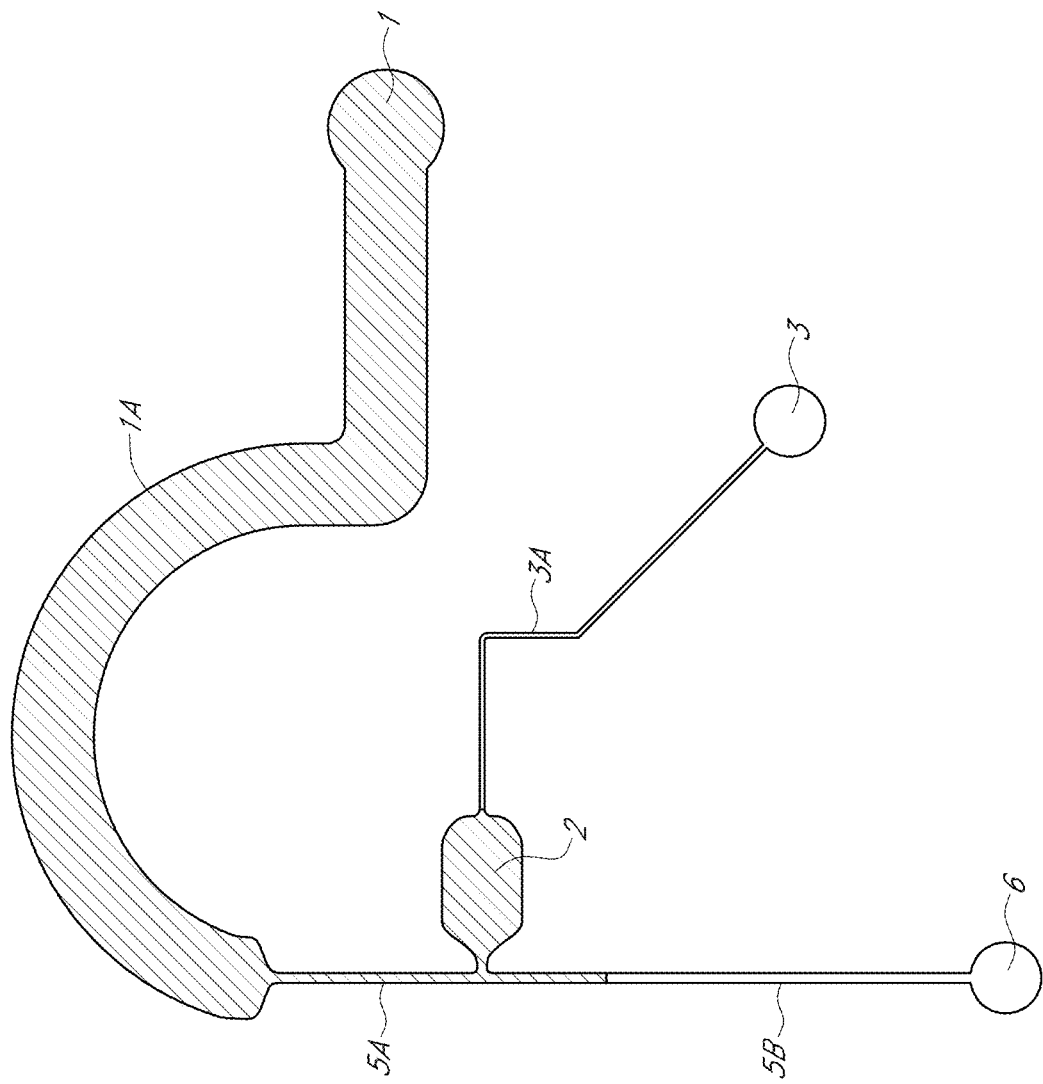
FIGS. 17A-17C provide diagrams illustrating fluid flow when fluid is withdrawn from a device according to FIG. 15.
Figure 17B:
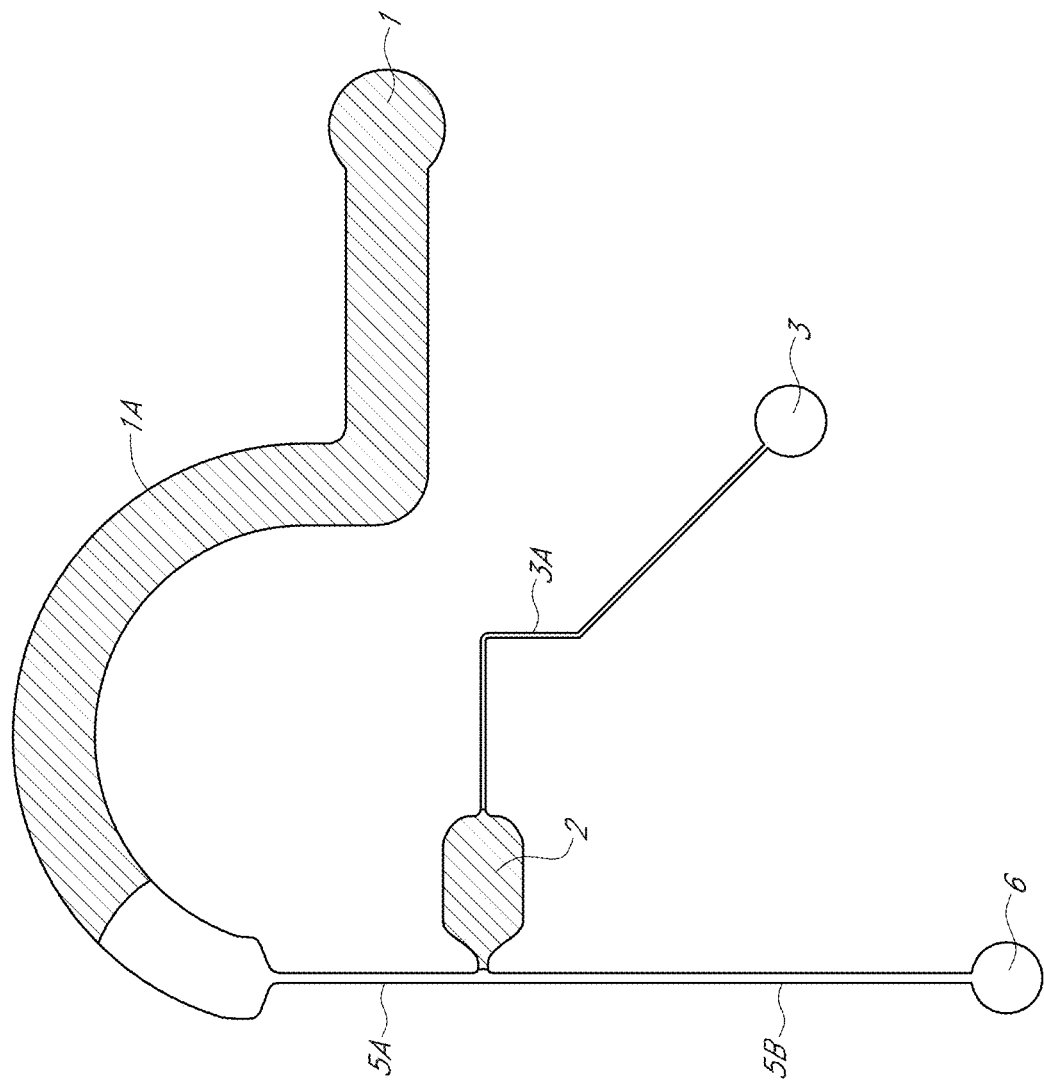
Figure 17C:
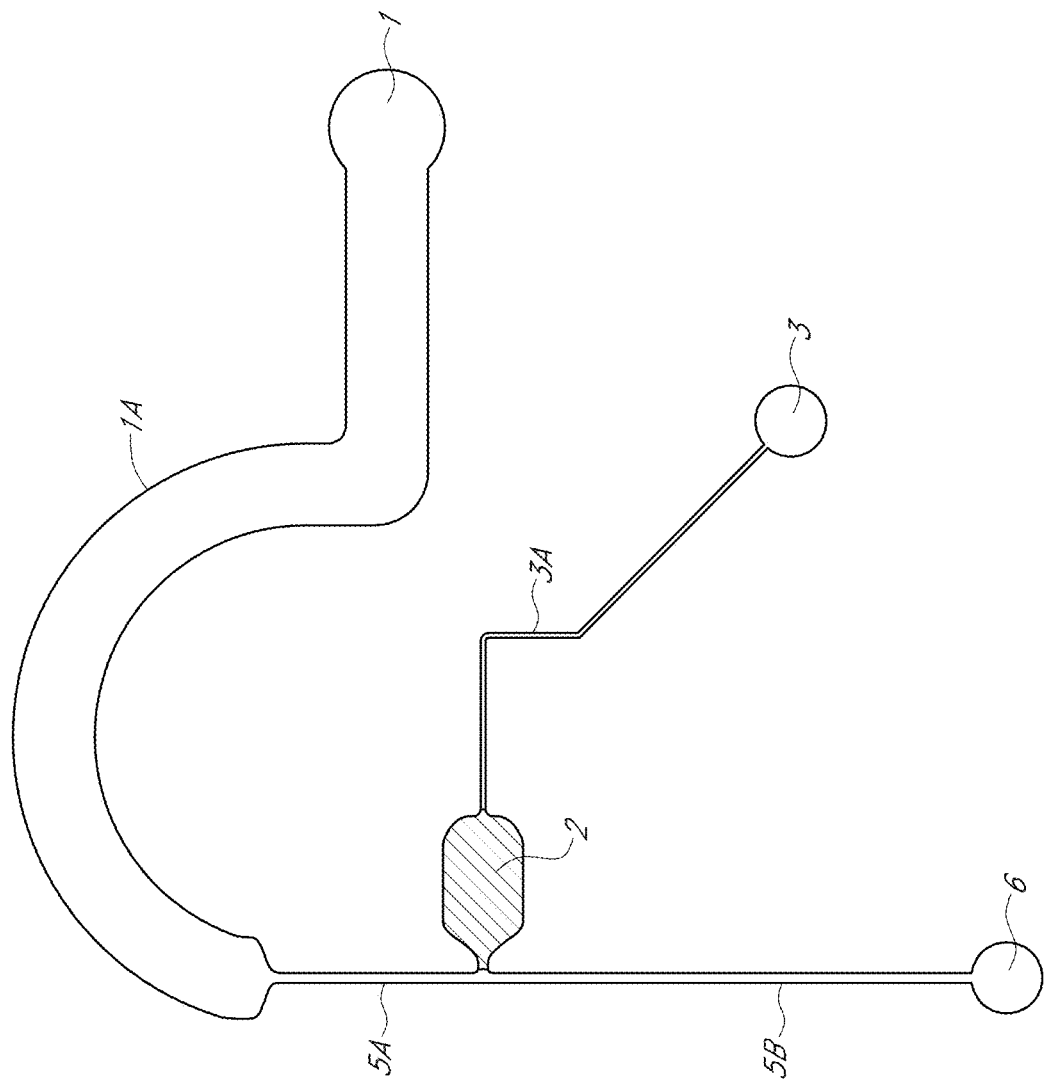
Figure 18A:
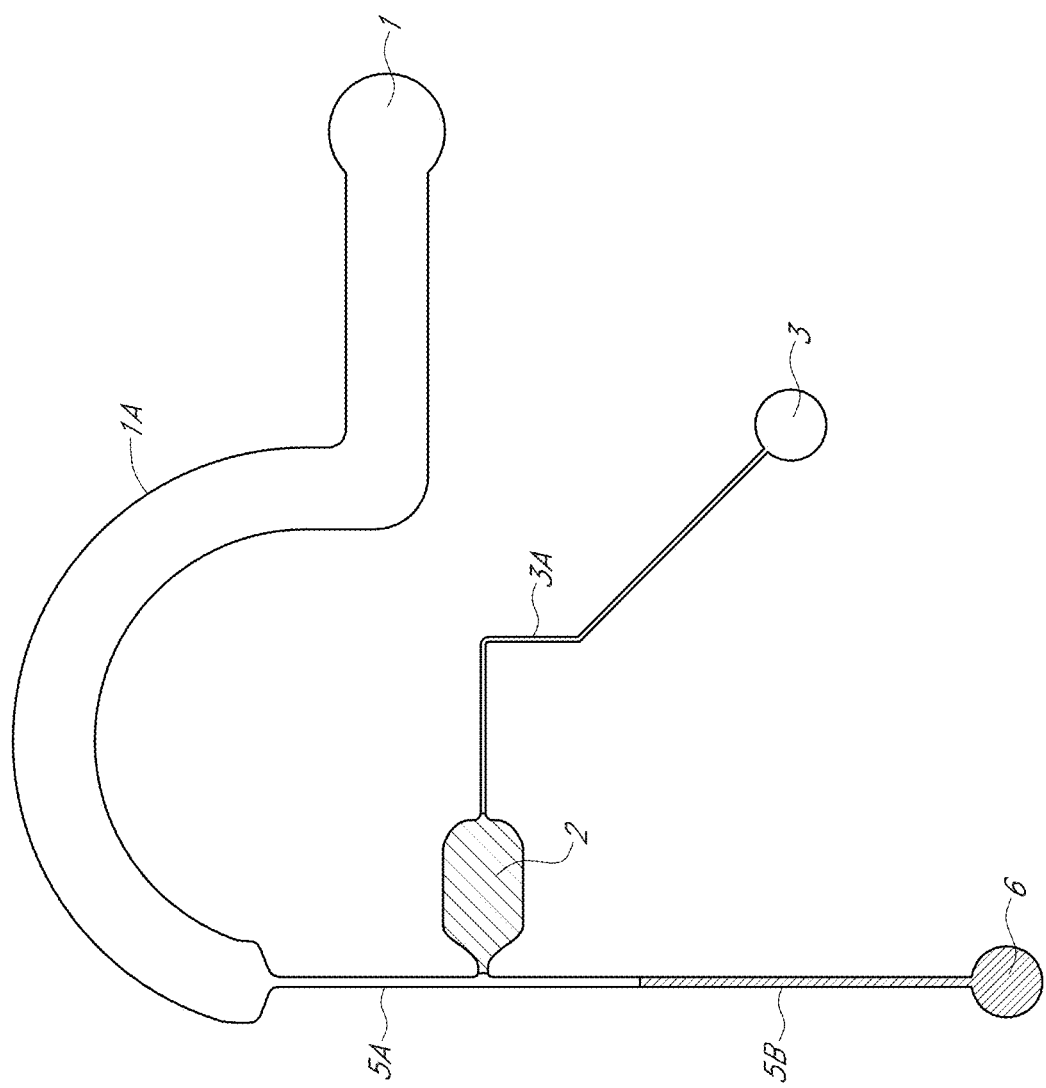
FIGS. 18A-18D provide diagrams illustrating steps in an embodiment for using the device according to FIG. 15. Top left panel
Figure 18B:
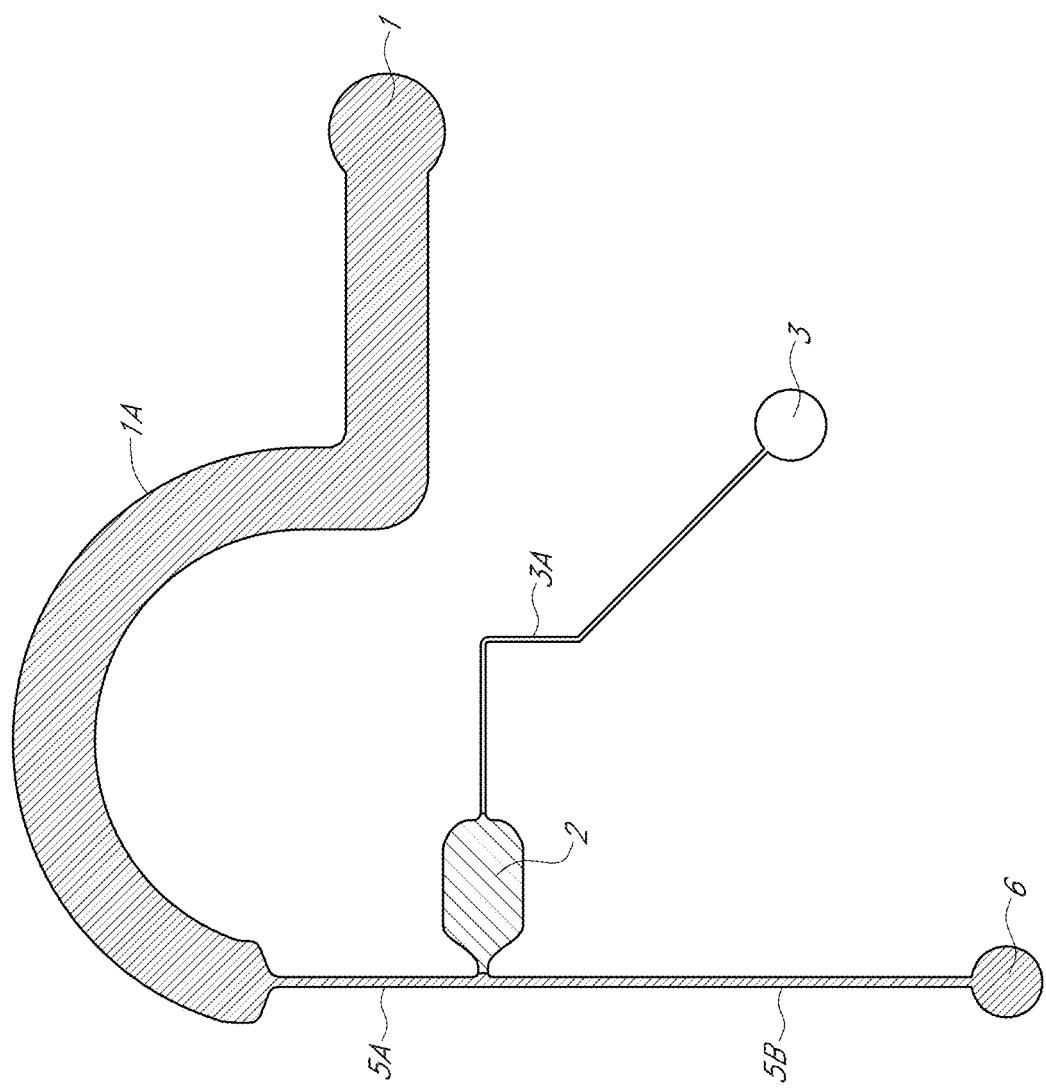
Figure 18C:
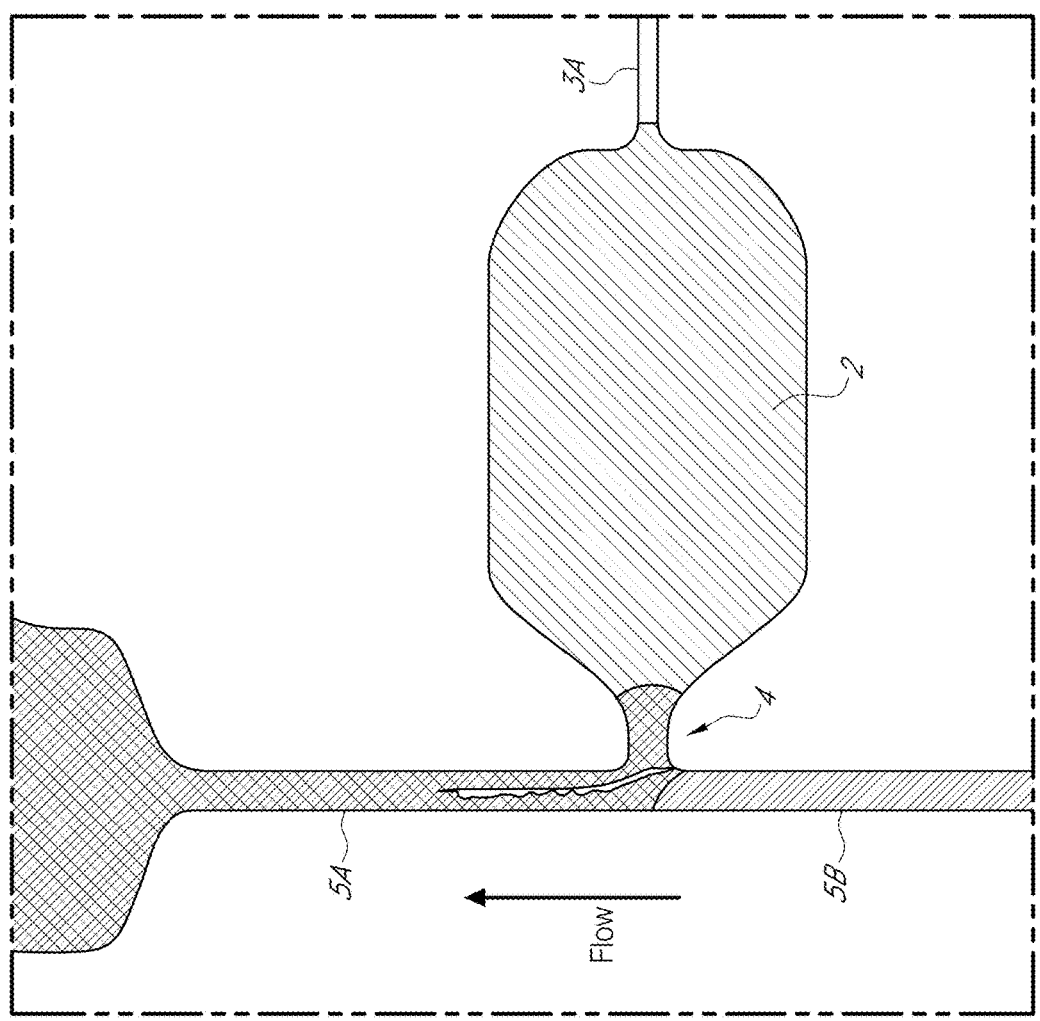
Figure 18D:
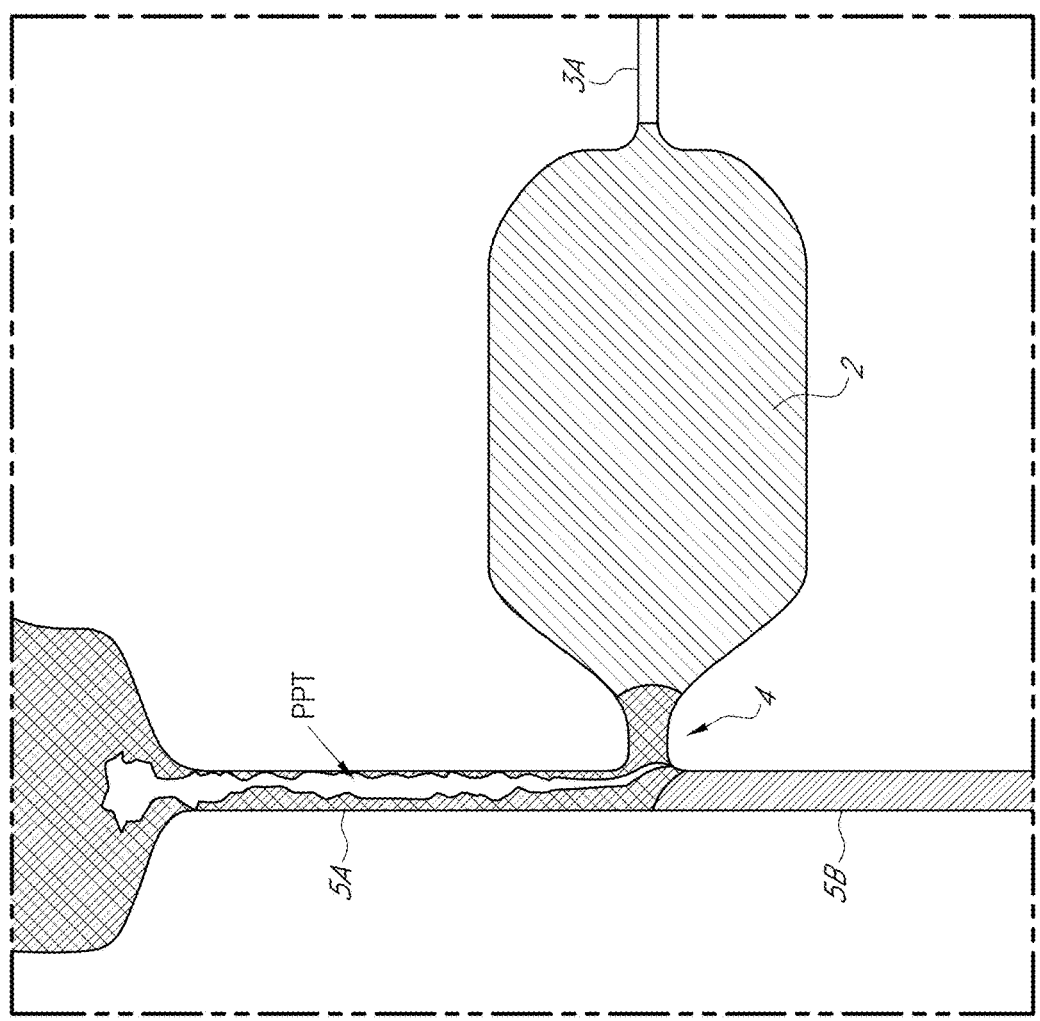

Droplet Capture of the First Fluid (see FIG. 17 Steps A-C)

After initial introduction of the desired first fluid into the device, excess fluid is typically removed to initiate capture of a volume (e.g. droplet capture) of the first fluid in the device. Droplet capture in this device is passive in nature; due to the constructed geometry of the device, as illustrated in FIG. 15 and FIG. 17 steps A-C, a reproducible volume of the first fluid is captured in the reaction well. To initiate droplet capture, excess fluid is typically removed from the device, and a negative pressure is applied at the first port 1. Fluid retreats from the first fluid transport channel 1A in a direction opposite to its loading direction (i.e., fluid retreats towards the first port 1). Due to the geometry of the device, and specifically the geometry of parts 2, 3A, 4, 5A, 5B, and/or 5C as identified in FIG. 15, fluid in the reaction well 2 (and fluidic constriction channel 4) does not retreat towards the first port 1 and remains in the reaction well 2 (FIG. 17 step B). The geometry of the device includes the dimensions of the device. The width, length, and depth of each channel play a role in the hydrodynamic resistance of each channel. The ratios of hydrodynamic resistances between channels play a role in the movement of fluid in the device and in the capture of the first fluid in the reaction well. Thus, the reaction well 2 remains full of the first fluid, while excess fluid continues to retreat from the third fluid transport channel 5B thru the interface channel segment 5C to the second fluid transport channels 5A, to the first fluid transport channel (through the curved section 1A2 and straight section 1A1), and the first port 1 until only the reaction well 2 and fluidic constriction channel houses any liquid in the system (FIG. 17 step C) (i.e., a first fluid droplet is captured and housed in the reaction well 2) and fluid connection channel 4). In other embodiments, a positive pressure is applied from the third port instead of a negative pressure from the first port to capture a volume of the first fluid in the reaction well 2.

Introduction of Second Fluid and On-Device Reaction with First Fluid (see FIG. 18)

A second fluid is then introduced into the device to interact with the first fluid droplet captured and housed in the reaction well 2. This second fluid is passed through the third port 6 via a positive applied pressure and enters the third fluid transport channel 5B (FIG. 18 panel A). As fluid passes through part 5B, it reaches the interface channel segment 5C and the opening of the reaction well 2 (at fluidic constriction channel 4), where a fluid-air interface of the first fluid exists. The incoming second fluid meets with and interacts with (i.e., mixes with) the first fluid housed in the reaction well 2 and fluidic constriction channel 4. Mixing of the first fluid and second fluid first occurs in the interface channel segment 5C, the fluidic constriction channel 4 and in the entrance to the reaction well 2 at the junction between the fluidic constriction channel 4 and the reaction well 2. Mixed first fluid and second fluid continues to flow from the interface channel segment 5C towards the second fluid transport channel 5A. This mixed fluid continues to flow from the second fluid transport channel 5A to and through the first fluid transport channel 1A and finally to the first port 1, where fluid exits the device (FIG. 18 panel B). The second fluid is introduced into the device through the third port 6 for a variable period of time and in variable volume, depending on the particular use. It is noteworthy that in illustrative embodiments of the device aspect provided in FIGS. 15-18 herein, the fluidic constriction channel 4 allows for mixing of fluids but does not promote complete washing and/or quick complete fluid replacement.

If compounds in the first and second fluids interact to form a precipitate (e.g, a plug), that precipitate will mainly form in the fluidic constriction channel 4 at the opening of the reaction well 2, in the interface channel segment 5C, and/or in the second fluid transport channel 5A (FIG. 18 panel C). In general, this precipitation plug will grow over time as the first and second fluids continue to mix and interact. The growth profile of the precipitation plug depends on the nature of the second fluid, the nature of the first fluid, the temperature of the device, the flow rate of the incoming second fluid, and theoretically the humidity of the device. The growth rate also partially depends on the sizes of the second and third fluid transport channels, the interface channel segment, the fluid connection channel, and the reaction well. If the reaction well has a larger opening as opposed to a smaller opening, there will be more mixing of the first and second fluids. It Is believed that this different mixing volume and mixing rate could have an effect on precipitate formation as well. As the precipitate plug grows over time, in some cases it blocks the flow of the second fluid through the second fluid transport channel 5A (FIG. 18 panel D) (i.e., it inhibits incoming flow of second fluid towards the first port 1), thus increasing pressure buildup within the device. This pressure buildup is exerted on the fluid in the reaction well 2 and is thus also exerted on the fluid-air interface located at the entrance of the passive pressure sensing channel 3A. This fluid-air interface in the passive pressure sensing channel exhibits an inherent capillary pressure. This capillary pressure relies directly on the surface tension of the first fluid, the contact angle of the first fluid with the device material, and the dimensions of the passive pressure sensing channel 3A. As the pressure buildup induced by the precipitate plug increases and exceeds the above-mentioned capillary pressure, it overcomes the capillary pressure holding the fluid interface at the beginning of passive pressure sensing channel 3A. When this occurs, fluid begins to flow through the passive pressure sensing channel 3A and out of the device through the second port 3, where it can be detected (e.g., visually such as by eye or by using an imaging device such as a camera). For instance, one can analyze recorded time lapses focused on the reaction well/fluid transport channels/passive pressure sensing channel (e.g., using a camera and a fluid interface tracking algorithm) and time stamp the moment when fluid begins to enter the pressure sensing channel, and/or photodiodes can be positioned in the pressure channel and used in conjunction with a camera to detect fluid entry. As the value of the inherent capillary pressure in the passive pressure sensing channel 3A can be determined for a given fluid, the flow of fluid through it provides a built-in indicator of precipitate plug strength. The capillary pressure exhibited by the fluid resting at the beginning of passive pressure sensing channel 3A can be modified by changing the depth and width of the channel (e.g., using the ranges listed below or any other suitable depth and/or width). Thus, by modifying the dimensions of the passive pressure sensing channel 3A, this built-in pressure sensor can be adjusted to match pressures that may be relevant in different industrial fields. Non-limiting, exemplary ranges of suitable dimensions for the passive pressure sensing channel 3A are shown in Table 2.

EXEMPLARY EMBODIMENTS

Provided in this Exemplary Embodiments section are exemplary aspects and embodiments provided herein and further discussed throughout this specification. For the sake of brevity and convenience, all of the disclosed aspects and embodiments and all of the possible combinations of the disclosed aspects and embodiments are not listed in this section. It will be understood that embodiments are provided that are specific embodiments for many aspects, as discussed in this entire disclosure. It is intended in view of the full disclosure herein, that any individual embodiment recited below or in this full disclosure can be combined with any aspect recited below or in this full disclosure where it is an additional element that can be added to an aspect or because it is a narrower element for an element already present in an aspect. Such combinations are discussed more specifically in other sections of this detailed description.

Provided herein in one aspect is a fluidic device, comprising:
a) a first port;
b) a first fluid transport channel in fluid connection with:
  i. the first port;
  ii. a reaction well; and,
  iii. an overflow channel;
c) a second fluid transport channel in fluid communication with the overflow channel;
d) a fluidic constriction channel in fluid communication with the reaction well and the second fluid transport channel; and
e) a second port in fluid communication with the second fluid transport channel.

Provided herein in another aspect is a fluidic device assembly, comprising at least two microfluidic devices in a disposable cartridge, wherein each fluidic device comprises:
a) a first port;
b) a first fluid transport channel in fluid connection with:
  i. the first port;
  ii. a reaction well; and,
  iii. an overflow channel;
c) a second fluid transport channel in direct fluid communication with the overflow channel;
d) a fluidic constriction channel in direct fluid communication with the reaction well and the second fluid transport channel; and
e) a second port in direct fluid communication with the second fluid transport channel.

In some embodiments of the fluidic device assembly aspect immediately above, the at least two microfluidic devices are connected in serial. In some embodiments of the fluidic device assembly aspect immediately above, the at least two microfluidic devices are connected in parallel.

In another aspect, provided herein is a fluidic device assembly, comprising a series of fluidic devices, wherein each fluidic device of the series comprises:
a first fluid transport channel in direct fluid communication with a reaction well and an overflow channel;
a second fluid transport channel in direct fluid communication with the overflow channel; and
a fluidic constriction channel in direct fluid communication with the reaction well and the second fluid transport channel, wherein:
  the first fluid transport channel of a first fluidic device in the series is in fluid communication with at least a first port channel and a second port channel, wherein said first port channel and said second port channel terminate in a first port channel port and typically a second port channel port, respectively;
  a second fluid transport channel of the first fluidic device in the series is in fluid communication with a first fluid transport channel of a second fluidic device in the series;
  the second fluid transport channel in the second fluidic device in the series, and subsequent devices in the series if present, are in fluid communication with the first fluid transport channel of the next fluidic device in the series; and
  typically, the second fluid transport channel of the last fluidic device in the series terminates in an outlet port.

In some embodiments of the fluidic device assembly aspect immediately above, the first port channel is filled with a lipid in an organic solvent or a polymer dissolved in a solvent, and wherein the second port channel is filled with an aqueous solution. In some embodiments of the fluidic device assembly aspect immediately above, the first port channel is filled with a protein and the second port channel is filled with a protein precipitant.

In some embodiments of any of the fluidic device or fluidic device assembly aspects herein, including in combination with other embodiments, unless already stated or incompatible with the aspect, the fluidic device or a fluidic device of the fluidic device assembly further comprises a lipid in an organic solvent or a polymer dissolved in a solvent, and an aqueous solution; or wherein the fluidic device further comprises particles. In some embodiments of any of the fluidic device assembly aspects herein, including in combination with other embodiments, unless already stated or incompatible with the aspect, the fluidic device or fluidic device assembly further comprises a protein precipitate.

In some embodiments of any of the fluidic device assembly aspects herein, including in combination with other embodiments, unless already stated or incompatible with the aspect, the reaction well(s) comprises one or more of one or more lipids, an organic solvent, an alcohol, acetonitrile, a polymer, an aqueous buffer, a mixture thereof, and/or nanoparticles in solution.

In some embodiments of any of the fluidic device assembly aspects herein, especially device assemblies that include multiple fluidic devices in series, including in combination with other embodiments, unless already stated or incompatible with the aspect, the device assembly can further comprise third, fourth, fifth, etc. fluid transport channels in fluid communication with corresponding third, fourth, fifth, etc. input ports, respectively, and in fluid communication typically through one or more additional channels to one or more reaction wells. Thus, additional input fluids (third, fourth, fifth, etc. fluids) can be input into devices herein to produce more complex mixtures and reaction products, such as more complex particles.

In certain aspects, provided herein are fluidic systems comprising multiple (e.g. 2, 3, 4, 5, 10, 15, 20, etc.) fluidic device assemblies, for example fluidic device assemblies (such as those immediately above) comprising a series of fluidic devices, where the fluidic device assemblies in illustrative embodiments, are fluidly connected or linked in parallel.

In certain aspects, fluidic devices herein that are effective producing particles, provide a system that is effective for, adapted to, and operable to produce different size particles by controlling certain parameters when such fluidic devices are used to produce particles. Such parameters include, for example, a first flow rate of a stream of the first fluid as it introduced into the fluidic device, a second flow rate of a stream of the second fluid as it introduced into the fluidic device, a ratio of the first flow rate to the second flow rate, a combined flow rate of the combined first and second streams, overall dimensions of the fluidic device used to perform a method for producing particles, wherein larger size parts of the fluidic device provide larger particles than smaller size parts, a width of the fluidic constriction channel of the fluid device used to perform a method for producing particles, or combinations thereof.

In another aspect, provided herein is a fluidic device comprising:
a) a first port;
b) a first fluid transport channel in fluid connection with:
  i. the first port;
  ii. a reaction well; and,
  iii. an overflow channel;
c) a second fluid transport channel in fluid communication with the overflow channel;
d) a fluidic constriction channel in fluid communication with the reaction well and the second fluid transport channel; and
e) a second port in fluid communication with the second fluid transport channel, wherein the fluidic device comprises in the reaction well, an aqueous solution and either a lipid in an organic solvent or a polymer dissolved in a solvent;
  wherein the fluidic device further comprises particles; or
  wherein the fluidic device comprises in the reaction well, a lipid in an organic solvent or a polymer dissolved in a solvent, and an aqueous solution, and the fluidic device further comprises particles.

In another aspect, provided herein is a fluidic device comprising:
a) a first port;
b) a first fluid transport channel in fluid connection with:
  i. the first port;
  ii. a reaction well; and,
  iii. an overflow channel;
c) a second fluid transport channel in fluid communication with the overflow channel;
d) a fluidic constriction channel in fluid communication with the reaction well and the second fluid transport channel; and
e) a second port in fluid communication with the second fluid transport channel, wherein the fluidic device further comprises a protein precipitate.

In some embodiments of any of the fluidic device or fluidic device assembly herein operable to produce, and effective for producing a reaction product, unless already stated therein or incompatible therewith, the fluidic device or fluidic device assembly is in a disposable cartridge. In some embodiments of any of the fluidic device or fluidic device assembly aspects herein, including in combination with other embodiments, unless already stated or incompatible with the aspect, the fluidic device or fluidic device assembly does not comprise a passive air control valve, or comprises a passive air control valve, for example in fluidic communication with a reaction or each reaction well.

In some embodiments of any of the fluidic device or fluidic device assembly herein operable to produce, and effective for producing a reaction product, unless already stated therein or incompatible therewith, the width or effective diameter of the fluidic constriction channel(s) is between 10 µm and 500 µm, 50 µm and 250 µm, 50 µm and 300 µm, 50 µm and 200 µm, or 50 µm and 150 µm, or the width or effective diameter of the fluidic constriction channel(s) is at least 50 µm and smaller than the width or effective diameter of each of the following components: the first fluid transport channel 1A, the reaction well 2, a second fluid transport channel 5A, directly connected to the fluidic constriction channel 4 opposite the reaction well 2, and an overflow channel 3 that connects the first fluid transport channel 1A to the second fluid transport channel 5A as provided herein. In some embodiments, the fluidic constriction channel is less than one-fifth and in some embodiments less than one-sixth, one-seventh, one-eighth, one-ninth, or one-tenth the diameter or width of the above-stated components.

In some embodiments of any of the fluidic device or fluidic device assembly herein operable to produce, and effective for producing a reaction product, unless already stated therein or incompatible therewith, the width, diameter or effective diameter of the fluidic constriction channel(s) is less than, approximately 0.15 to approximately 0.30 times, the width, diameter, or effective diameter of the reaction well.

In some embodiments of any of the fluidic device or fluidic device assembly herein operable to produce, and effective for producing a reaction product, unless already stated therein or incompatible therewith, the reaction well(s) comprises at least one pillar, optionally having a width, diameter, or effective diameter of about 100 um, and optionally a circular, triangular, or rectangular shape.

In some embodiments of any of the fluidic device or fluidic device assembly herein operable to produce, and effective for producing a reaction product, unless already stated therein or incompatible therewith, the reaction well(s) comprises at least two, three, four, five, six, seven, eight, nine, 10, 11, 12, 13, 14, 15 or 16 pillars.

In some embodiments of any of the fluidic device or fluidic device assembly herein operable to produce, and effective for producing a reaction product, unless already stated therein or incompatible therewith, which typically include an overflow channel, unless already stated or incompatible with the aspect, the fluidic device or the fluidic devices within the fluidic device assembly, is/are capable of, adapted to, and/or operable to transform an input laminar flow fluid stream into an unstable flow, but not a turbulent flow.

In some embodiments of any of the fluidic device or fluidic device assembly herein operable to produce, and effective for producing a reaction product, unless already stated therein or incompatible therewith, the reaction well is configured to hold, contain, or retain, operable to hold, contain, or retain, capable of retaining, adapting, or holding, or adapted to hold, contain, or retain a volume between 100 pl and 10 ml, between 1 nl and 10 ml, between 1 µl and 10 ml, between 1 nl and 10 ml, between 1 µl and 450 µl, between 5 nl and 15 nl, between 15 nl and 35 nl, between 100 nl and 1 ml, between 100 nl and 100 µl, between 1 µl and 1 ml, between 5 µl to 30 µl, between 10 µl and 1 ml, between 1 µl and 500 µl, between 10 µl and 500 µl, between 10 µl and 250 µl, between 10 µl and 200 µl, between 10 µl and 100 µl or between 10 µl and 50 µl, or about 10 µl.

In another aspect, provided herein is a method for producing a reaction product using a microfluidic device, wherein the method comprises:
 a) introducing a first fluid into a first fluidic channel of the microfluidic device through an inlet port;
 b) introducing a second fluid into the first fluidic channel of the microfluidic device, in illustrative embodiments through a second inlet port; and
 c) producing the reaction product by mixing the first fluid and the second fluid in a reaction well of the microfluidic device that is fluidly connected to the first fluidic channel.

In illustrative embodiments of this method, the microfluidic device is a microfluidic device assembly comprising two or more fluidic devices, and the first fluid and second fluid are introduced in all the microfluidic devices of the device assembly and/or in illustrative embodiments the reaction product forms by mixing the first fluid and the second fluid in the reaction well of each microfluidic device of the device assembly. In illustrative embodiments, the above method aspect is performed using any fluidic device or fluidic device assembly herein, unless incompatible therewith, as non-limiting examples any of the fluidic devices or fluidic device assemblies provided herein in this Exemplary Embodiments section, for example a fluidic device assembly comprising two or more fluidic devices fluidly connected in parallel, or in illustrative embodiments, fluidly connected in series. The reaction product in some embodiments is a protein precipitant. The reaction product in illustrative embodiments comprises microparticles or is microparticles, In another aspect, provided herein is a method for producing a reaction product using any fluidic device assembly herein, unless incompatible therewith, as non-limiting examples any of the fluidic device assemblies provided herein in this Exemplary Embodiments section, for example a fluidic device assembly comprising a series of fluidic devices, wherein the method comprises:
 a) introducing a first fluid into the first fluidic channel of the first fluidic device in the series through the first port channel port;
 b) introducing a second fluid into the first fluidic channel of the first fluidic device in the series through the second port channel port; and
 c) producing the reaction product by mixing the first fluid and the second fluid in the reaction well of each fluidic device in the series.

In some embodiments of the aspect provided immediately above, or any method for making a reaction product provided herein, unless incompatible therewith or already stated, the reaction product is continuously harvested from the fluidic device. In illustrative embodiments of such methods, the method further comprises monitoring consistency of the reaction product over time by measuring the width of a fluid stream of the reaction product and the width of a fluid stream of a reference fluid. In subembodiments, of any such embodiments wherein the reaction product is continuously harvested, at least 1 L, 2 L, or 5 L of particles (e.g. microparticles and nanoparticles), or between 1 L and 10 L, 1 L and 5 L, 1 L and 2 L, or 2 L and 5 L of particles are harvested from the fluidic device and/or between 1 L and 10 L, 1 L and 5 L, 1 L and 2 L, or 2 L and 5 L of combined first, second, and optionally third, fourth etc. fluid are fed into the fluidic device. Further scale-up is provided herein by performing such method using multiple (e.g. 2, 3, 4, 5, 10, 15, 20, etc.) fluidic device assemblies, for example fluidic device assemblies comprising a series of fluidic devices, where the fluidic device assemblies in illustrative embodiments, are linked in parallel.

Such methods in illustrative embodiments can be used to produce different size particles in a controlled manner, by setting certain parameters such as, for example, a first flow rate of a stream of the first fluid as it introduced into the fluidic device, a second flow rate of a stream of the second fluid as it introduced into the fluidic device, a ratio of the first flow rate to the second flow rate, a combined flow rate of the combined first and second streams, overall dimensions of the fluidic device used to perform the method, wherein larger size parts of the fluidic device provide larger particles than smaller size parts, a width of the fluidic constriction channel of the fluid device used to perform the method, or combinations thereof.

In another aspect, provided herein is a method for producing a reaction product using any fluidic device assembly herein, unless incompatible therewith, as non-limiting examples any of the fluidic device assemblies provided herein in this Exemplary Embodiments section, comprising:
 a. filling the fluidic device by introducing a first fluid through the first port into the fluidic device;
 b. trapping the first fluid in the reaction well and the fluidic constriction channel connected therewith by applying negative pressure at the first port to remove some of the first fluid from the fluidic device; and,
 c. introducing a second fluid into the reaction well through the first port to mix with and replace the first fluid, wherein mixing of the first fluid and the second fluid produces a reaction product.

In some embodiments of the aspect provided immediately above, or any method for making a reaction product provided herein, unless incompatible therewith or already stated, the first fluid is essentially removed from the first fluid transport channel, the overflow channel, and the second fluid transport channel before introducing the second fluid into the reaction well.

In some embodiments of any method for making a reaction product provided herein, unless incompatible therewith or already stated, the input of the first fluid and the second fluid creates a laminar flow of the first fluid and the second fluid, and the method further comprises transforming the laminar flow of the first fluid and the second fluid into an unstable flow, but typically not a turbulent flow.

In some embodiments of any method for making a reaction product provided herein, unless incompatible therewith or already stated, the first fluid comprises a protein, wherein the second fluid is a protein precipitant, and wherein the reaction product comprises a protein precipitate comprising the protein.

In illustrative embodiments, a method or process that includes the steps illustrated in FIG. 2 is provided herein, typically using a fluidic device provided herein. In such a method, briefly, a first fluid (e.g., an organic solvent solution comprising a lipid for lipid-based nanoparticles or a polymer solution for polymer-based nanoparticles; indicated as a solid fill within the fluidic device) is introduced into the fluidic device, followed by removal of excess first fluid by applying negative pressure at a port such that it is withdrawn from the device, for example through the first port 1, but remains in the reaction well 2 and, typically, the fluidic constriction channel 4. In the next step of this process, a second fluid (e.g., as described herein for the production of nanoparticles) is introduced into the fluidic device and mixed with the first fluid to produce nanoparticles.

In some embodiments of any method for making a reaction product provided herein, unless incompatible therewith or already stated, the first fluid comprises an organic solvent solution comprising dissolved lipids, or a polymer solution comprising at least one polymer dissolved in a solvent and the second fluid comprises water or an aqueous buffer where the first fluid is an organic solvent solution comprising dissolved lipids, or a water-soluble synthetic polymer solution where the first fluid comprises at least one polymer dissolved in a solvent, and wherein the reaction product is a solution or suspension of particles. In some subembodiments of such embodiments (or in embodiments of any aspect herein), the device is a microfluidic device and the solution or suspension of particles is a solution or suspension of nanoparticles. In some embodiments, the particles are comprised of a metal. Such metal can include, but is not limited to, silver, gold and copper. In illustrative embodiments the particles are metallic nanoparticles.

In any of the aspects or embodiments provided herein wherein the first fluid comprises an organic solvent solution comprising dissolved lipids, the dissolved lipids can comprise at least one lipid selected from the group consisting of dipalmitoylphosphatidylcholine (DPPC); cholesterol; 1,2-Dilauroyl-sn-glycero-3-phosphocholine (DLPC); 1,2-Dimyristoyl-sn-glycero-3-phosphocholine (DMPC); 1,2-Distearoyl-sn-glycero-3-phosphocholine (DSPC); 1,2-Dioleoyl-sn-glycero-3-phosphocholine (DOPC); 1,2-Dimyristoyl-sn-glycero-3-phosphoethanolamine (DMPE); 1,2-Dipalmitoyl-sn-glycero-3-phosphoethanolamine (DPPE); 1,2-Dioleoyl-sn-glycero-3-phosphoethanolamine (DOPE); 1,2-Dimyristoyl-sn-glycero-3-phosphate, sodium salt (DMPA); 1,2-Dipalmitoyl-sn-glycero-3-phosphate, sodium salt (DPPA); 1,2-dioleoyl-sn-glycero-3-phosphate, sodium salt (DOPA); 1,2-Dimyristoyl-sn-glycero-3-phosphoglycerol, sodium salt (DMPG); 1,2-Dipalmitoyl-sn-glycero-3-phosphoglycerol, sodium salt (DPPG); 1,2-dimyristoyl-sn-glycero-3-phospho-L-serine, sodium salt; 1,2-Dipalmitoyl-sn-glycero-3-phosphoserine, sodium salt (DPPS); 1,2-dioleoyl-sn-glycero-3-phospho-L-serine (DOPS), sodium salt; 1,2-Dioleoyl-sn-glycero-3-phosphoethanolamine (DOPE)-Glutaryl, sodium salt; tetramyristoyl cardiolipin sodium salt; 1,2-Distearoyl-sn-glycero-3-phosphoethanolamine (DSPE)-mPEG-2000, sodium salt; 1,2-Distearoyl-sn-glycero-3-phosphoethanolamine (DSPE)-mPEG-5000, sodium salt; and 1,2-Distearoyl-sn-glycero-3-phosphoethanolamine (DSPE)-Maleimide PEG-2000, sodium salt, and a mixture thereof.

In embodiments of any of the aspects or embodiments provided herein wherein the first fluid comprises an organic solvent solution comprising dissolved lipids, the dissolved lipids comprise at least two different types of lipids, optionally selected from the group consisting of DPPC, cholesterol and DOTAP. In any of the aspects or embodiments provided herein wherein the first fluid comprises an organic solvent solution comprising dissolved lipids, the organic solvent is selected from the group consisting of ethanol, methanol and chloroform, ethyl acetate, isopropanol, and hexane. In any of the aspects or embodiments provided herein wherein the first fluid comprises an organic solvent solution comprising dissolved lipids, the dissolved lipids comprise DPPC, cholesterol and DOTAP, and the organic solvent solution comprises ethanol. In any of the aspects or embodiments provided herein wherein the first fluid comprises an organic solvent solution comprising dissolved lipids, the aqueous buffer is a physiological buffer, optionally phosphate-buffered saline.

In embodiments of any of the aspects or embodiments provided herein wherein the first fluid comprises a polymer solution comprising at least one polymer dissolved in a solvent, the polymer is selected from the group consisting of polylactic acid (PLA), poly-1-lysine (PLL), polyglutamic acid (PGluA), polyglycolic acid (PGA), polyethylene glycol (PEG), polycaprolactone (PCL), polyaspartate (PAA), poly (d,l-lactide-co-glycolic) acid (PLGA), cyclodextrins (CD), and N-(2-hydroxypropyl)-methacrylamide copolymer (HPMA), a natural polymer, chitosan, heparin, albumin, dextran, gelatin, alginate, collagen, and a mixture thereof. In certain subembodiments of such embodiments, the solvent is selected from the group consisting of dichloromethane and ethyl acetate, benzyl alcohol, cyclohexane, acetonitrile, and acetone. In certain subembodiments of such embodiments and subembodiments, the water-soluble synthetic polymer solution comprises poly(vinyl alcohol) or didecyldimethylammonium bromide; and the aqueous solution is optionally water or phosphate-buffered saline.

In embodiments of any fluidic device aspect or fluidic device assembly aspect herein, or method for producing or making nanoparticles, the reaction well or one or more reaction wells, can comprise nanoparticles, optionally wherein said nanoparticles are lipid-based nanoparticles or polymeric nanoparticles. In some such embodiments, a) the lipid-based nanoparticles comprise at least one lipid selected from the group consisting of dipalmitoylphosphatidylcholine (DPPC); cholesterol; 1,2-Dilauroyl-sn-glycero-3-phosphocholine (DLPC); 1,2-Dimyristoyl-sn-glycero-3-phosphocholine (DMPC); 1,2-Distearoyl-sn-glycero-3-phosphocholine (DSPC); 1,2-Dioleoyl-sn-glycero-3-phosphocholine (DOPC); 1,2-Dimyristoyl-sn-glycero-3-phosphoethanolamine (DMPE); 1,2-Dipalmitoyl-sn-glycero-3-phosphoethanolamine (DPPE); 1,2-Dioleoyl-sn-glycero-3-phosphoethanolamine (DOPE); 1,2-Dimyristoyl-sn-glycero-3-phosphate, sodium salt (DMPA); 1,2-Dipalmitoyl-sn-glycero-3-phosphate, sodium salt (DPPA); 1,2-dioleoyl-sn-glycero-3-phosphate, sodium salt (DOPA); 1,2-Dimyristoyl-sn-glycero-3-phosphoglycerol, sodium salt (DMPG); 1,2-Dipalmitoyl-sn-glycero-3-phosphoglycerol, sodium salt (DPPG); 1,2-dimyristoyl-sn-glycero-3-phospho-L-serine, sodium salt; 1,2-Dipalmitoyl-sn-glycero-3-phosphoserine, sodium salt (DPPS); 1,2-dioleoyl-sn-glycero-3-phospho-L-serine (DOPS), sodium salt; 1,2-Dioleoyl-sn-glycero-3-phosphoethanolamine (DOPE)-Glutaryl, sodium salt; tetramyristoyl cardiolipin sodium salt; 1,2-Distearoyl-sn-glycero-3-phosphoethanolamine (DSPE)-mPEG-2000, sodium salt; 1,2-Distearoyl-sn-glycero-3-phosphoethanolamine (DSPE)-mPEG-5000, sodium salt; and 1,2-Distearoyl-sn-glycero-3-phosphoethanolamine (DSPE)-Maleimide PEG-2000, sodium salt, and a mixture thereof; or b) the polymeric nanoparticles comprise at least one polymer selected from the group consisting of polylactic acid (PLA), poly-1-lysine (PLL), polyglutamic acid (PGluA), polyglycolic acid (PGA), polyethylene glycol (PEG), polycaprolactone (PCL), polyaspartate (PAA), poly(d,l-lactide-co-glycolic) acid (PLGA), cyclodextrins (CD), and N-(2-hydroxypropyl)-methacrylamide copolymer (HPMA), a natural polymer, chitosan, heparin, albumin, dextran, gelatin, alginate, collagen, and a mixture thereof.

Furthermore, in some subembodiments of such embodiments, the solvent is selected from the group consisting of dichloromethane and ethyl acetate, benzyl alcohol, cyclohexane, acetonitrile, and acetone and/or the water-soluble synthetic polymer solution comprises poly(vinyl alcohol) or didecyldimethylammonium bromide; and the aqueous solution is optionally water or phosphate-buffered saline.

In further subembodiments of such embodiments, the aqueous solution or water-soluble synthetic polymer solution comprises a nucleic acid molecule, detection agent, or a therapeutic agent that is enveloped within the nanoparticle upon mixture of the water-soluble synthetic polymer and the polymer solution. In further subembodiments of such embodiments, the aqueous buffer or water soluble polymer solution, respectively, is introduced into the fluidic device at a flow rate of from one to 30 ml/minute, optionally from five to 20 ml/minute or 10 to 20 ml/minute. Furthermore, in certain illustrative embodiments the fluidic constriction channel of the fluidic device(s) has a width or diameter of less than 400 um and the flow rate is greater than 5 ml/minute.

In embodiments of any fluidic device aspect or fluidic device assembly aspect herein, or method for producing or making nanoparticles using the same, the nanoparticles have a diameter of between 5 nm and 500 nm. Furthermore, such methods can further include characterizing the properties of the nanoparticles, optionally wherein said properties comprise size, polydispersity index (PDI), or zeta potential, optionally as measured using dynamic light scattering (DLS) or transmission electron microscopy (TEM).

In another aspect, provided herein are particles (e.g. microparticles or nanoparticles) produced by any method for producing particles provided herein. The nanoparticles, including nanoparticles in a microfluidic device herein can have a diameter of less than 600 nm, for example between 5 nm and 500 nm. The nanoparticles can comprise at least one detection agent and/or at least one therapeutic agent.

In some embodiments of any of the methods herein for making or producing a reaction product, wherein the fluidic device comprises a first input port, between 100 to 1000 µl, optionally 100 to 200 µl, of the first fluid is introduced through the first port; or wherein multiple fluidic devices are fluidly connected to one another in series or parallel, greater 1000 µl aqueous buffer or water, or between 400 µl and 5 ml of aqueous buffer or water is introduced through the first port.

In some embodiments of any of the fluidic device or fluidic device assembly herein operable to produce, and effective for producing a reaction product, unless already stated therein or incompatible therewith:
 a) the first fluid transport channel comprises a diameter distal to the first port of about four times its diameter proximal to the first port;
 b) the diameter of the reaction well is approximately twice the diameter of the fluid transport channel proximal to the first port;
 c) the length of the reaction well is approximately one third the length of the first fluid transport channel;
 d) the diameter of the overflow channel is approximately 0.4 to 0.75 times the diameter of the first fluid transport channel distal to the first port;
 e) the length of the overflow channel is at least about 0.9 times the length of the first fluid transport channel;
 f) the second fluid transport channel comprises a diameter distal to the first port of about two times its diameter proximal to the second port; and/or
 g) the length of the second fluid transport channel is approximately equivalent to approximately 1.25 times the length of the first fluid transport channel.

In some embodiments of any of the fluidic device or fluidic device assembly herein operable to produce, and effective for producing a reaction product, unless already stated therein or incompatible therewith, the fluidic device is comprised of PDMS wherein the diameter of the overflow channel is approximately 0.6 times the diameter of the first fluid transport channel distal to the first port; or the fluidic device is comprised of PDMS wherein the diameter of the overflow channel is approximately 0.6 times the diameter of the first fluid transport channel distal to the first port; or the fluidic device is comprised of COC wherein the diameter of the overflow channel is approximately 0.5 times the diameter of the first fluid transport channel distal to the first port.

In some embodiments of any of the fluidic device or fluidic device assembly herein operable to produce, and effective for producing a reaction product, unless already stated therein or incompatible therewith:
 the diameter of the fluidic constriction channel is approximately 0.15 to approximately 0.30 times the diameter of the reaction well;
 the diameter of the fluidic constriction channel is approximately 150-225 µm, optionally wherein the fluidic constriction channel is comprised of PDMS;
 the diameter of the fluidic constriction channel is approximately 175-200 mu;
 the diameter of the fluidic constriction channel is approximately 160-215 µm, optionally wherein the fluidic constriction channel is comprised of COC;
 the diameter of the fluidic constriction channel is approximately 0.2-0.25 times the diameter of the reaction well;
 the diameter of the fluidic constriction channel is approximately 0.1-0.2 times the diameter of the second fluid transport channel at the point at which the fluidic constriction channel and the second fluid transport channel contact one another;
 the length of the fluidic constriction channel is approximately 0.1-0.25 times the length of the reaction well;
 the length of the fluidic constriction channel is approximately 0.1-0.175 times the length of the reaction well; and/or,
 the length of the fluidic constriction channel is approximately 0.125-0.150 times the length of the reaction well.

In some embodiments of any of the fluidic device or fluidic device assembly herein operable to produce, and effective for producing a reaction product, unless already stated therein or incompatible therewith: the fluidic constriction channel is comprised of PDMS and has a length of approximately 0.1-0.175 times, optionally 0.125-0.150 times, the length of the reaction well; or the fluidic constriction channel is comprised of COC and has a length of approximately 0.11-0.13 times the length of the reaction well.

In some embodiments of any of the fluidic device or fluidic device assembly herein operable to produce, and effective for producing a reaction product, unless already stated therein or incompatible therewith:
 the fluidic device has a height of about 300 µm to about 500 µm, optionally about 500 µm;
 the first fluid transport channel has a length of from about 2000 um to about 10,000 um, optionally about 5900

μm, and/or a width or diameter of about 1000 um to about 2000 um, optionally about 1200 um;

the overflow channel has a length of from about 8000 um to about 15,000 um, optionally about 10,900 um, and/or a width or diameter of about 1200 um to about 2000 um, optionally about 1200 um;

the second fluid transport channel has a length of from about 2000 um to about 10,000 um, optionally about 1500 um, and/or a width or diameter of about 1000 um to about 2000 um, optionally about 1500 um;

the reaction well has a length of from about 5000 um to about 12,000 um, optionally about 7460 um, and/or a width or diameter of about 3000 um to about 6000 um, optionally about 4000 um, and/or optionally comprises an oval shape;

the fluidic constriction channel has a length of from about 200 um to about 1,000 um, optionally about 500 μm, and/or a width or diameter of about 50 um to about 500 um, optionally about 50 um to about 200 um, or about 100 um;

the width or diameter of the overflow channel and/or the second fluid transport channel is about 10 to about 40 times greater than the diameter of the fluidic constriction channel;

the diameter of the reaction well is approximately 40 to approximately 120 to times the diameter of the fluidic constriction channel;

the ratio of capillary pressures within the fluidic constriction channel and the overflow channel is at least 1.5:1, between 10:1 and 1.5:1, or optionally about four to one;

the fluidic constriction channel and/or and the reaction well are completely filled with fluid;

the fluidic constriction channel does not comprise air;

a fluid air interface is present at an end of the fluidic constriction channel distal to the reaction well; and/or, the fluidic constriction channel is comprised of a hydrophobic material.

In another aspect, provided herein is a fluidic device comprising:

a first fluid transport channel comprising a straight segment, said first fluid transport channel in fluid connection with a first port and optionally comprising a section having a rounded orientation;

a second fluid transport channel;

a fluidic constriction channel;

a reaction well;

a passive pressure sensing channel in fluid connection with a second port;

a third fluid transport channel in fluid connection with a third port; and an interface channel segment;

wherein:

the second fluid transport channel is in direct fluidic communication with the first fluid transport channel;

the fluidic constriction channel is in direct fluidic communication with the reaction well and the interface channel segment connecting the second fluid transport channel and the third fluid transport channel; and the reaction well is in direct fluidic connection with the passive pressure sensing channel.

In illustrative embodiments, such fluidic device is effective for determining and/or detecting and operable to determine and/or detect a reaction product or whether a first fluid and a second fluid react by forming a reaction product. In some embodiments of the immediately above aspect, or any fluidic device herein that is effective for detecting, and operable to detect whether a first fluid and a second fluid react by forming a reaction product, the width of the second and third fluid transport channels are the same or different and between 3/200 and the same width of the first fluid transport channel, optionally wherein the width of the second and third fluid transport channels are the same. In some embodiments of the immediately above aspect, or any fluidic device herein that is effective for detecting, and operable to detect whether a first fluid and a second fluid react by forming a reaction product, the fluidic device of any one of claim 31 or 32, wherein the depth of the second and third fluid transport channel are the same or different and between 3/70 and the same depth of the first fluid transport channel. In some embodiments of the immediately above aspect, or any fluidic device herein that is effective for detecting, and operable to detect whether a first fluid and a second fluid react by forming a reaction product, the depth of the second and third fluid transport channels are the same. In some embodiments of the immediately above aspect, or any fluidic device herein that is effective for detecting, and operable to detect whether a first fluid and a second fluid react by forming a reaction product, the width and depth of an end of the interface channel segment directly connected to the second fluid transport channel is the same as the width and depth of the second fluid transport channel and the width and depth of an opposite end of the interface channel segment directly connected to the third fluid transport channel is identical to the width and depth of the third fluid transport channel, optionally wherein the width and depth of the interface channel segment, the second fluid transport channel, and the third fluid transport channel are the same.

In some embodiments of the immediately above aspect and embodiments, or any fluidic device herein that is effective for detecting, and operable to detect whether a first fluid and a second fluid react by forming a reaction product, the length of the interface channel segment is equal to the width of the fluidic constriction channel. In some embodiments of the immediately above aspect, the hydraulic diameter of the second and third fluid transport channels are the same or different and between 3/105 to 1/1 the hydraulic diameter of the first fluid transport channel, optionally wherein the hydraulic diameter of the second and third fluid transport channels are the same. In some embodiments of the immediately above aspect, the hydraulic diameter of the second fluid transport channel is between 1/6 and 1/1 the hydraulic diameter of the third fluid transport channel, optionally wherein the hydraulic diameter of the second and third fluid transport channels are the same. In some embodiments of the immediately above aspect, or any fluidic device herein that is effective for detecting, and operable to detect whether a first fluid and a second fluid react by forming a reaction product, the length, width and depth of the fluidic constriction channel is between 10-500 um, 15-500 um, and 15-300 um, the length, width and depth of the interface channel segment is between 15-500 um, 15-100 um, and 15-100 um, respectively, the length of the fluidic constriction channel is between 0.0025 to 1.25 times the length of the second and/or third fluid transport channels, the width of the fluidic constriction channel is between 0.1 to 33 times the width of the second and/or third fluid transport channels, the width and/or depth of the fluidic constriction channel are the same or different from those of the second and/or third fluid transport channels, the passive pressure sensing channel extends from the reaction well opposite the fluidic constriction channel and terminates at a passive pressure sensing channel port; and the volume of the reaction well has a volume of between 1 nl and 450 nl, optionally wherein the reaction well has a volume of between 15 and 35 nl.

In some embodiments of the immediately above aspect and embodiments, or any fluidic device herein that is effective for detecting, and operable to detect whether a first fluid and a second fluid react by forming a reaction product, the passive pressure sensing channel has a smaller width and/or depth compared to the interface channel segment, the second fluid transport channel and the third fluid transport channel, such that the hydrodynamic resistance of the passive pressure sensing channel is at least 1.01 times the hydrodynamic resistance of each of the interface channel segment, the second fluid transport channel and the third fluid transport channel, and optionally the hydrodynamic resistance of the passive pressure sensing channel is between 1.01 and $5 \times 10^7$ times the hydrodynamic resistance of each of the interface channel segment, the second fluid transport channel and the third fluid transport channel.

In some embodiments of the immediately above aspect and embodiments, or any fluidic device herein that is effective for detecting, and operable to detect whether a first fluid and a second fluid react by forming a reaction product, the passive pressure sensing channel terminates at the second port and:
a) is a straight channel;
b) comprises at least one bend, rounded orientation, and/or curve;
c) comprises at least two pressure sensing channel segments, wherein at least a first pressure sensing channel segment extends horizontally or at an angle from the reaction well, and at least one second pressure sensing channel segment extends from the first segment at other than a straight line, optionally at an angle of between 1 and 180 degrees or 40 to 120 degrees with respect to the first pressure sensing channel segment; or
d) comprises at least three pressure sensing channel segments, wherein at least a first pressure sensing channel segment extends horizontally or at an angle from the reaction well, at least one second pressure sensing channel segment extends from the first pressure sensing channel segment at other than a straight line and optionally at an angle of between 1 and 180 degrees with respect to the first segment, and at least one third pressure sensing channel segment extends from the second segment at other than a straight line and optionally at an angle of between 1 and 180 or 40 to 120 degrees with respect to the second pressure sensing channel segment.

In some embodiments of the immediately above aspect and embodiments, or any fluidic device herein that is effective for detecting, and operable to detect whether a first fluid and a second fluid react by forming a reaction product:
a) the second fluid transport channel is in direct fluidic communication with the first fluid transport channel at an end of the first fluid transport channel opposite the first port;
b) the fluidic constriction channel is in direct fluidic communication with the reaction well and an interface channel segment 5C directly connecting the second fluid transport channel and the third fluid transport channel, wherein the width of the interface channel segment is identical to the width of the fluid transport channel to which it is directly connected;
c) the reaction well is in direct fluidic connection with the passive pressure sensing channel at an end of the passive pressure sensing channel opposite the second port;
d) the passive pressure sensing channel extends from the reaction well opposite the fluidic constriction channel and terminates at the passive pressure sensing channel port; and
e) the first fluid transport channel is not in direct fluidic communication with the reaction well.

In some embodiments of the immediately above aspect, or any fluidic device herein that is effective for detecting, and operable to detect whether a first fluid and a second fluid react by forming a reaction product, the second fluid transport channel comprises a precipitate therein. In some embodiments of the immediately above aspect, or any fluidic device herein that is effective for detecting, and operable to detect whether a first fluid and a second fluid react by forming a reaction product, the reaction well and optionally the fluidic constriction channel are filled with fluid, but the rest of the device is empty.

In another aspect, provided herein is microfluidic assembly comprising at least two of the fluidic devices of the immediately above aspect or embodiments, or at least two of any fluidic devices herein that each are effective for detecting, and operable to detect whether a first fluid and a second fluid react by forming a reaction product.

In another aspect, provided herein is a method for detecting a reaction produced formed by a reaction of a first fluid and a second fluid using a microfluidic device comprising a passive pressure sensing channel. Such method can include the following steps: a. optionally introducing the first fluid into the device typically through a first port; b. trapping a volume of the first fluid in a reaction well, in illustrative embodiments by capturing a droplet of a volume, optionally a pre-defined volume, of the first fluid in the reaction well; c. introducing the second fluid (i.e. a second solution or a second liquid) into the device so that it can interact with the trapped volume of the first fluid, such that the first and second fluids mix in at least part of ab interface channel segment and/or a fluidic constriction channel to form a reaction product of one or more components of the first fluid and one or more components of the second fluid; and optionally, but typically, d. detecting the reaction product, wherein in illustrative embodiments, the reaction product is a precipitate. The reaction product can be detected for example, in a second fluid transport channel.

In some embodiments of the above method, the microfluidic device is any of the above fluidic devices comprising a passive pressure sensing channel, or any fluidic device herein that is effective for such method and/or comprises a passive pressure sensing channel.

In another aspect, provided herein is a method for determining (or detecting) whether a first fluid and a second fluid react by forming a reaction product using a fluidic device of any of the above fluidic devices comprising a passive pressure sensing channel, or any fluidic device herein that is effective for such method and/or comprises a passive pressure sensing channel. Such method can include the following steps, with reference to a non-limiting example provided in FIG. 18: a. optionally introducing a first fluid into the device typically through a first port; b. trapping a volume of the first fluid in a reaction well 2, in illustrative embodiments by capturing a droplet of a volume, optionally a pre-defined volume, of the first fluid in the reaction well 2; c. introducing a second fluid (i.e. a second solution or a second liquid) into the device so that it can interact with the trapped volume of the first fluid. Next, the second fluid is introduced into the device typically into a third fluid transport channel 5B and an interface channel segment 5C, typically thru a third port 6 such that the first and second fluids mix in at least part of the interface channel segment 5C and/or a fluidic constriction channel 4 to form a reaction product of one or more components of the first fluid and one or more components of the second fluid; and optionally, but typically, d. detecting the reaction product, wherein in illustrative embodiments, the reaction product is a precipitate. The reaction product can be detected for example, in the second fluid transport channel 5A.

In another aspect, provided herein is a method for determining (or detecting) whether a first fluid and a second fluid react by forming a reaction product using a fluidic device of the above fluidic device comprising a passive pressure sensing channel, or any fluidic device herein that is effective for such method and/or comprises a passive pressure sensing channel, said method comprising:
  a. filling the fluidic device with the first fluid through the first port by positive pressure;
  b. trapping a volume of the first fluid in the reaction well and the fluidic constriction channel by applying negative pressure at the first port or by applying positive pressure at the third port, to remove some of the first fluid from the fluidic device;
  c. introducing the second fluid into the second and third fluid transport channels through the third port by positive pressure such that the first and second fluids mix in at least part of the interface channel segment, the fluidic constriction channel, and/or an opening of the reaction well;
  wherein,
  prior to introducing the second fluid into the third fluid transport channel the passive pressure sensing channel is filled with air and does not comprise fluid such that a fluid-air interface is present at the point at which the reaction well and the passive pressure sensing channel connect;
  if a reaction product forms from the mixing of the first and second fluids, said precipitate will form a precipitate plug within the second fluid transport channel, optionally also in the first fluid transport channel, the fluidic constriction channel, and/or the interface channel segment; and
  continued introduction of the second fluid into the third fluid transport channel will increase the pressure in the reaction well and passive pressure sensing channel such that fluid flows into the passive pressure sensing channel and is detected, thereby determining whether the first fluid and the second fluid react by forming a reaction product.

In another aspect, provided herein is a method for determining (or detecting) whether a first fluid and a second fluid react by forming a reaction product using a fluidic device of the above fluidic device comprising a passive pressure sensing channel, or any fluidic device herein that is effective for such method and/or comprises a passive pressure sensing channel, said method comprising:
  a. trapping a volume of a first fluid in the reaction well; and
  b. introducing a second fluid into the third fluid transport channel and the interface channel segment through the third port such that the first and second fluids mix in at least part of the interface channel segment and/or the fluidic constriction channel and/or the opening of the reaction well and a detectable reaction or reaction product resulting from the reaction of one or more components of the first fluid and one or more components the second fluid is detected and/or formed that increases the pressure of at least one channel within the device, wherein the increased pressure is detected.

In another aspect, provided herein is a method for determining (or detecting) whether a first fluid and a second fluid react by forming a reaction product using a fluidic device of the above fluidic device comprising a passive pressure sensing channel, or any fluidic device herein that is effective for such method and/or comprises a passive pressure sensing channel, said method comprising:
  a. trapping a volume of a first fluid in the reaction well; and
  b. introducing a second fluid into the third fluid transport channel and the interface channel segment thru the third port such that the first and second fluids mix in at least part of the interface channel segment and/or the fluidic constriction channel and/or the opening of the reaction well and detectable reaction or reaction product resulting from the reaction of one or more components of the first fluid and one or more components the second fluid is formed.

In some embodiments of any method herein for detecting a reaction product or determining whether a first fluid and a second fluid react by forming a reaction product, the reaction product formation results in a thickened fluid, a polymer, a gel, a hardened product, an aggregated product, a fluorescent product, a colored product, or a change of color. In some embodiments of any method herein for detecting a reaction product or determining whether a first fluid and a second fluid react by forming a reaction product, the reaction product forms a precipitate.

In some embodiments of any method herein for detecting a reaction product or determining whether a first fluid and a second fluid react by forming a reaction product, prior to the introduction of the second fluid into the third fluid transport channel the passive pressure sensing channel is filled with air and does not comprise fluid, such that a fluid-air interface is present at the point at which the reaction well and the passive pressure sensing channel connect. In some embodiments of any method herein for detecting a reaction product or determining whether a first fluid and a second fluid react by forming a reaction product, before trapping the first fluid, the fluidic device is filled with a first fluid thru the first port by positive pressure.

In some embodiments of any method herein for detecting a reaction product or determining whether a first fluid and a second fluid react by forming a reaction product, fluid flowing into the passive pressure sensing channel is detected by detecting fluid exiting the passive pressure sensing channel, optionally wherein said fluid is detected visually, optionally using a camera. In some embodiments of any method herein for detecting a reaction product or determining whether a first fluid and a second fluid react by forming a reaction product, after the precipitate forms, fluid enters the passive pressure sensing channel, optionally wherein the precipitate is detected by detecting the fluid in the passive pressure sensing channel. In some embodiments of any method herein for detecting a reaction product or determining whether a first fluid and a second fluid react by forming a reaction product, the first fluid or the second fluid, optionally the second fluid, is mammalian sweat, or an artificial sweat fluid. In some embodiments of any method herein for detecting a reaction product or determining whether a first fluid and a second fluid react by forming a reaction product, the second fluid is introduced into the third fluid transport channel at a flow rate of between 0.01 nl/min and 1 ml/min, optionally between 1 nl/min and 25 u/min.

Unless otherwise indicated, the terms and phrases used herein are to be understood as the same would be understood by one of ordinary skill in the art. For instance, terms and phrases used herein can be used consistent with the definition provided by a standard dictionary such as, for example, the Tenth Edition of Merriam Webster's Collegiate Dictionary (1997). The terms "about", "approximately", and the like, when preceding a list of numerical values or range, refer to each individual value in the list or range independently as if each individual value in the list or range was immediately preceded by that term. The values to which the same refer are exactly, close to, or similar thereto (e.g., within about one to about 10 percent of one another). Ranges can be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed. All references cited within this disclosure are hereby incorporated by reference into this application in their entirety. A skilled artisan will appreciate that where the specification provides an approximate value or range, the exact value or range is within the scope of the current specification as well.

Certain embodiments are further disclosed in the following examples. These embodiments are provided as examples only and are not intended to limit the scope of the claims in any way.

EXAMPLES

Example 1

Production of Nanoparticles Using Single Fluidic Devices

Figure 3:
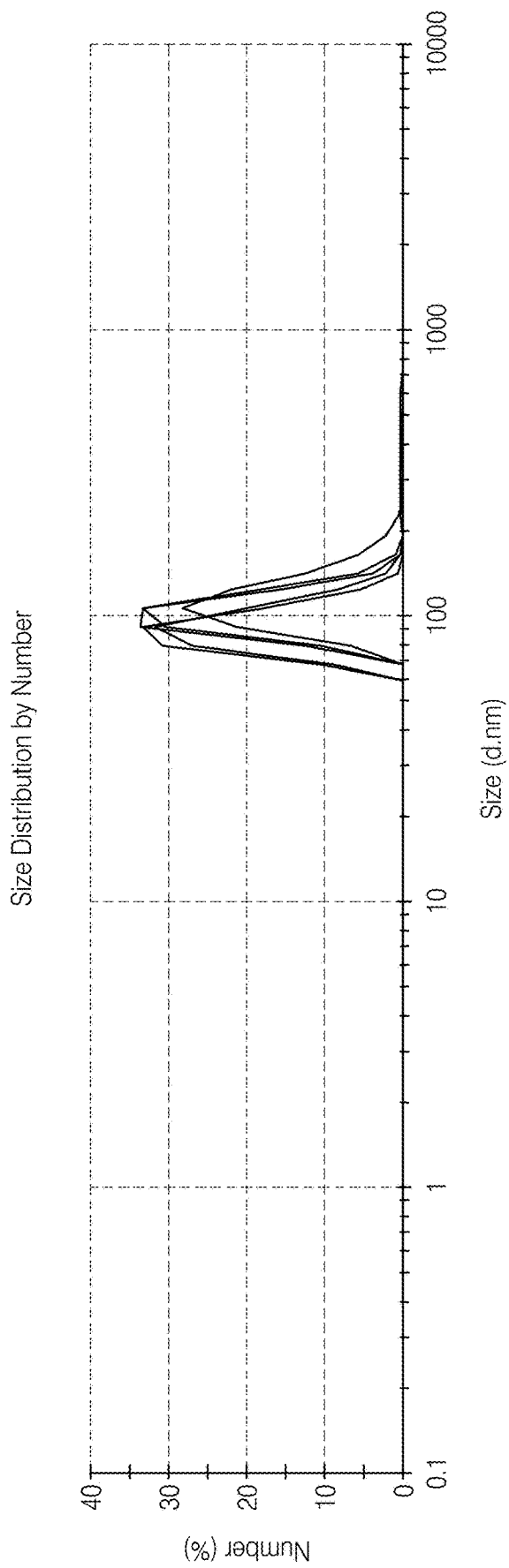
FIG. 3 provides the size distribution plot of five batches of liposomes produced using an exemplary fluidic device.
Figure 4:
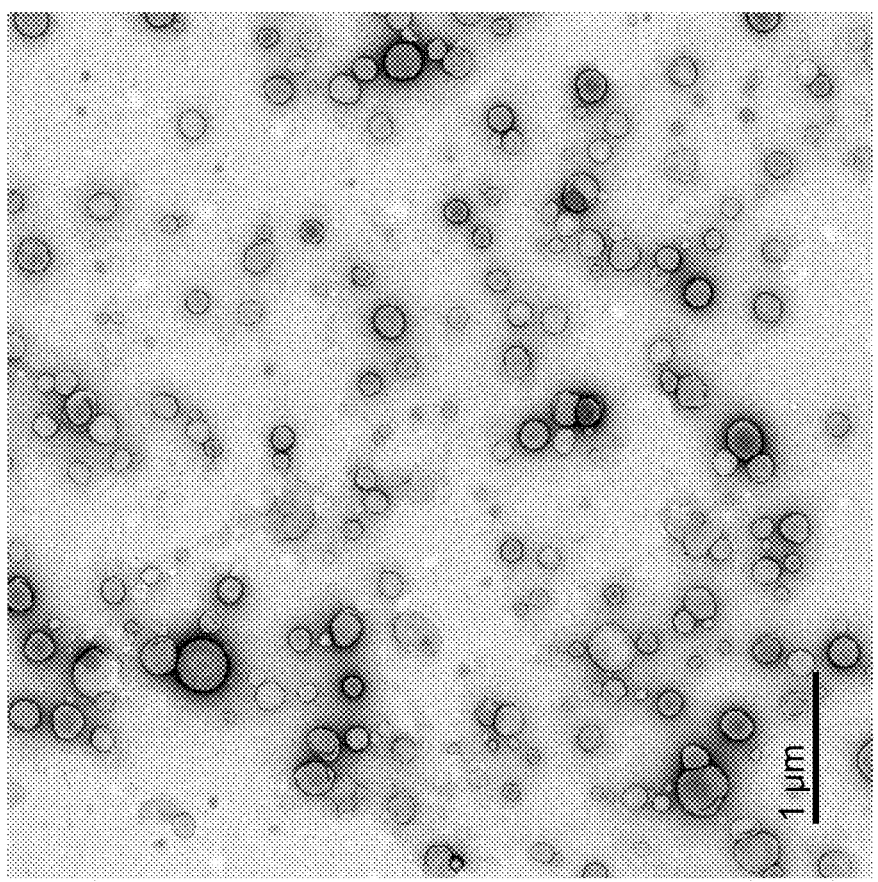
FIG. 4 provides transmission electron microscopy of liposomes produced using an exemplary fluidic device.

This example illustrates the production of nanoparticles using a fluidic device illustrated in FIG. 1, which includes a first port 1, first fluid transport channel 1A, reaction well 2, overflow channel 3, fluidic constriction channel 4, second fluid transport channel 5A, and second port 5. The device used in this example had the approximate dimensions provided for the exemplary device of FIG. 1 in Table 1. The process to make particles illustrated in FIGS. 2A-2C and discussed in detail hereinabove, was used with this device with an exemplary DPPC/Cholesterol/DOTAP lipid formulation to make nanoparticles. A lipid formulation of DPPC/Cholesterol/DOTAP in a ratio of 67:30:3 was dissolved in ethanol at a concentration of 10 mg/mL and used as the first fluid and was loaded into the fluidic device (steps one and two). The second fluid used was phosphate-buffered saline (PBS) and was introduced into the device at a flow rate of 20 ml/minute (step 3). Mixture of the first and second fluids in the fluidic device and following these steps resulted in liposomes being present in the reaction well 2. These liposomes were washed out of the reaction well 2 by inputting excess PBS into the first port 1, and analyzed using dynamic light scattering (DLS) (FIG. 3) and transmission electron microscopy (TEM) (FIG. 4). The number-weighted size distribution of five batches of liposomes formulated in the device and analyzed by DLS is shown in FIG. 3. The DLS plot (FIG. 3) demonstrates that this fluidic device and method reproducibly generated consistent formulations. This was confirmed by TEM, as shown in FIG. 4 (scale bar in FIG. 4=1 micrometer (μm)).

Figure 5:
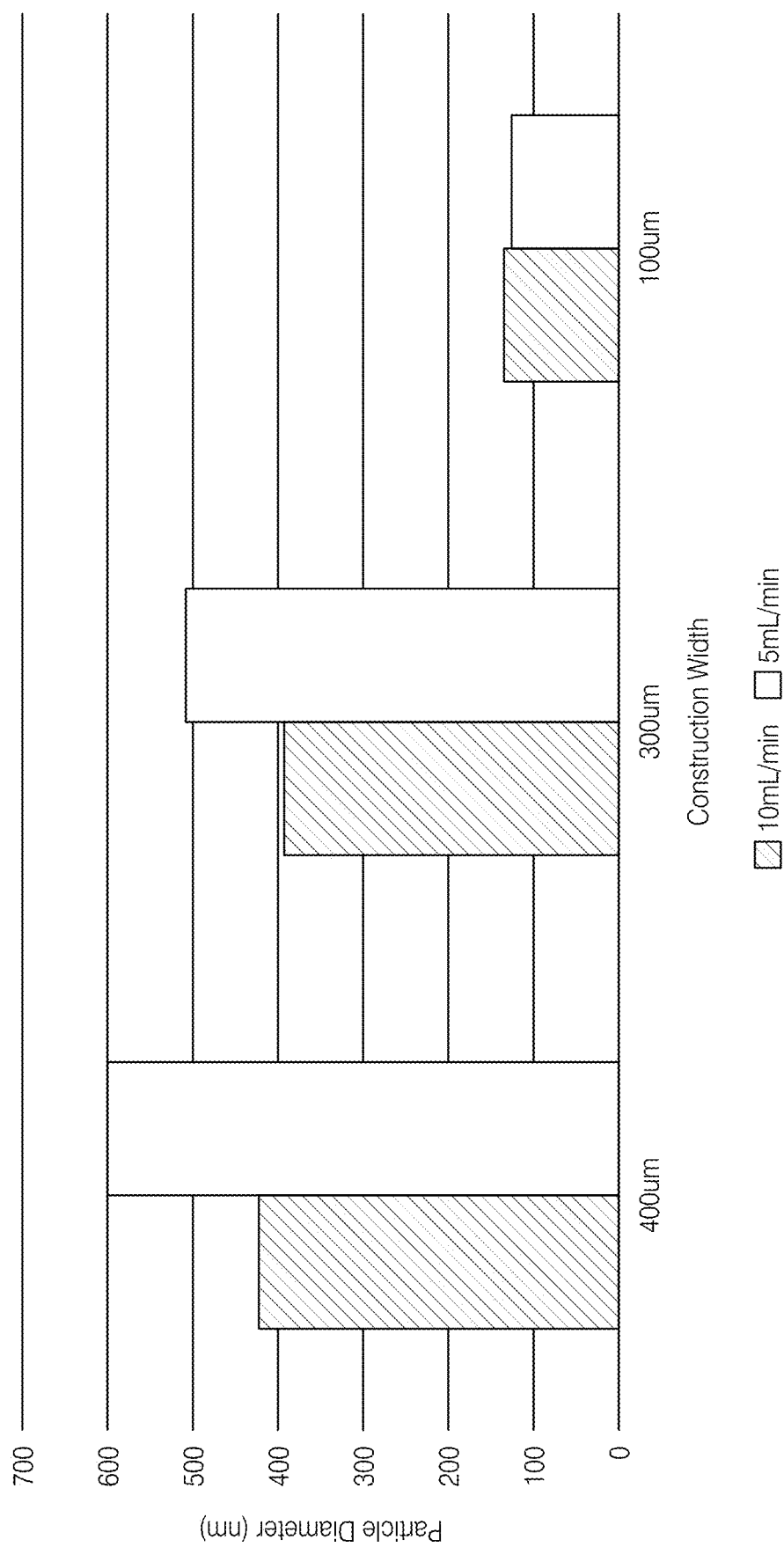
FIG. 5 provides results obtained using fluidic devices having fluidic constriction channels of different widths (relative to each device) and washing rates.

While the data presented in FIGS. 3-4 was generated using a fluidic device having a 100 μm-wide fluidic constriction channel, fluidic devices having wider fluidic constriction channels but otherwise identical to the exemplary device of FIG. 1 with other dimensions for this device as provided in Table 1, were also tested in conjunction with two different washing speeds in the third step (i.e., the flow rate at which the second fluid was introduced into the fluidic device). As shown in FIG. 5 (experiment performed using DPPC/Cholesterol/DOTAP in a ratio of 67:30:3 as described above for the data illustrated in FIGS. 3-4), the 100 μm-wide fluidic constriction channel produced liposomes having particle diameters of about a 100 nm diameter whether the washing speed was 5 or 10 mL/min. Fluidic devices having larger fluidic constriction channels (300 and 400 μm) produced larger liposomes, the size of which depended on the washing speed. At 10 mL/min, the fluidic devices having a 300 or 400 μm fluidic constriction channel produced liposomes having particle diameters of about 400 nm. At 5 mL/min, the fluidic devices having a 300 or 400 μm fluidic constriction channel produced liposomes having diameters of about 500 nm or 600 nm, respectively. In some applications, liposomes having a particle diameter of 600 nm can be too large to be useful (e.g., for clinical use). Accordingly, in some embodiments, wherein the flow rate of the second fluid is greater than 5 ml/minute and liposomes having a particle diameter of less than 600 nm are desired, the fluidic constriction channel of the fluidic device should have a width of less than about 400 μm.

Figure 6:
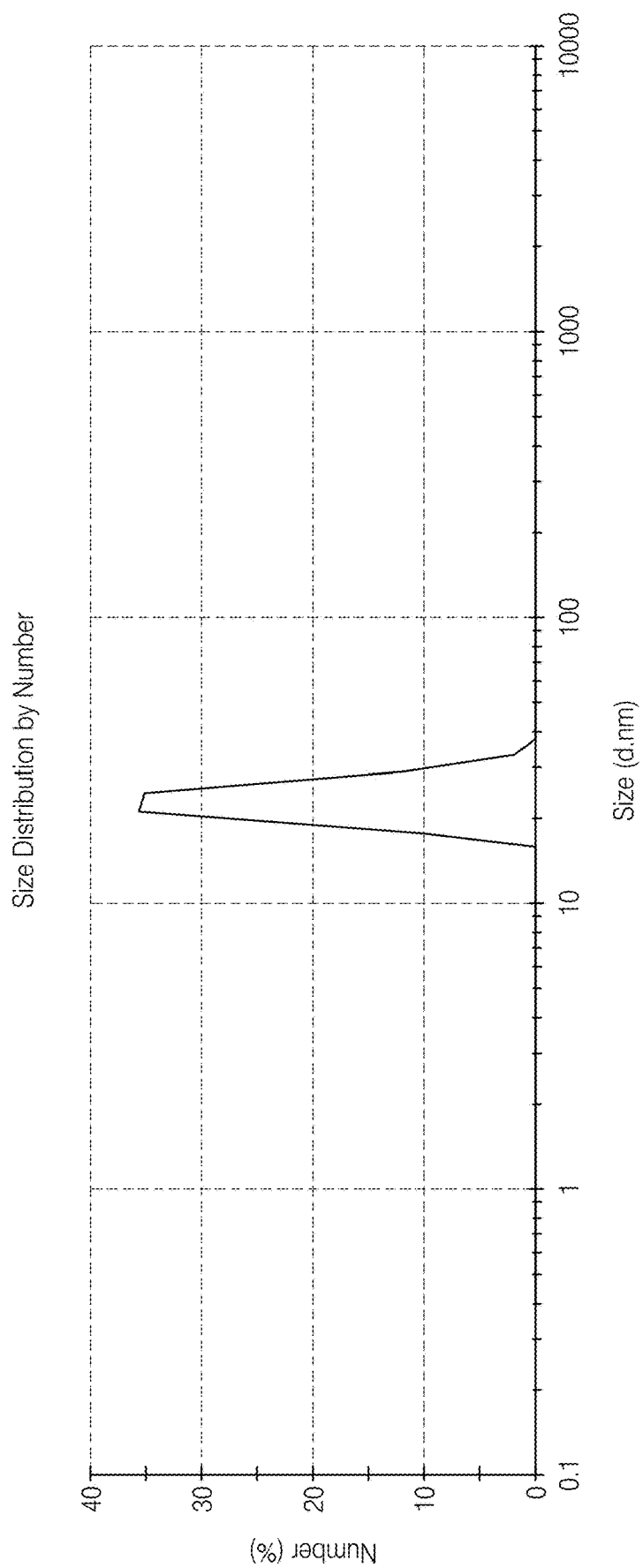
FIG. 6 shows the average number-weighted size of the lipid-based micelles prepared using DSPE-PEG dissolved in ethanol as the first fluid and PBS as the second fluid.

The process described above and illustrated in FIG. 2 was also carried out in the fluidic device illustrated in FIG. 1 with dimensions provided in Table 1 using a second exemplary lipid formulation. A lipid formulation of DSPE-PEG(2000) Maleimide (1,2-distearoyl-sn-glycero-3-phosphoethanolamine-N-[maleimide(polyethylene glycol)-2000] (ammonium salt)) dissolved in ethanol was utilized as the first fluid. Phosphate-buffered saline (PBS) (the second fluid) was then washed through the device, mixing with the first fluid to form lipid micelles. The average number-weighted size of the micelles was determined to be 23.07 nm with a polydispersity index (PDI) of 0.227 (FIG. 6).

Figure 7:
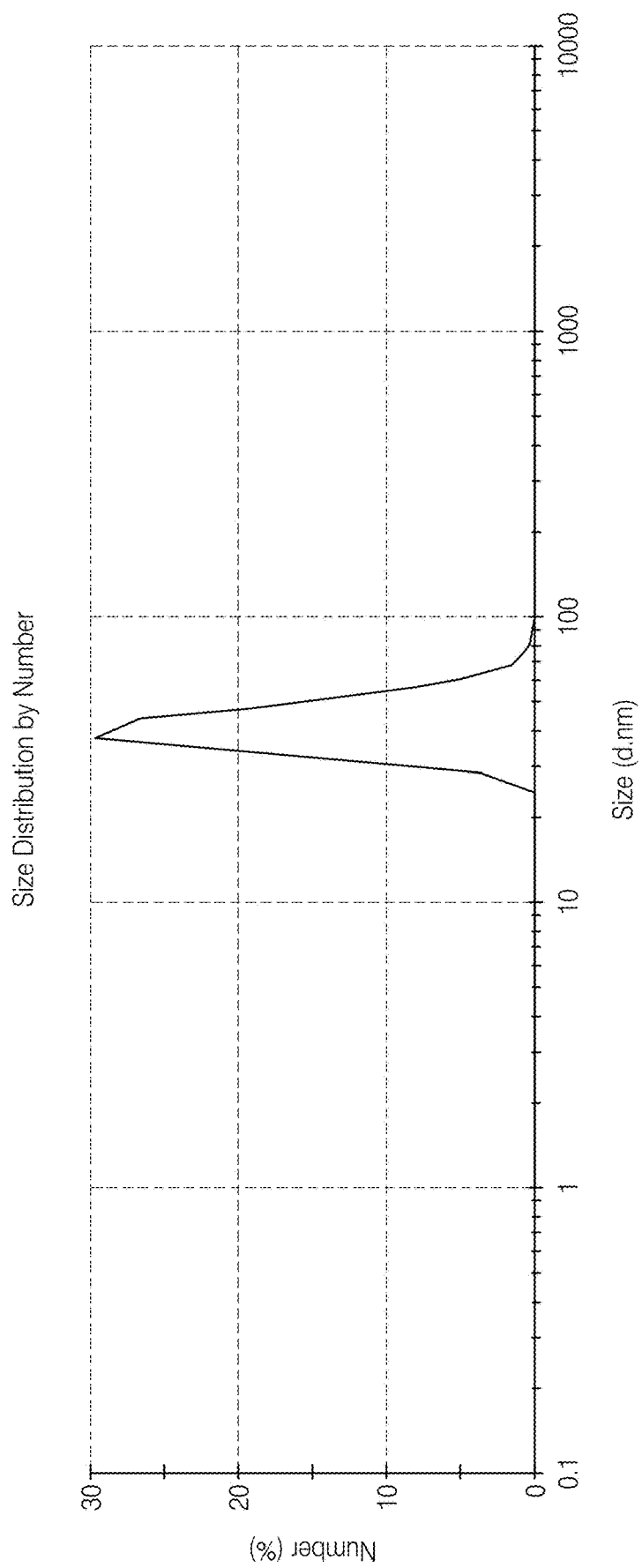
FIG. 7 shows the average number-weighted size of the polymeric micelles prepared using PEG-PLGA dissolved in ethanol as the first fluid and PBS as the second fluid.

The process described above and illustrated in FIG. 2 was also carried out in the fluidic device illustrated in FIG. 1 with dimensions provided in Table 1 using a first exemplary polymeric formulation. A polymeric formulation of PEG-PLGA (poly(ethylene glycol) methyl ether-block-poly(lactide-co-glycolide) (specific molecular weights: PEG Mn 2,000, PLGA Mn 4,500) dissolved in ethanol was utilized as the first fluid. Phosphate-buffered saline (PBS) (the second fluid) was then washed through the device, mixing with the first fluid to form polymeric micelles. The average number-weighted size of the micelles was determined to be 42.16 nm with a polydispersity index (PDI) of 0.251 (FIG. 7).

Figure 8:
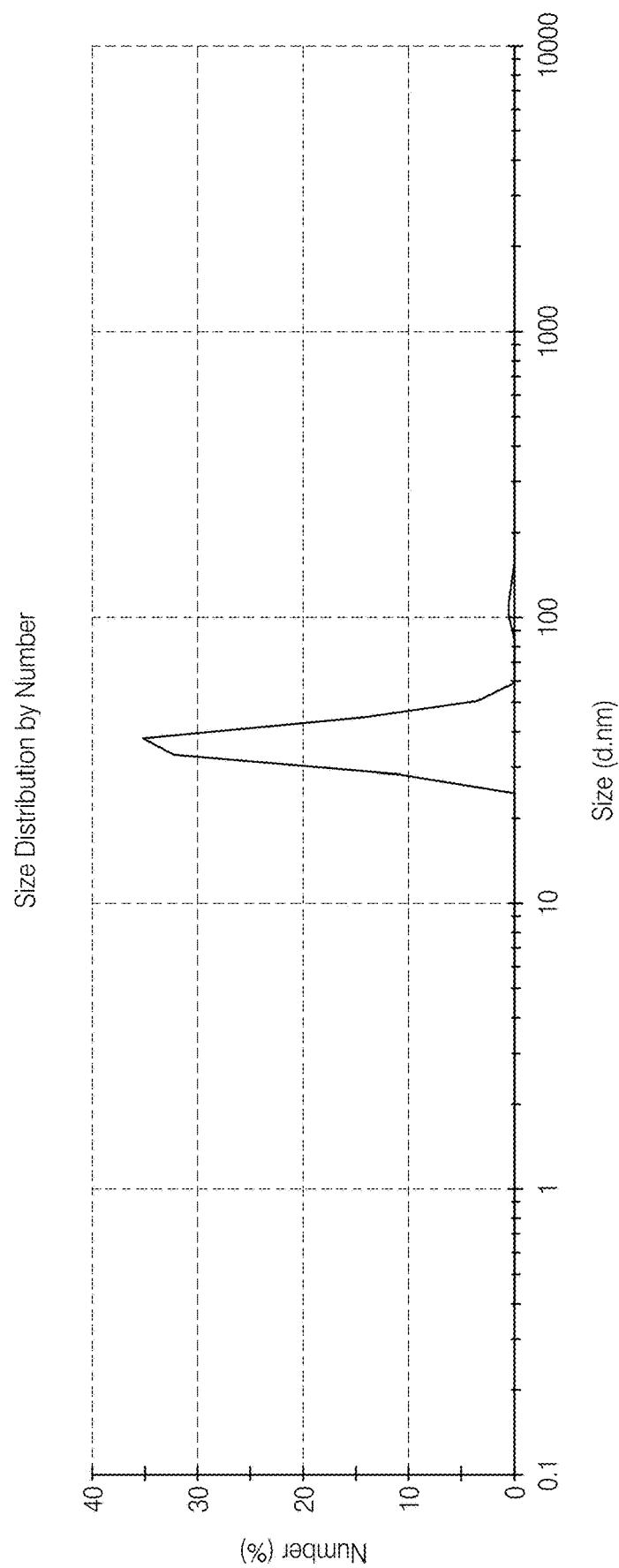
FIG. 8 shows the average number-weighted size of the polymeric micelles prepared using PEG-PLGA dissolved in acetone as the first fluid and distilled water as the second fluid.

The process described above and illustrated in FIGS. 2A-2C was also carried out in the fluidic device illustrated in FIG. 1 with dimensions provided in Table 1 using a second exemplary polymeric formulation. A polymeric formulation of PEG-PLGA dissolved in acetone was utilized as the first fluid. Distilled water (the second fluid) was then washed through the device, mixing with the first fluid to form polymeric micelles. The average number-weighted size of the micelles was determined to be 36.59 nm with a polydispersity index (PDI) of 0.155 (FIG. 8).

Figure 9:
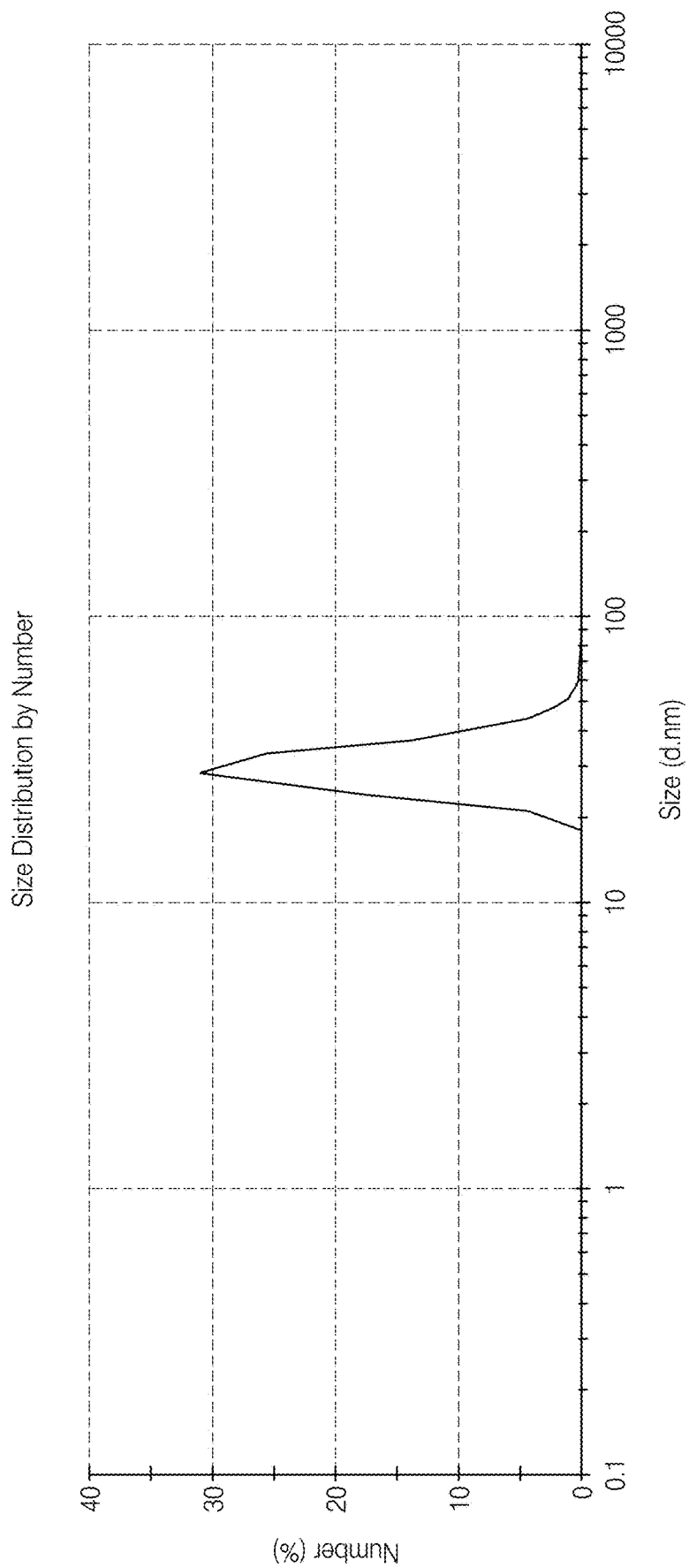
FIG. 9 shows the average number-weighted size of the polymeric micelles prepared using PEG-PLGA dissolved in ethanol as the first fluid and PBS as the second fluid.
Figure 10:
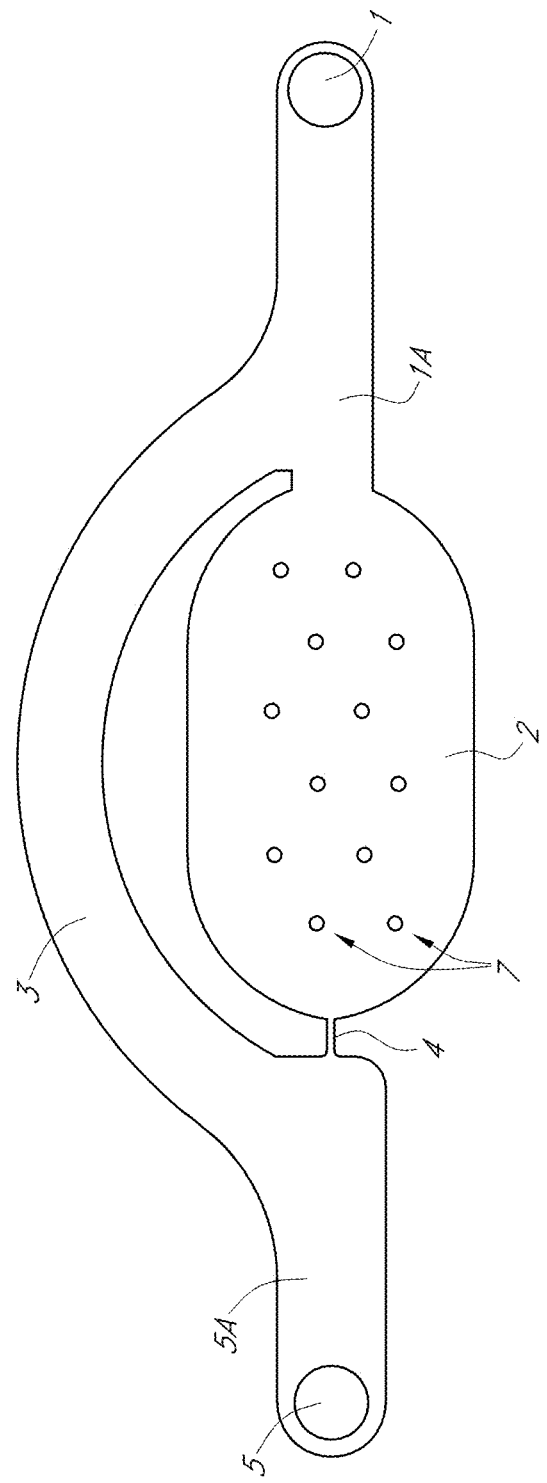
FIG. 10 illustrates an exemplary fluidic device including six pairs of two pillars 7 distributed within the reaction well 2 between the junction with the first fluid transport channel 1A and the fluid constriction channel 4 that can be used to produce nanoparticles.
Figure 11:
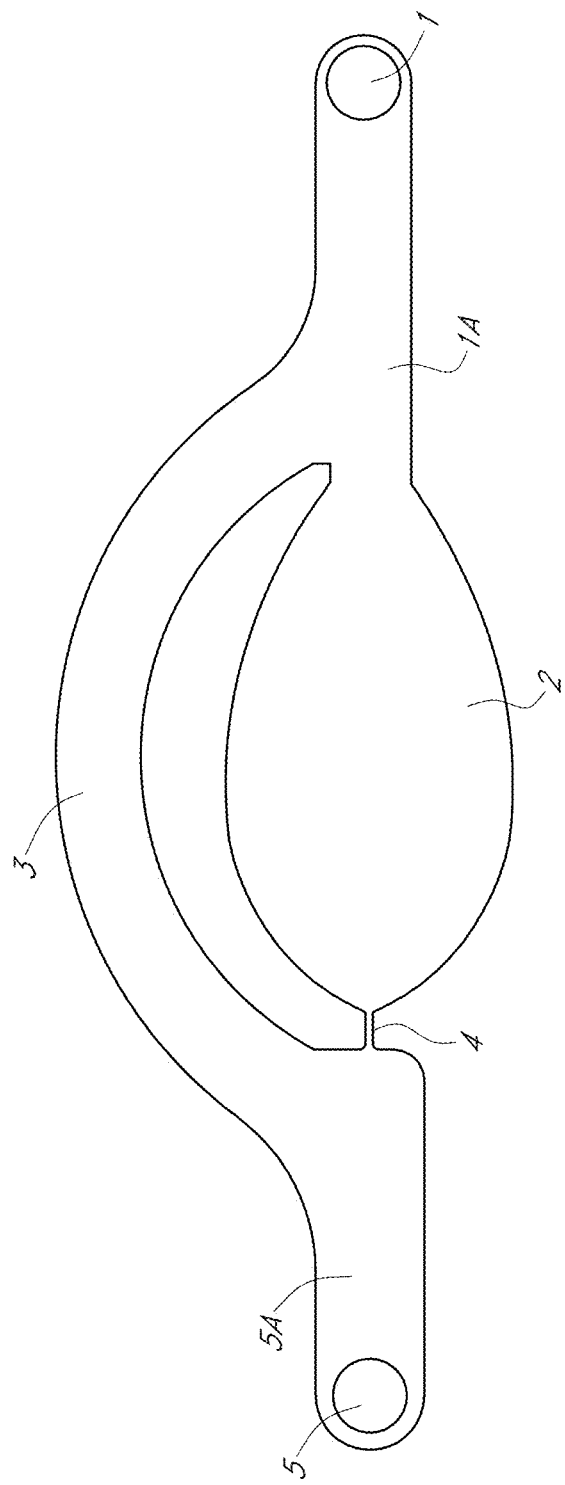
FIG. 11 illustrates an exemplary fluidic device in which the shape of the reaction well 2 was changed by reducing the curvature of the well on one side to alter flow patterns inside the reaction well 2 that can be used to produce nanoparticles.

The process described above and illustrated in FIGS. 2A-2C was also carried out in the fluidic device illustrated in FIG. 1 with dimensions provided in Table 1 using a third exemplary polymeric formulation. A polymeric formulation of PEG-PLGA dissolved in ethanol was utilized as the first fluid. Distilled water (the second fluid) was then washed through the device, mixing with the first fluid to form polymeric micelles. The average number-weighted size of the micelles was determined to be 30.97 nm with a polydispersity index (PDI) of 0.255 (FIG. 9).

Figure 14A:
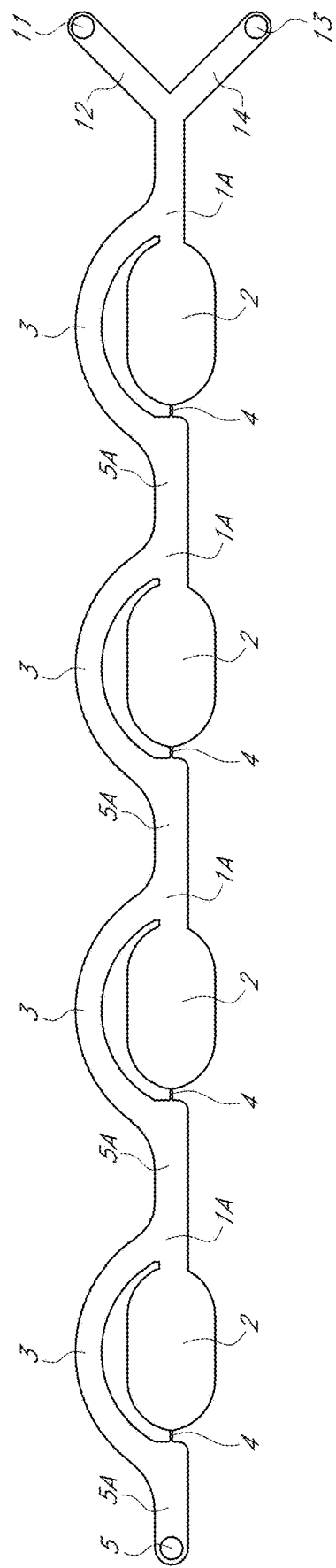
FIG. 14A illustrates an exemplary embodiment of a fluidic device comprising multiple fluidic device subunits with two inlet channels (12, 14) having associated separate inlet ports (11 and 13, respectively) that form a Y junction in fluid communication with the first fluid transport channel 1A of the first fluidic device in a series of fluidic devices.
Figure 14B:
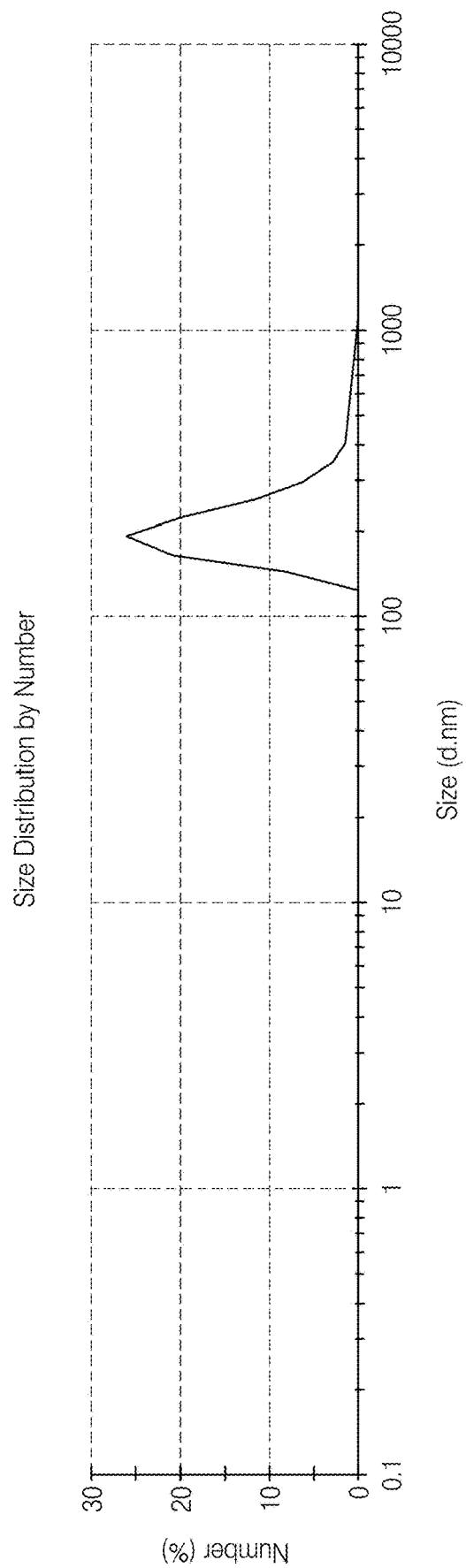
FIG. 14B provides the number-weighted size distribution for liposomes formulated using these first and second fluids in the device of FIG. 14A.

The coflowing fluidic device illustrated in FIG. 14A, which included 4 microfluidic device subunits arranged in series, was also used to produce liposomes. DPPC/Chol/DOTAP dissolved in ethanol (10 mg/mL) was introduced into the fluidic device through the first inlet port 11 at a flow rate of 5 mL/min, as PBS was introduced into the fluidic device through the second inlet port 13 at a flow rate of 20 mL/min. Liposomes were thereby produced. Number-weighted size distribution for liposomes formulated using these first and second fluids in this device was determined; the liposomes had an average size of 226.8 nm with a PDI of 0.153 (FIG. 14B).

Thus, the fluidic devices and methods described in this example were shown to be useful for producing lipid-based and polymer-based nanoparticles.

Example 2

Production of More Types of Nanoparticles Using Single Fluidic Devices

Figure 22A:
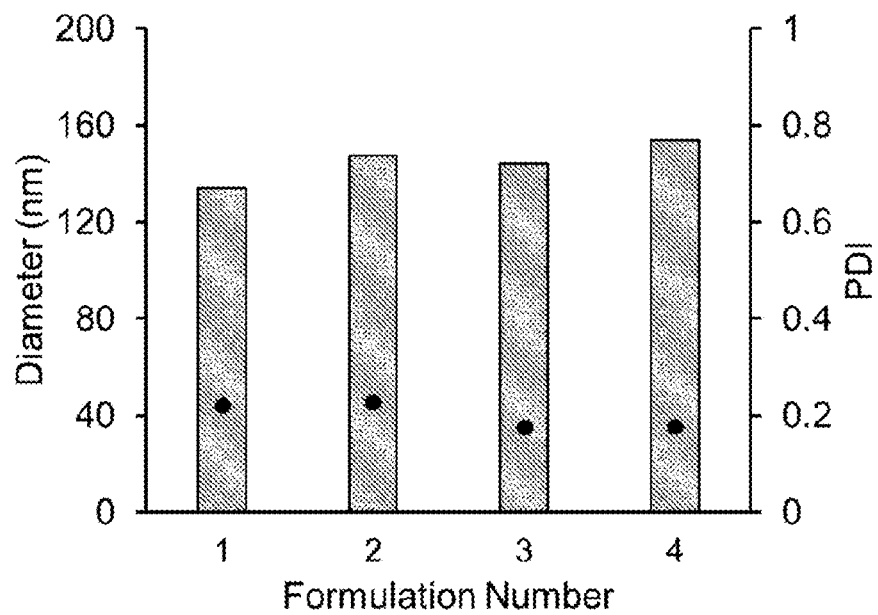
FIGS. 22A and 22B provides data generated using the a microfluidic device with the design shown in FIG. 1.

This example further illustrates the production of nanoparticles using a single subunit fluidic device with a single input port (i.e. inlet port or first port) 1 illustrated in FIG. 1. The process described above and illustrated in FIG. 2 was used with the device of FIG. 1 with dimensions provided in Table 1 for such device, with an exemplary DPPC/Cholesterol lipid formulation. A lipid formulation of DPPC/Cholesterol in a ratio of 60:40 was dissolved in ethanol at a concentration of 10 mg/mL and used as the first fluid and was loaded into the fluidic device (steps 1 and 2). The second fluid used was reagent grade water that was introduced into the device at a flow rate of 10 ml/minute using a syringe pump (step 3). Mixture of the first and second fluids in the fluidic device and following these steps resulted in liposomes being present in the reaction well 2. These liposomes were washed out of the reaction well 2 by inputting water into the first port 1 and analyzed using dynamic light scattering (DLS). The effective diameter of four batches of liposomes formulated in the device and analyzed by DLS is shown in FIG. 22A; the liposomes had an average size of 145 nm with a PDI of 0.2. The DLS data demonstrates that this fluidic device and method reproducibly generated consistent formulations.

Figure 22B:
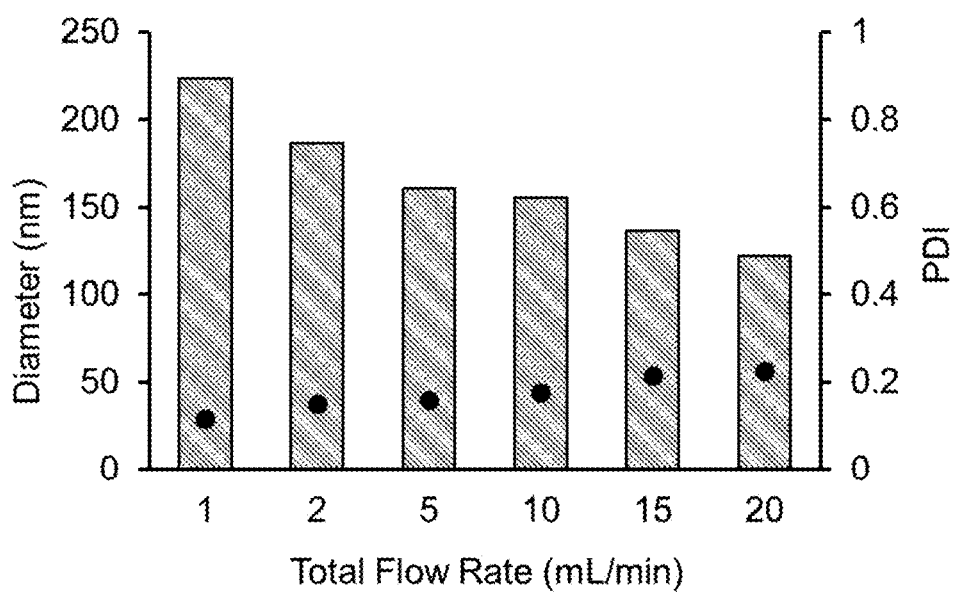

The effect of total flow rate on particle size is demonstrated in FIG. 22B. DPPC/Cholesterol in a ratio of 55:45 dissolved in ethanol at a concentration of 10 mg/mL was used as the first fluid and was loaded into the fluidic device (steps 1 and 2). The second fluid used was reagent grade water which was introduced into the device at a flow rate ranging from 1 to 20 ml/minute (step 3). As shown in FIG. 22B, a faster total flow rate resulted in the formation of smaller nanoparticles. Thus, microfluidic device designs similar to FIG. 1 provide efficient and flexible devices for preparing particles with sizes that can be controlled by using different, controlled flow rates.

Example 3

Production of Nanoparticles Using Fluidic Devices with Different Dimensions and a Series of Fluidic Device Subunits This example illustrates the production of nanoparticles using a coflowing fluidic device, or fluidic assembly, having a series of fluidic device subunits as illustrated in FIG. 20. The channel dimensions of two versions (small dimension version and larger relative dimensions version) that were prepared according to the device design shown in FIG. 20 are listed in Table 1. The small design in FIG. 20 functions the same as the large design of FIG. 20 but is capable of forming smaller nanoparticles due to the reduced dimensions of the parts of the device.

Figure 23A:
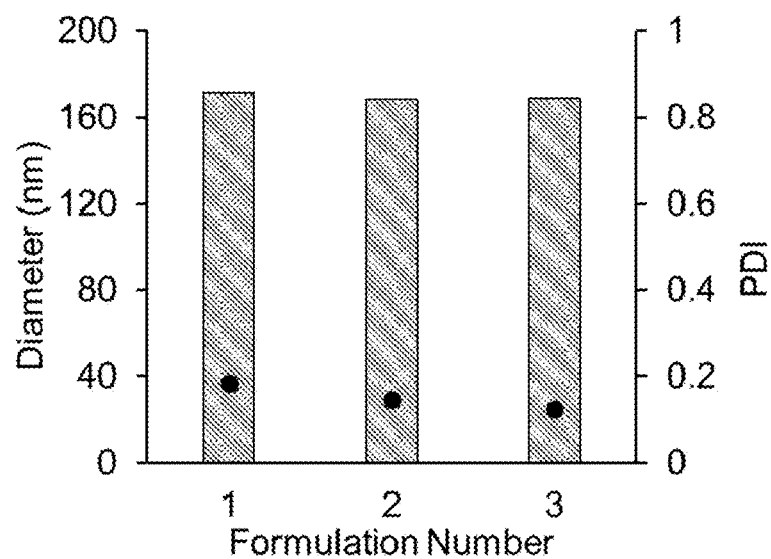
FIGS. 23A to 23D provide data generated using the a microfluidic device with the large dimension embodiment of the design shown in FIG. 20.

Approximately 0.27 ml of DPPC/Cholesterol in a ratio of 70:30 dissolved in ethanol at a concentration of 10 mg/mL (i.e. first fluid) was introduced into a fluidic device made according to the large dimension embodiment of the design of FIG. 20 through the first inlet port 11 at a flow rate of 0.9 mL/min, as about 2.73 ml of reagent grade water (i.e. second fluid) was introduced into the fluidic device through the second inlet port 13 at a flow rate of 9.1 mL/min using a peristaltic pump. Three batches of liposomes using these parameters were thereby produced and 3 mls of a suspension of liposome nanoparticles were collected for each batch from the second port 5. The three batches of collected liposome nanoparticles were analyzed by DLS (FIG. 23A). The effective diameter for three batches of liposomes formulated using these first and second fluids in this device was determined. The liposomes that were produced had a lipid concentration of 1 mg/ml, an average size (i.e. diameter) of 169.4 nm with a PDI of 0.15. The DLS data demonstrates that this large design fluidic device of FIG. 20, and method using the same, reproducibly generated consistent formulations. Thus, microfluidic device designs similar to FIG. 20 provide efficient and flexible devices for preparing particles with consistent batch to batch reproducibility for particle size.

Figure 23B:
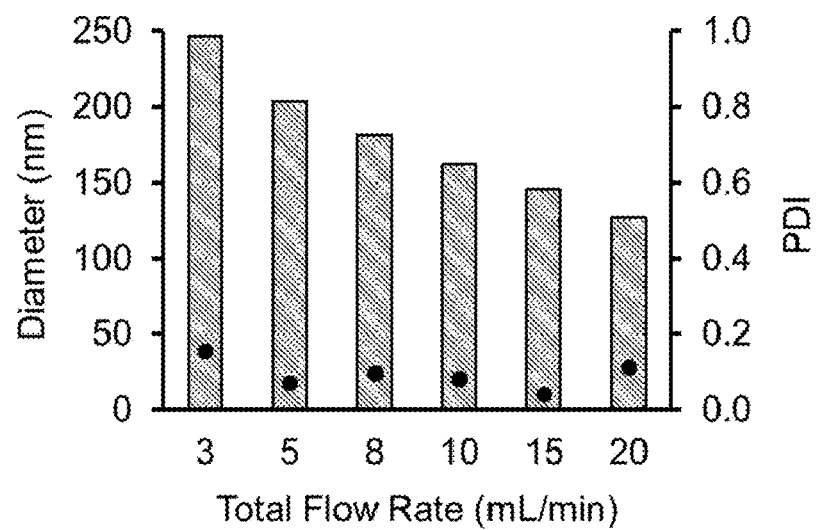

Approximately 0.27 ml of DPPC/Cholesterol in a ratio of 55:45 dissolved in ethanol at a concentration of 10 mg/mL (i.e. first fluid) was introduced into a fluidic device made according to the large dimension embodiment of the design of FIG. 20 through the first inlet port 11 at a certain flow rate, as about 2.73 ml of reagent grade water (i.e. second fluid) was introduced into the fluidic device through the second inlet port 13 at a flow rate ten times that of the lipid phase using a peristaltic pump. While maintaining a flow rate ratio of 1:10 between the first and second stream, the total flow rate of both streams combined was varied from 3 to 20 mL/min. The effective diameter for each batch of liposomes formulated using these first and second fluids in this device at these flow rates was determined using DLS. The lipid concentration of the produced liposome nanoparticles was 1 mg/ml. The data (FIG. 23B) demonstrates that particle size decreased as total flow rate increased. Thus, microfluidic device designs similar to FIG. 20 provide an efficient and flexible device for preparing particles with different sizes by altering flow rates of streams of liquids input into the device.

Figure 23C:
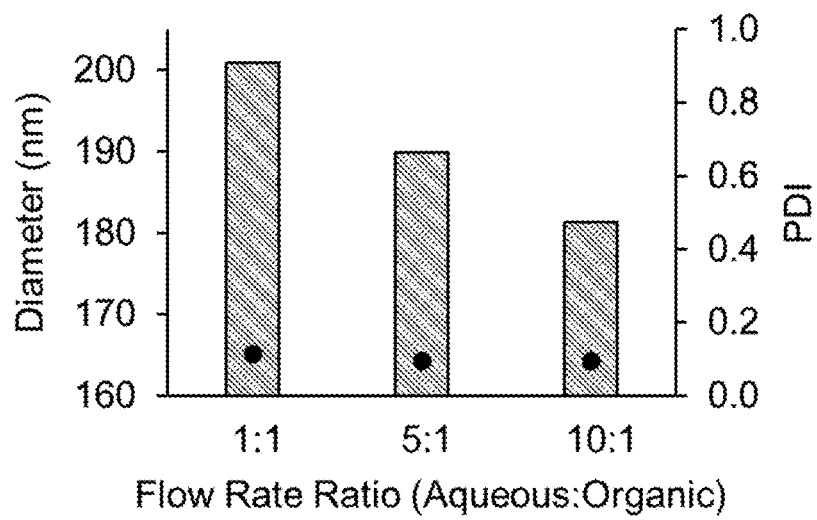

Approximately 0.27 ml of DPPC/Cholesterol in a ratio of 70:30 was dissolved in ethanol at a concentration of 10 mg/mL (i.e. first fluid). The lipid phase was introduced into a fluidic device made according to the large dimension embodiment of the design of FIG. 20 through the first inlet port 11 as about 2.73 ml of reagent grade water (i.e. second fluid) was introduced into the fluidic device through the second inlet port 13 using a peristaltic pump. The flow rates of the two streams were varied such that the total flow rate of both streams combined was held constant at 8 mL/min, but the ratio between the water and lipid phases was varied from 1:1 to 10:1. The effective diameter for each batch of liposomes formulated using these first and second fluids in this device at these flow rates was determined using DLS. The final lipid concentrations of the produced liposomes varied from 5 mg/ml to 1 mg/ml for flow rate rations of 1:1 to 10:1 respectively. The data (FIG. 23C) demonstrates that particle size decreased as flow rate ratio of water to lipid increased. Thus, microfluidic device designs similar to FIG. 20 provide an efficient and flexible device for preparing particles with different sizes by holding a combined flow rate of a first fluid stream and a second fluid stream constant, but varying the relative flow rates of the first fluid stream to the second fluid stream input into the device.

Figure 23D:
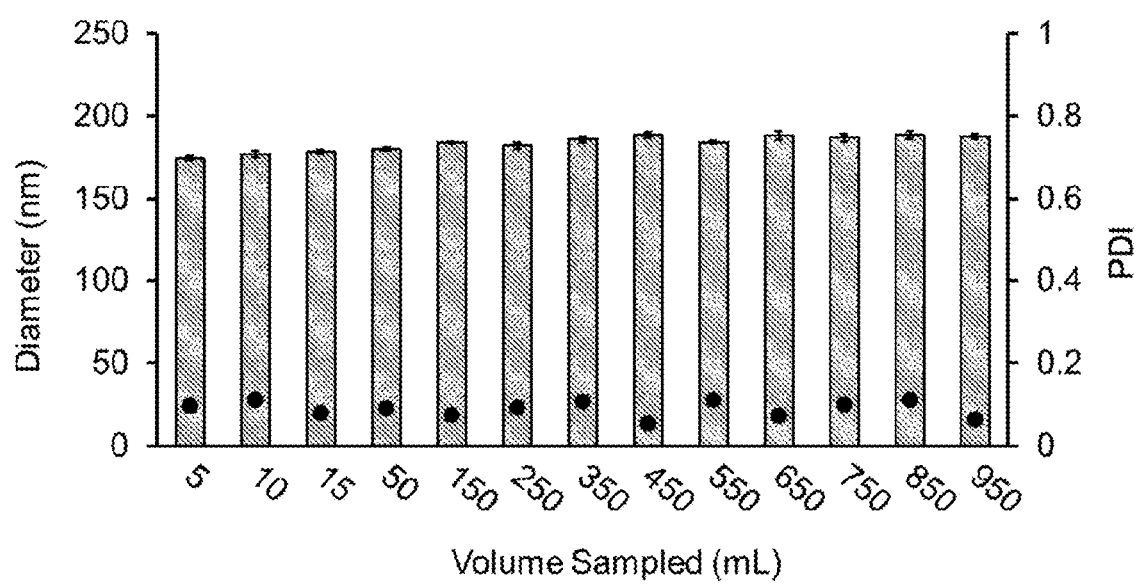

Approximately 90.9 ml of DPPC/Chol in a ratio of 70:30 dissolved in ethanol at a concentration of 10 mg/mL (i.e. first fluid) was introduced into a fluidic device made according to the large dimension embodiment of the design of FIG. 20 through the first inlet port 11 at a flow rate of 0.9 mL/min, as about 909.1 ml of reagent grade water (i.e. second fluid) was introduced into the fluidic device through the second inlet port 13 at a flow rate of 9.1 mL/min using a peristaltic pump. Liposomes were thereby produced. 1 L of formulation was prepared by continuously inputting the first fluid and second fluid into the device until 1 L of liposome nanoparticle solution was collected through port 5. Thirteen samples were collected throughout the formulation process. Each sample was measured using DLS. The lipid concentration of the produced liposome nanoparticles was 1 mg/ml. The data (FIG. 23D) demonstrates a high degree of uniformity across large batches of nanoparticle formulations. Thus, microfluidic device designs similar to FIG. 20 provide efficient and flexible devices for preparing particles in volumes that can be scaled up to liters of particle solutions or suspensions by inputting larger volumes of fluids into the device and collecting output microparticle solutions and suspensions as more first fluid and second fluid are being input into the device and microparticles are being formed within the device.

Figure 24A:
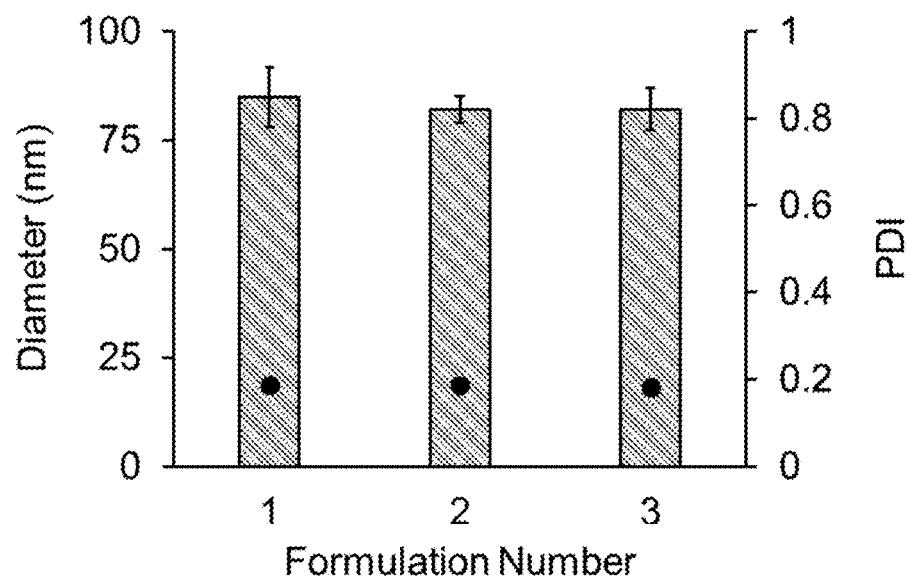
FIGS. 24A to 24C provide data generated using the a microfluidic device with the small dimension embodiment of the design shown in FIG. 20.

A device made according to the small dimension embodiment of the design of FIG. 20 was also used to produce liposomes. Approximately 0.27 ml of DPPC/Cholesterol in a ratio of 70:30 dissolved in ethanol at a concentration of 10 mg/mL (i.e. first fluid) was introduced into the small dimension fluidic device according to FIG. 20 through the first inlet port 11 at a flow rate of 1.4 mL/min, as about 2.73 ml of reagent grade water (i.e. second fluid) was introduced into the fluidic device through the second inlet port 13 at a flow rate of 13.6 mL/min using a peristaltic pump. Liposomes were thereby produced. The effective diameter for three batches of liposomes formulated using these first and second fluids in this device was determined using DLS (FIG. 24A). The lipid concentration of the produced liposome nanoparticles was 1 mg/ml. The liposomes had an average size of 83 nm with a PDI of 0.19. The DLS data demonstrates that this fluidic device and method reproducibly generated consistent formulations. Thus, microfluidic device designs similar to FIG. 20 but with different dimensions, provide efficient and flexible devices for preparing particles with consistent batch to batch reproducibility for particle size.

Figure 24B:
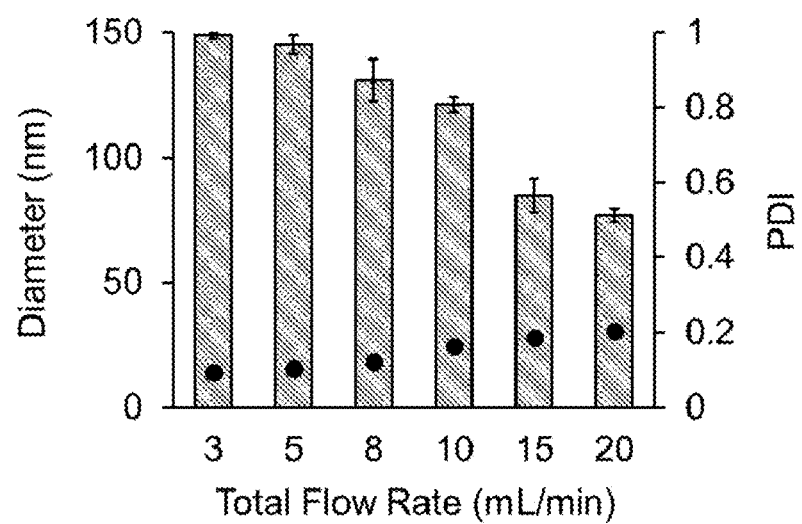

Approximately 0.27 ml of DPPC/Cholesterol in a ratio of 70:30 dissolved in ethanol at a concentration of 10 mg/mL (i.e. first fluid) was introduced into a fluidic device made according to the small dimension embodiment of the design of FIG. 20, through the first inlet port 11 at a certain flow rate, as about 2.73 ml of reagent grade water (i.e. second fluid) was introduced into the fluidic device through the second inlet port 13 at a flow rate ten times that of the lipid phase using a peristaltic pump. While maintaining a flow rate ratio of 1:10 between the first and second stream, the total flow rate of both streams combined was varied from 3 to 20 mL/min. The effective diameter for each batch of liposomes formulated using these first and second fluids in this device at these flow rates was determined using DLS. The lipid concentration of the produced liposome nanoparticles was 1 mg/ml. The data (FIG. 24B) demonstrates that particle size decreased as total flow rate increased. Thus, microfluidic device designs similar to FIG. 20 at different dimensions, provide an efficient and flexible device for preparing particles with different sizes by altering a total flow rate of combined streams of fluids input into the device.

Figure 24C:
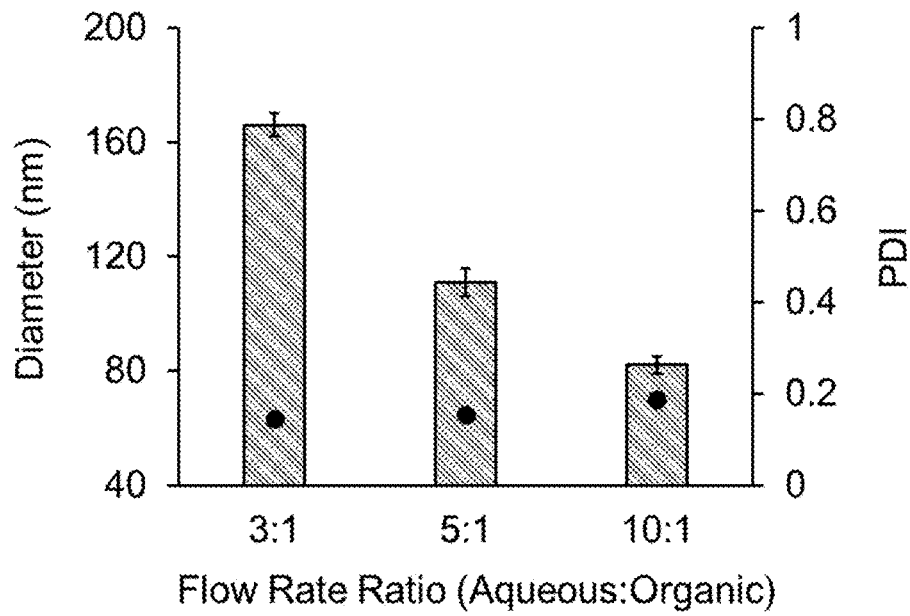

Approximately 0.27 ml of DPPC/Cholesterol in a ratio of 70:30 was dissolved in ethanol at a concentration of 10 mg/mL (i.e. first fluid). The lipid phase was introduced into a fluidic device made according to the small dimension embodiment of the design of FIG. 20, through the first inlet port 1 as about 2.73 ml of reagent grade water was introduced into the fluidic device through the second inlet port 13 using a peristaltic pump. The flow rates of the two streams were varied such that the total flow rate of both streams combined was held constant at 15 mL/min, but the ratio between the water and lipid phases was varied from 3:1 to 10:1. The lipid concentration of the produced liposome nanoparticles was between 3.33 mg/ml to 1 mg/ml at the 3:1 and 10:1 ratios, respectively. The effective diameter for each batch of liposomes formulated using these first and second fluids in this device at these flow rates was determined using DLS. The data (FIG. 24C) demonstrates that particle size decreased as flow rate ratio increased between the water stream and the lipid stream. Thus, microfluidic device designs similar to FIG. 20 and with different dimensions provide an efficient and flexible device for preparing particles with different sizes by holding a combined flow rate of a first fluid stream and a second fluid stream constant, but varying the relative flow rates of the first fluid stream to the second fluid stream input into the device.

Example 4

Production of Protein Precipitants Using Fluidic Devices

A fluidic device made according to the small dimension embodiment of the design of FIG. 20 was used to precipitate proteins from solutions and quantify precipitation efficiency. The two input fluid streams were (1) different protein solutions and (2) applicable precipitants known to precipitate a protein of interest from a protein solution.

Precipitation of proteins using the small dimension embodiment of the design of FIG. 20 was demonstrated using two model proteins, Bovine Serum Albumin (BSA) and Bovine Gamma Globulin, and Trichloroacetic acid (TCA) as a precipitant. BSA was dissolved in Phosphate Buffered Saline (PBS) at a concentration of 10 mg/mL, and Bovine Gamma Globulin was dissolved in PBS at a concentration of 5 mg/mL. In the first experiment, the BSA PBS solution and an aqueous solution of 4% TCA were used as inputs (i.e. first fluid and second fluid respectively) to the device. Total flow rate was maintained at 2 mL/min and a range of flow rate ratios (BSA:TCA) of 1:1, 2:1, 5:1 and 10:1 were tested to gauge precipitation efficiency. Precipitation efficiency is given as a percent and is defined as: [1-(Protein Concentration in Supernatant÷Input Protein Concentration)]*100.

Figure 25:
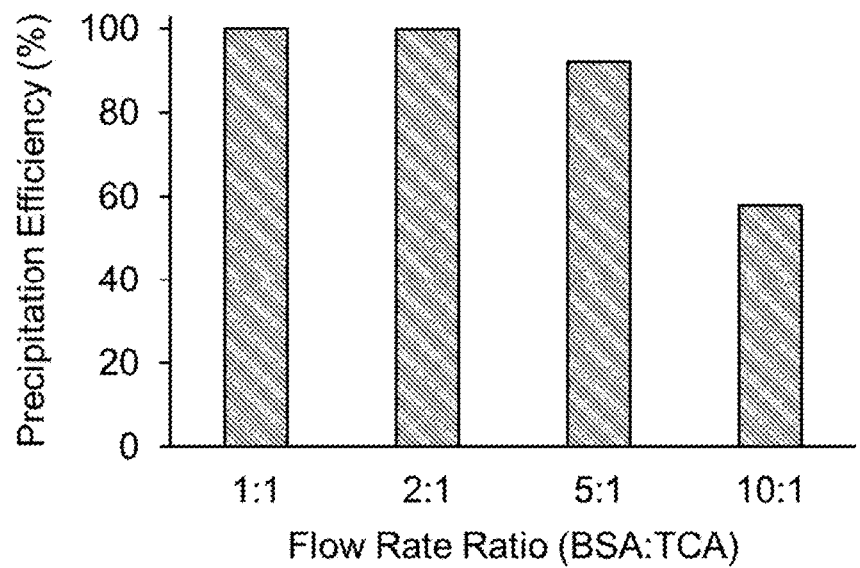
FIG. 25 provides data generated using the a microfluidic device with the large embodiment of the design shown in FIG. 20 to precipitate proteins. Precipitate efficiency is graphed for protein precipitation experiments performed at different flow rate rations of BSA to TCA.

Input concentration was known, and supernatant concentration was estimated using a Bradford protein assay. The efficiency of precipitation in each case was 99.97%, 99.9%, 92.06% and 58.00%, respectively (shown in FIG. 25).

In the second experiment, Bovine Gamma Globulin in PBS and 4% TCA were used as first fluid and second fluid inputs, respectively, and input into the device. Bovine Gamma Globulin was precipitated at total flow rates of 500 µL/min and 2 mL/min with an efficiency of 99.16% and 99.58% when the two incoming streams were delivered at a 1:1 flow rate ratio.

Protein precipitant concentrations were determined to be 2%, 1.33%, 0.67% and 0.36% at the 4 different flow rate ratios above (1:1, 2:1, 5:1, 10:1) using BSA. Thus, protein precipitant concentrations were low, but precipitate was formed with very high efficiency. Low protein precipitant concentration is beneficial because precipitant can have damaging effects on the protein. These results demonstrate that devices and methods provided herein can be used to produce low concentrations of precipitant while still precipitating out high levels of protein.

These results demonstrate that devices with the general design of FIG. 20, were effective for producing protein precipitations using proteins with very different molecular weights and characteristics. Thus, devices provided herein, for example with the general design of FIG. 20, can be used to provide devices that are effective for, adapted for, and operable for use in methods that produce a continuous stream of a suspension of a precipitate of a target protein(s) when streams of a protein solution and a protein precipitant solution are simultaneously input into the device.

Example 5

Precipitate Detection Using a Device for Detecting a Reaction Product

Figure 15A:
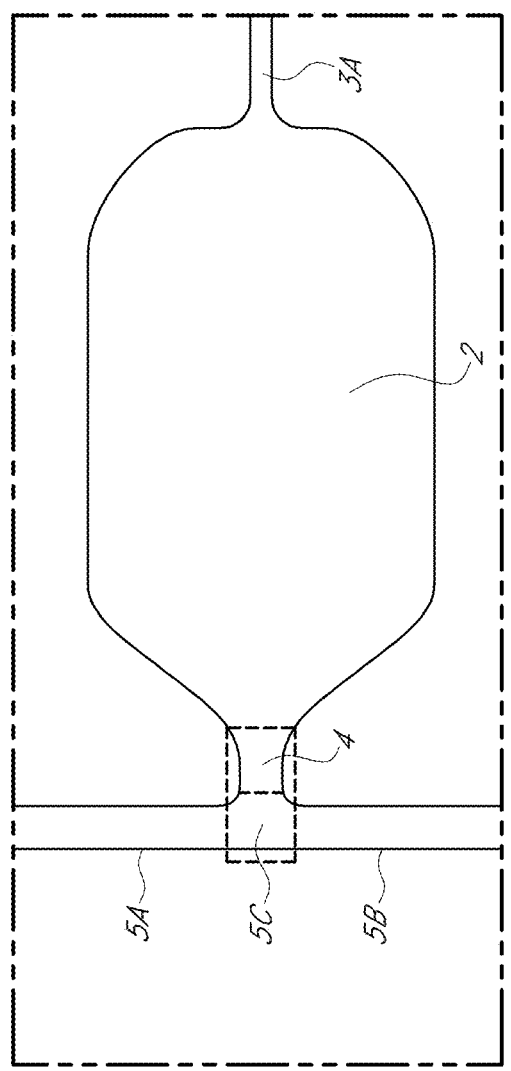

As noted herein, the exemplary device illustrated in FIGS. 15 and 15A and similar devices disclosed herein, can be used for reaction product detection, measurement, and analysis, for example in compound precipitation studies. In the embodiment provided in this example, a device according to FIGS. 15 and 15A was designed to model the in vivo conditions of a sweat gland to study interaction of active compounds found in a solution including compounds useful as anti-precipitants (e.g., the first fluid, which is trapped in the reaction well 2 during use) with a solution mimicking sweat solution (e.g., the second fluid). Eccrine sweat glands have a pore diameter of around 20-60 µm (Bretagne, 2017), and the second and third fluid transport channels (5B and 5A) of this exemplary device were accordingly designed to provide a similar geometry, having in this illustrative embodiment, a channel width and depth of 60 µm each for this application (but can be within a range, for example as provided in Table 2). The reaction well 2 in this exemplary device also has a channel depth of 60 µm, but this is not an absolutely required depth and can be within a range of, e.g., +/−10%.

The method disclosed in this Example was carried out by capturing a first fluid (i.e., the solution including potential anti-perspirant compound(s)) in a reaction well 2 and then introducing the second fluid (i.e., human sweat) via a third port 6 to interact with the first fluid, essentially as described hereinabove with reference to FIGS. 15-19. While devices constructed with dimensions provided in Table 2 can be used to carry out these methods, the fluidic device used in this Example had the following dimensions: a) depth of device: ~60 µm; b) third fluid transport channel 5B: 60 µm width, 1675 µm length; c) second fluid transport channel 5A: 60 µm width, 600 µm length; d) reaction well 2: 460 µm width (widest), 830 µm length; e) pressure sensing channel 3A: 40 µm width, ~ 2525 µm length; and, f) first fluid transport channel 1A: 460 µm width, ~ 12250 µm. A camera was used to capture movement of fluids into and out of the device on video, with a still frame from the video shown in FIG. 19. The temperature of the device was maintained at 37° C. with a commercially available temperature controller.

Figure 19:
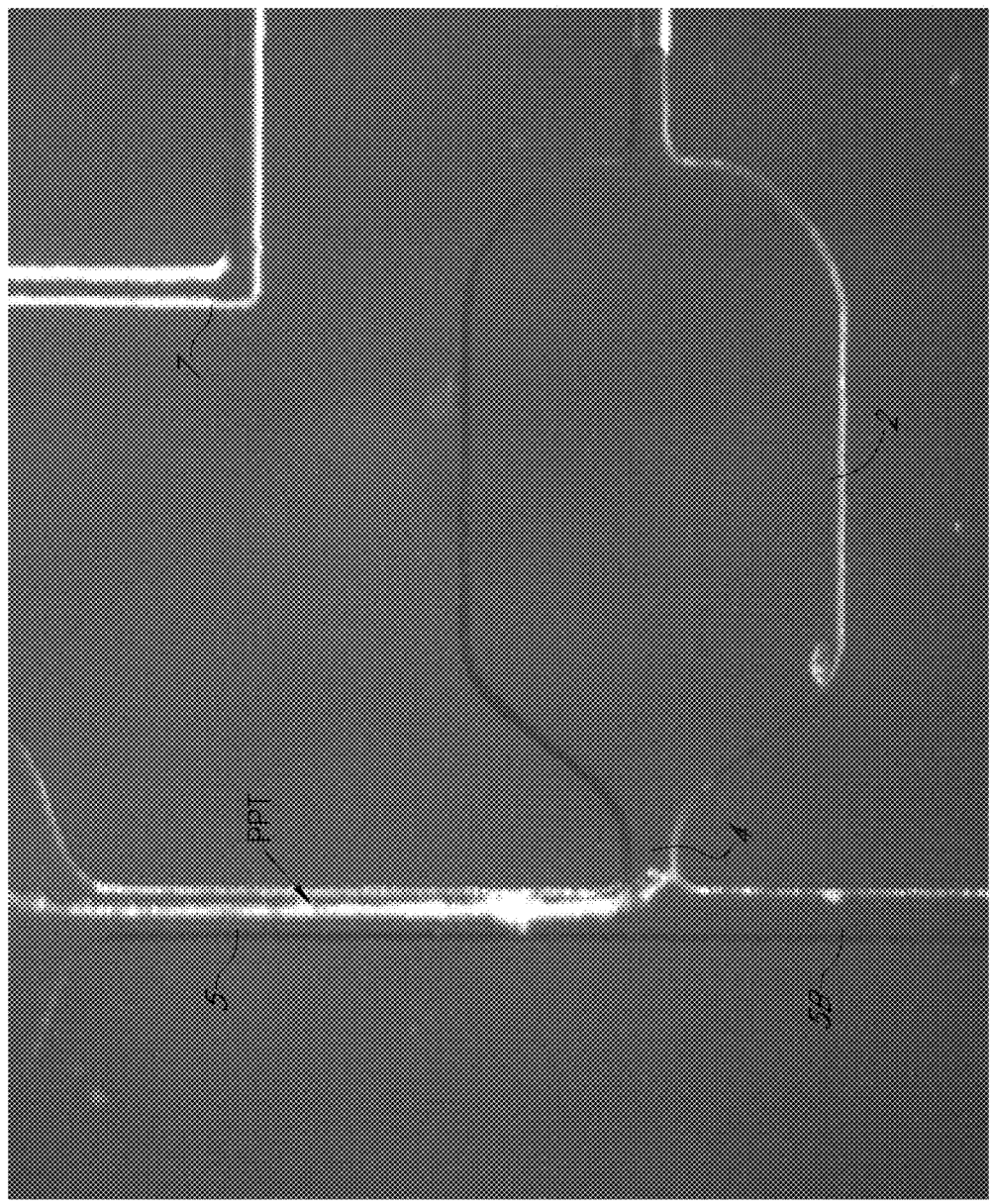
FIG. 19 shows a screenshot (still frame) from a video showing precipitate formation ("PPT") following the interaction of the first and second fluids. The device used to produce the precipitate shown in this figure included an optional thin channel 7 extending from the passive pressure sensing channel to the first fluid transport channel, not shown in FIG. 15. The width of that channel was the same width as the pressure sensing channel. Removing this optional thin channel 7 had no significant effect on the functionality of the device.

A first fluid containing a commercially-available anti-perspirant active compound (aluminum/zirconium tetrachlorohydrex, aluminum/zirconium pentachlorohydrate, or aluminum chlorohydrate) was the first fluid loaded into the reaction well by using positive pressure to introduce approximately 5 µl through the first port 1. Next, excess first fluid was removed from the device by applying a negative pressure at the first port with a standard manual pipette, leaving approximately 20 nL of active compound captured in the reaction well. Real mammalian sweat, collected from a healthy individual, was added to the device through the third port 6 with an applied positive pressure at a flow rate of 1 µl/min using a standard syringe pump. As incoming sweat and captured active compound in the reaction well 2 interacted over time, a precipitate plug (PPT) formed and continued to grow in the second fluid transport channel 5A, eventually completely blocking the incoming flow as observed by video analysis (FIG. 19). Representative precipitate area data measured from video images from these precipitates formed using a first fluid comprising aluminum/zirconium pentachlorohydrate and human sweat as the second fluid is shown in Table 3 below (flow rate of 1 µl/min, constant temperature of 37° C.):

TABLE 3

| Time (min) | Precipitate area (mm$^2$) |
| --- | --- |
| 0 | 0 |
| 5 | 0 |
| 10 | 0.004528 |
| 15 | 0.006348 |
| 20 | 0.011742 |
| 25 | 0.014538 |
| 30 | 0.017032 |
| 35 | 0.020998 |
| 40 | 0.023918 |

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below.

Accordingly, the specification and figures are to be regarded in an illustrative rather than a restrictive sense, and all such modifications are intended to be included within the scope of the aspects and embodiments herein.

What is claimed is:

1. A fluidic device assembly comprising at least two microfluidic devices in a disposable cartridge, wherein each fluidic device comprises:
   a) a first port;
   b) a first fluid transport channel in fluid connection with:
      i. the first port;
      ii. a reaction well; and
      iii. an overflow channel;
   c) a second fluid transport channel in direct fluid communication with the overflow channel;
   d) a fluidic constriction channel in direct fluid communication with the reaction well and the second fluid transport channel; and
   e) a second port in direct fluid communication with the second fluid transport channel.

2. The fluidic device assembly of claim 1, wherein the at least two microfluidic devices are connected in series.

3. The fluidic device assembly of claim 1, wherein the at least two microfluidic devices are connected in parallel.

4. The fluidic device assembly of claim 1, wherein each fluidic device further comprises a passive air control valve.

5. The fluidic device assembly of claim 1, wherein a width or an effective diameter of the fluidic constriction channel is between 50 μm and 300 μm.

6. The fluidic device assembly of claim 1, wherein a width, diameter or effective diameter of the fluidic constriction channel is approximately 0.15 to approximately 0.30 times the width, diameter, or effective diameter of the reaction well.

7. The fluidic device assembly of claim 1, wherein the reaction well comprises at least one pillar.

8. A method for producing a reaction product using a fluidic device assembly, the fluidic device assembly comprising at least two microfluidic devices in a disposable cartridge, wherein each fluidic device comprises:
   a) a first port;
   b) a first fluid transport channel in fluid connection with:
      i. the first port;
      ii. a reaction well; and
      iii. an overflow channel;
   c) a second fluid transport channel in direct fluid communication with the overflow channel;
   d) a fluidic constriction channel in direct fluid communication with the reaction well and the second fluid transport channel; and
   e) a second port in direct fluid communication with the second fluid transport channel, and
   wherein the method comprises:
   a) introducing a first fluid into the first fluidic channel of each of the at least two fluidic devices;
   b) introducing a second fluid into the first fluidic channel of each of the at two fluidic devices; and
   c) producing a reaction product by mixing the first fluid and the second fluid in the reaction well of each of the at least two fluidic devices.

9. The method of claim 8, wherein the reaction product is continuously harvested from the fluidic device assembly.

10. The method of claim 8, wherein producing the reaction product further comprises:
    a. trapping the first fluid in the reaction well and the fluidic constriction channel connected therewith;
    b. applying negative pressure at a first port to remove some of the first fluid from the reaction well; and
    c. introducing the second fluid into the reaction well to mix with and replace the first fluid.

11. The method of claim 8, further comprising transforming a laminar flow of the first fluid and the second fluid into an unstable flow, but not a turbulent flow.

12. The method of claim 8, wherein the first fluid comprises a protein, wherein the second fluid is a protein precipitant, and wherein the reaction product comprises a protein precipitate comprising the protein.

13. The method of claim 8, wherein the first fluid comprises an organic solvent solution comprising dissolved lipids, or a polymer solution comprising at least one polymer dissolved in a solvent, and the second fluid comprises an aqueous buffer, and wherein the reaction product is a solution or suspension of particles.

14. The method of claim 13, wherein the solution or suspension of particles is a solution or suspension of nanoparticles.

15. The method of claim 8, wherein the first fluid comprises an organic solvent solution comprising dissolved lipids, and wherein the dissolved lipids comprise at least one lipid selected from the group consisting of dipalmitoylphosphatidylcholine (DPPC); cholesterol; 1,2-Dilauroyl-sn-glycero-3-phosphocholine (DLPC); 1,2-Dimyristoyl-sn-glycero-3-phosphocholine (DMPC); 1,2-Distearoyl-sn-glycero-3-phosphocholine (DSPC); 1,2-Dioleoyl-sn-glycero-3-phosphocholine (DOPC); 1,2-Dimyristoyl-sn-glycero-3-phosphoethanolamine (DMPE); 1,2-Dipalmitoyl-sn-glycero-3-phosphoethanolamine (DPPE); 1,2-Dioleoyl-sn-glycero-3-phosphoethanolamine (DOPE); 1,2-Dimyristoyl-sn-glycero-3-phosphate, sodium salt (DMPA); 1,2-Dipalmitoyl-sn-glycero-3-phosphate, sodium salt (DPPA); 1,2-dioleoyl-sn-glycero-3-phosphate, sodium salt (DOPA); 1,2-Dimyristoyl-sn-glycero-3-phosphoglycerol, sodium salt (DMPG); 1,2-Dipalmitoyl-sn-glycero-3-phosphoglycerol, sodium salt (DPPG); 1,2-dimyristoyl-sn-glycero-3-phospho-L-serine, sodium salt; 1,2-Dipalmitoyl-sn-glycero-3-phosphoserine, sodium salt (DPPS); 1,2-dioleoyl-sn-glycero-3-phospho-L-serine (DOPS), sodium salt; 1,2-Dioleoyl-sn-glycero-3-phosphoethanolamine (DOPE)-Glutaryl, sodium salt; tetramyristoyl cardiolipin sodium salt; 1,2-Distearoyl-sn-glycero-3-phosphoethanolamine (DSPE)-mPEG-2000, sodium salt; 1,2-Distearoyl-sn-glycero-3-phosphoethanolamine (DSPE)-mPEG-5000, sodium salt; and 1,2-Distearoyl-sn-glycero-3-phosphoethanolamine (DSPE)-Maleimide PEG-2000, sodium salt, and a mixture thereof.

* * * * *

UNITED STATES PATENT AND TRADEMARK OFFICE
CERTIFICATE OF CORRECTION

| | | |
|---|---|---|
| PATENT NO. | : 11,998,885 B2 | Page 1 of 1 |
| APPLICATION NO. | : 17/288813 | |
| DATED | : June 4, 2024 | |
| INVENTOR(S) | : Solomon | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 492 days.

Signed and Sealed this
Fourth Day of March, 2025

Coke Morgan Stewart
*Acting Director of the United States Patent and Trademark Office*